US010988502B2

(12) United States Patent
Zetterberg et al.

(10) Patent No.: US 10,988,502 B2
(45) Date of Patent: *Apr. 27, 2021

(54) ALPHA-D-GALACTOSIDE INHIBITORS OF GALECTINS

(71) Applicant: GALECTO BIOTECH AB, Copenhagen (DK)

(72) Inventors: Fredrik Zetterberg, Askim (SE); Hakon Leffler, Lund (SE); Ulf Nilsson, Lund (SE)

(73) Assignee: GALECTO BIOTECH AB, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/313,625

(22) PCT Filed: Jul. 9, 2017

(86) PCT No.: PCT/EP2017/067180
§ 371 (c)(1),
(2) Date: Dec. 27, 2018

(87) PCT Pub. No.: WO2018/011093
PCT Pub. Date: Jan. 18, 2018

(65) Prior Publication Data
US 2019/0225638 A1    Jul. 25, 2019

(30) Foreign Application Priority Data

Jul. 12, 2016 (EP) .................................... 16179060

(51) Int. Cl.
*C07H 15/203* (2006.01)
*C07H 19/056* (2006.01)
*C07C 17/02* (2006.01)
*C07H 17/02* (2006.01)

(52) U.S. Cl.
CPC ........... *C07H 15/203* (2013.01); *C07H 17/02* (2013.01); *C07H 19/056* (2013.01)

(58) Field of Classification Search
CPC ...... A61P 9/10; A61P 9/04; A61P 9/00; A61P 37/06; A61P 35/04; A61P 3/10; A61P 35/00; A61P 31/04; A61P 3/04; A61P 3/00; A61P 29/00; A61P 27/02; A61P 19/02; A61P 19/00; A61P 17/06; A61P 17/00; A61P 13/12; A61P 11/06; A61P 11/00; A61P 1/16; A61P 43/00; A61P 1/04; C07H 15/203; C07H 19/056; C07H 17/02

See application file for complete search history.

(56) References Cited

U.S. PATENT DOCUMENTS 10,774,102 B2 * 9/2020 Brimert ...................... A61P 3/00
2017/0349619 A1 * 12/2017 Brimert ................ C07H 15/203

FOREIGN PATENT DOCUMENTS

WO    2005/113569 A1    12/2005
WO    2010/126435 A1    11/2010
WO    2016/120403 A1     8/2016
WO    WO-2016120403 A1 *  8/2016 ............. C07H 13/08

OTHER PUBLICATIONS

International Search Report and Written Opinion of the International Searching Authority dated Aug. 17, 2017 in corresponding International application No. PCT/EP2017/067180; 13 pages.
Giguère et al., "Inhibitory potential of chemical substitutions at bioinspired sites of β-d-galactopyranose on neoglycoprotein/cell surface binding of two classes of medically relevant lectins", Bioorganic & Medicinal Chemistry, Mar. 9, 2011, vol. 19, No. 10, p. 3280-3287; 8 pages.
Rajput et al., "Synthesis and evaluation of iminocoumaryl and coumaryl derivatized glycosides as galectin antagonists", Bioorganic & Medicinal Chemistry Letters, Jun. 9, 2014, vol. 24, No. 15, p. 3516-3520; 5 pages.
Almkvist et al., "Lipopolysaccharide-Induced Gelatinase Granule Mobilization Primes Neutrophils for Activation by Galectin-3 and Formylmethionyl-Leu-Phe", in Infection and Immunity, vol. 69, No. 2, Feb. 2001, p. 832-837; 6 pages.
Barondes et al., "Galectins", in The Journal of Biological Chemistry, vol. 269, No. 33, Aug. 19, 1994, p. 20807-20810; 4 pages.
Blois et al., "A pivotal role for galectin-1 in fetomatemal tolerance", in Nature Medicine, vol. 13, No. 12, Dec. 2007, p. 1450-1457; 9 pages.
Chen et al., "Targeting Galectin-1 and Galectin-3 Attenuates VEGF-A-induced Angiogenesis", in Molecular Biology Cell (suppl), Abstract, No. 2695, 2012; 1 page.
Cumpstey et al., "Synthesis of a phenyl thio-β-D-galactopyranoside library from 1,5-difluoro-2,4-dinitrobenzene: discovery of efficient and selective monosaccharide inhibitors of galectin-7", in Org. Biomol. Chem., vol. 3, 2005, p. 1922-1932; 11 pages.
Cumpstey et al., "C2-Symmetrical thiodigalactoside bis-benzamido derivatives as high-affinity inhibitors of galectin-3: Efficient lectin inhibition through double arginine-arene interactions", in Angew. Chem. Int., Ed. 44, 2005, p. 5110-5112; 3 pages.
Cumpstey et al., "Double Affinity Amplification of Galectin-Ligand Interactions through Arginine-Arene Interactions: Synthetic, Thermodynamic, and Computational Studies with Aromatic Diamido Thiodigalactosides", in Chem. Eur. J., vol. 14, 2008, p. 4233-4245; 13 pages.

(Continued)

*Primary Examiner* — Amanda L. Aguirre
(74) *Attorney, Agent, or Firm* — Maier & Maier, PLLC

(57) ABSTRACT

The present invention relates to a compound of the general formula (1). The compound of formula (1) is suitable for use in a method for treating a disorder relating to the binding of a galectin, such as galectin-1 to a ligand in a mammal, such as a human. Furthermore, the present invention concerns a method for treatment of a disorder relating to the binding of a galectin, such as galectin-1 to a ligand in a mammal, such as a human.

24 Claims, No Drawings

(56) References Cited

OTHER PUBLICATIONS

Dam et al., "Effects of Clustered Epitopes in Multivalent Ligand-Receptor Interactions", in Biochemistry, vol. 47, 2008, p. 8470-8476; 7 pages.
Delacour et al., "Apical Sorting by Galectin-3-Dependent Glycoprotein Clustering", in Traffic, vol. 8, 2007, p. 379-388; 10 pages.
Delaine et al., "Galectin-Inhibitory Thiodigalactoside Ester Derivatives Have Antimigratory Effects in Cultured Lung and Prostate Cancer Cells", in J. Med. Chem., vol. 51, 2008, p. 8109-8114; 6 pages.
Demotte et al., "A Galectin-3 Ligand Corrects the Impaired Function of Human CD4 and CD8 Tumor-Infiltrating Lymphocytes and Favors Tumor Rejection in Mice", in Cancer Research, vol. 70, 2010, p. 7476-7488; 14 pages.
Farkas et al., "Synthesis of 1,2-trans-glycopyranosyl chlorides using the dichloromethyl methyl ether-boron trifluoride etherate reagent", in Carbohydrate Research, vol. 48, 1976, p. 136-138; 3 pages.
Garner et al., "Galectin-glycan lattices regulate cell-surface glycoprotein organization and signalling", in Biochemical Society Transactions, vol. 36, Part 6, 2008, p. 1472-1477; 6 pages.
Giguère et al., "Carbohydrate triazoles and isoxazoles as inhibitors of galectine-1 and -3", in Chem. Commun., 2006, p. 2379-2381; 3 pages.
Glinsky et al., "Inhibition of Human Breast Cancer Metastasis in Nude Mice by Synthetic Glycoamines", in Cancer Research, vol. 56, Dec. 1, 1996, p. 5319-5324; 6 pages.
Glinsky et al., "Synthetic Galectin-3 Inhibitor Increases Metastatic Cancer Cell Sensitivity to Taxol-Induced Apoptosis In Vitro and In Vivo", in Neoplasia, vol. 11, No. 9, Sep. 2009, p. 901-909; 9 pages.
Huflejt et al., "Galectin-4 in normal tissues and cancer", in Glycoconjugate Journal 20, 2004, p. 247-255; 9 pages.
Ingrassia et al., "A Lactosylated Steroid Contributes in Vivo Therapeutic Benefits in Experimental Models of Mouse Lymphoma and Human Glioblastoma", in J. Med. Chem., vol. 49, 2006, p. 1800-1807; 8 pages.
John et al., "Truncated Galectin-3 Inhibits Tumor Growth and Metastasis in Orthotopic Nude Mouse Model of Human Breast Cancer", in Clinical Cancer Research, vol. 9, Jun. 2003, p. 2374-2383; 10 pages.
Kouo et al., "Galectin-3 Shapes Antitumor Immune Responses by Suppressing CD8 T Cells via LAG-3 and Inhibiting Expansion of Plasmacytoid Dendritic Cells", in Cancer Immunology Research, vol. 3, No. 4, Apr. 2015, p. 412-423; 13 pages.
Lau et al., "N-Glycans in cancer progression", in Glycobiology, vol. 18, No. 10, 2008, p. 750-760; 11 pages.
Lau et al., "Complex N-Glycan Number and Degree of Branching Cooperate to Regulate Cell Proliferation and Differentiation", in Cell 129, Apr. 6, 2007, p. 123-134; 12 pages.
Leffler et al., "Specificity of Binding of Three Soluble Rat Lung Lectins to Substituted and Unsubstituted Mammalian B-Galactosides", in The Journal of Biological Chemistry, vol. 261, No. 22, Aug. 5, 1986, p. 10119-10126; 8 pages.
Leffler, "Galectins Structure and Function—A Synopsis", in Results and Problems in Cell Differentiation, vol. 33, 2001, p. 57-83; 27 pages.
Leffler et al., "Introduction to galectins", in Glycoconjugate Journal 19, 2004, p. 433-440; 8 pages.
Chiariotti et al., "Galectin genes: Regulation of expression", in Glycoconjugate Journal 19, 2004, p. 441-449; 9 pages.
Lin et al., "Galectin-3 Targeted Therapy with a Small Molecule Inhibitor Activates Apoptosis and Enhances Both Chemosensitivity and Radiosensitivity in Papillary Thyroid Cancer", in Mol. Cancer Res., vol. 7, No. 10, Oct. 2009, p. 1655-1662; 8 pages.
Mackinnon et al., "Regulation of Alternative Macrophage Activation by Galectin-3", in The Journal of Immunology, vol. 180, 2008, p. 2650-2658; 9 pages.
Mackinnon et al., "Regulation of Transforming Growth Factor-β1-driven Lung Fibrosis by Galectin-3", in Am. J. Resp. Crit. Care Med., vol. 185, 2012, p. 1-11; 11 pages.

Massa et al., "L-29, an Endogenous Lectin, Binds to Glycoconjugate Ligands with Positive Cooperativity", in Biochemistry, vol. 32, 1993, p. 260-267; 8 pages.
Melero et al., "Evolving synergistic combinations of targeted immunotherapies to combat cancer", in Nature Reviews, vol. 15, Aug. 2015, p. 457-472; 16 pages.
Partridge et al., "Regulation of Cytokine Receptors by Golgi N-Glycan Processing and Endocytosis", in Science, vol. 306, Oct. 1, 2004, p. 120-124; 6 pages.
Perone et al., "Suppression of Autoimmune Diabetes by Soluble Galectin-1", in The Journal of Immunology, vol. 182, Sep. 15, 2017, p. 2641-2653; 14 pages.
Pienta et al., "Inhibition of Spontaneous Metastasis in a Rat Prostate Cancer Model by Oral Administration of Modified Citrus Pectin", in J. Natl. Cancer Inst., vol. 87, No. 5, Mar. 1, 1995, p. 348-353; 6 pages.
Ramos-Soriano et al., "Synthesis, Biological Evaluation, WAC and NMR Studies of S-Galactosides and Non-Carbohydrate Ligands of Cholera Toxin Based on Polyhydroxyalkylfuroate Moieties", in Chem. Eur. J., vol. 19, 2013, p. 17989-18003; 15 pages.
Ruvolo, "Galectin 3 as a guardian of the tumor microenvironment", in Biochimica et Biophysica Acta, Apr. 8 2015; http://dx.doi.org/10.1016/j.bbamcr.2015.08.008; 11 pages.
Saegusa et al., "Galectin-3 is critical for the development of the allergic inflammatory response in a mouse model of atopic dermatitis", in Am J Pathol, vol. 174, No. 3, Mar. 2009, p. 922-931; 10 pages.
Salameh et al., "3-(1,2,3-Triazol-1-yl)-1-thio-galactosides as small, efficient, and hydrolytically stable inhibitors of galectin-3", in Bioorg. Med. Chem. Lett., vol. 15, 2005, p. 3344-3346; 3 pages.
Salameh et al., "1H-1,2,3-Triazol-1-yl thiodigalactoside derivatives as high affinity galectin-3 inhibitors", in Bioorg Med Chem, vol. 18, 2010, p. 5367-5378; 13 pages.
Salomonsson et al., "Monovalent interactions of galectin-1", in Biochemistry, vol. 49, 2010, p. 9518-9532; 15 pages.
Sörme et al., "Low micromolar inhibitors of galectin-3 based on 3'-derivatization of N-acetyllactosamine", in ChemBioChem, vol. 3, 2002, p. 183-189; 7 pages.
Sörme et al., "Fluorescence polarization to study galectin-ligand interactions", in Meth. Enzymol., vol. 362, 2003, p. 504-512; 9 pages.
Sörme et al., "Design and synthesis of galectin inhibitors", in Meth. Enzymol., vol. 363, 2003b, p. 157-169; 13 pages.
Sörme et al., "Fluorescence polarization as an analytical tool to evaluate galectin-ligand interactions", in Anal. Biochem., vol. 334, 2004, p. 36-47; 12 pages.
Thijssen et al., "Galectins in the tumor endothelium: opportunities for combined cancer therapy", in Blood, vol. 110, 2007, p. 2819-2827; 10 pages.
Toscano et al., "Differential glycosylation of TH1, TH2 and TH-17 effector cells selectively regulates susceptibility to cell death", in Nat Immunol, vol. 8, No. 8, Aug. 2007, p. 825-834; 10 pages.
Ogawa et al., "The speciation of conger eel galectins by rapid adaptive evolution", in Glycoconjugate Journal 19, 2004, p. 451-458; 8 pages.
Brewer, "Thermodynamic binding studies of galectin-1, -3 and -7", in Glycoconjugate Journal 19, 2004, p. 459-465; 7 pages.
Scott et al., "Galectin-1: A bifunctional regulator of cellular proliferation", in Glycoconjugate Journal 19, 2004, p. 467-477; 11 pages.
Horie et al., "Galectin-1 plays essential roles in adult mammalian nervous tissues. Roles of oxidized galectin-1", in Glycoconjugate Journal 19, 2004, p. 479-489; 11 pages.
Lipkowitz et al., "Galectin 9 is the sugar-regulated urate transporter/channel UAT", in Glycoconjugate Journal 19, 2004, p. 491-498; 8 pages.
Patterson et al., "Understanding the biochemical activities of galectin-1 and galectin-3 in the nucleus", in Glycoconjugate Journal 19, 2004, p. 499-506; 8 pages.
Hsu et al., "Regulation of cellular homeostasis by galectins", in Glycoconjugate Journal 19, 2004, p. 507-515; 9 pages.
Zick et al., "Role of galectin-8 as a modulator of cell adhesion and cell growth", in Glycoconjugate Journal 19, 2004, p. 517-526; 10 pages.

(56) References Cited

OTHER PUBLICATIONS

Ochieng et al., "Extracellular functions of galectin-3", in Glycoconjugate Journal 19, 2004, p. 527-535; 9 pages.

Brûle et al., "Expression of galectins in cancer: A critical review", in Glycoconjugate Journal 19, 2004, p. 537-542; 6 pages.

Takenaka et al., "Galectin-3 and metastasis", in Glycoconjugate Journal 19, 2004, p. 543-549; 7 pages.

Grassadonia et al., "90K (Mac-2 BP) and galectins in tumor progression and metastasis", in Glycoconjugate Journal 19, 2004, p. 551-556; 6 pages.

Bidon-Wagner et al., "Human galectin-8 isoforms and cancer", in Glycoconjugate Journal 19, 2004, p. 557-563; 7 pages.

Rabinovich et al., "Shedding light on the immunomodulatory properties of galectins: Novel regulators of innate and adaptive immune responses", in Glycoconjugate Journal 19, 2004, p. 565-573; 9 pages.

Almkvist et al., "Galectins as inflammatory mediators", in Glycoconjugate Journal 19, 2004, p. 575-581; 7 pages.

Sato et al., "Seeing strangers or announcing "danger": Galectin-3 in two models of innate immunity", in Glycoconjugate Journal 19, 2004, p. 583-591; 9 pages.

Hirashima et al., "Galectin-9 in physiological and pathological conditions", in Glycoconjugate Journal 19, 2004, p. 593-600; 8 pages.

Young et al., "Galectins in parasite infection and allergic inflammation", in Glycoconjugate Journal 19, 2004, p. 601-606; 6 pages.

Pace et al., "Insect galectins: Roles in immunity and development", in Glycoconjugate Journal 19, 2004, p. 607-614; 8 pages.

Watt et al., "The involvement of galectin-1 in skeletal muscle determination, differentiation and regeneration", in Glycoconjugate Journal 19, 2004, p. 615-619; 5 pages.

Hughes, "Galectins in kidney development", in Glycoconjugate Journal 19, 2004, p. 621-629; 9 pages.

\* cited by examiner

ALPHA-D-GALACTOSIDE INHIBITORS OF GALECTINS

TECHNICAL FIELD

The present invention relates to novel compounds, the use of said compounds as medicament and for the manufacture of a medicament for the treatment of cancers; fibrosis; scarring; keloid formation; aberrant scar formation; surgical adhesions; pathological angiogenesis; eye diseases; HIV-1 diseases; inflammation or transplant rejection in mammals. The invention also relates to pharmaceutical compositions comprising said novel compounds.

BACKGROUND ART

Galectins are proteins with a characteristic carbohydrate recognition domain (CRD) (Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Lepur et al., 2012). These were the first discovered galectins and are abundant in many tissues.

There are now over 5700 publications on galectins in PubMed, with most, as mentioned above, about galectins-1 (>1400) and -3 (>2800). Strong evidence suggests roles for galectins in e.g. inflammation and cancer, and development (Blidner et al., 2015, Ebrahim et al., 2014).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway (as first shown for galectin-1 (Cooper and Barondes, 1991)), with as yet unknown mechanism, but possibly similar to the export of e.g. IL-1 (Leffler et al., 2004; Arthur et al., 2015). Galectins can also function in all these compartments; for galectin-1, solid evidence published in well respected journals support roles in RNA splicing in the nucleus, activation of H-RAS in the cytosol, accumulation around disrupted vesicles, and a variety of extracellular effects on cell signaling and adhesion (Elola et al. 2015, Aits et al., 2015, Blanchard et al., 2016). Other galectins also may act in the cytosol by enhancing apoptosis and regulating the cell cycle and differentiation in certain cells. Most galectins act also extracellularly by cross-linking glycoproteins (e.g. laminin, integrins, and IgE receptors) possibly forming supramolecular ordered arrays (Elola et al., 2015) and may thereby modulate cell adhesion and induce intracellular signals. Related to this, recent years have seen the emergence of a molecular mechanism of these galectin functions involving a formation of microdomains (lattices) within membranes, (Elola et al., 2015) which in turn affects intracellular trafficking and cell surface presentation of glycoprotein receptors. This has been documented in cell culture, in null mutant mice, and animals treated with galectin or galectin inhibitors.

Galectin-1, the first discovered and second most studied galectin, is expressed in all tissues with a certain preference but not exclusive for cells of mesenchymal origin like fibroblasts and lymphocytes. It is involved in the regulation of cell growth, adhesion, signaling, differentiation, development, immune system and host-pathogen interactions (Blanchard et al., 2016). Expression profiles of galectin-1 in the various stages of cancer progression and its role in the tumor microenvironment have been thoroughly reviewed.

Galectin-1 has been implicated in diverse phenomena and, hence, inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Galectin-1 in Immunity and Inflammation

Galectin-1 has been found mainly to have an immunosuppressive and anti-inflammatory role (Elola et al., 2015), although in some cases it may also be proinflammatory. Galectin-1 binds specific glycosylation pattern on T-helper cells to selectively induce apoptosis in activated Th1 and Th17 cells. (Perillo et. al., 1995) (Toscano, M. A. et al., 2007). The immunosuppressive effect of galectin-1 has suggested that galectin-1 itself, might be a potential treatment for autoimmune and other inflammatory conditions. Conversely, inhibiting its immunosuppressive effect in e.g. cancer has also been proposed as a treatment, as described below.

Galectin-1 in Angiogenesis.

Like galectin-3, galectin-1 has been shown to promote angiogenesis under certain circumstances (Hockl et al., 2016) in a way involving its carbohydrate binding activity. Particularly interesting is the observation that it might promote tumor angiogenesis by a pathway parallel to VEGF. Hence, inhibiting galectin-1 may be anti-angiogenic when inhibition based on anti-VEGF fails. The discovery that the anti-angiogenic peptide Anginex (and related compounds) binds to galectin-1 suggested another mechanism for galectin-1 in angiogenesis, but the details remain unclear, Anginex is described as inhibiting galectin-1 activity in some reports, but as enhancing its carbohydrate binding-activities in another.

Galectin-1 in Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of the TGF-ß receptor (Partridge et al., 2004), which in turn regulates alternative macrophage differentiation into M2 macrophages and myofibroblast activation. Galectin-1 has also been suggested to a play a role in fibrosis, including by TGF-ß related mechanism, but the evidence is less clear than for galectin-3.

Hence, also galectin-1 is a good candidate for being an endogenous enhancer of TGF-ß signaling and myofibroblast activation (Kathiriya et al), and galectin-1 inhibitors may be also be useful in treating fibrosis and adverse tissue remodeling.

Galectin-1 in Cancer.

A large number of immunohistochemical studies show changed expression of certain galectins in cancer (van den Brule et. al. and Bidon et al. in Leffler (editor), 2004b) and for example galectin-3 is now an established histochemical marker of thyroid cancer. The direct evidence for a role of galectin-3 in cancer comes from mouse models, mainly by Raz et al, but also others (in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. Further, recent evidence have shown that galectin-3 plays a critical role in the tumor microenvironment—reviewed in (Ruvolo, 2015). Galectin-3 is also believed to regulate the interaction between the tumor cells and immune cells, such as T-lymphocytes (T-cells), and inhibition of galectin-3 has been shown to restore T-cell activity (Demotte et al. 2010, Kouo et al. 2015, Melero et al. 2015). From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Lin et al., 2009), as well as in vivo (Glinsky et al., 2009).

Also galectin-1 is frequently over-expressed in low differentiated cancer cells, and galectin-9 or its relatives galectin-4 and galectin-8 may be induced in specific cancer types (Huflejt and Leffler, 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b). Therefore, the over-expression of these galectins in cancers might help the tumor to defend itself against the T-cell response raised by the host.

Null mutant mice for galectins-1 and -3 have been established many years ago (Poirier, 2002). These are healthy and reproduce apparently normally in animal house conditions. However, recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analyzed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Thus drugs targeting galectin-1 activities in cancer such as suppressing immunity or enhancing angiogenesis may become useful anti-cancer treatments.

Known Inhibitors

Natural Ligands

Solid phase binding assays and inhibition assays have identified a number of saccharides and glycoconjugates with the ability to bind galectins (reviewed by Leffler, 2001, Leffler et al., 2004). All galectins bind lactose with a $K_d$ of about 0.1-1 mM. The affinity of D-galactose is 50-100 times lower. N-Acetyllactosamine and related disaccharides bind about as well as lactose, but for certain galectins, they can bind either worse or up to 10 times better. Galactose (10 mM) (Tejler et. al. 2009) and Lactose (190 µM) (van Hattum, 2013) both have low affinity to Galectin-1.

The above-described natural saccharides that have been identified as galectin-1 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

A patent review covering galectin-1 inhibitors and their potential as therapeutics were recently published. (Blanchard 2016). The small molecule monosaccharides covered in this review have been reported as having galectin-1 affinity which is at best similar to lactose. Disaccharides on the other hand, in particular thiodigalactosides (TDG), has been reported to have high affinity towards galectin-1. (T. Delaine, 2016, ChemBioChem 10.1002/cbic.201600285)

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. Chlorinconjugatcd lactose have been reported to have high affinity (0.54 µM) as measured in an Elisa assay. (Pandey et. al. 2002, in EP1256586 (A1)). A chemically modified form of citrus pectin (Platt and Raz, 1992) that inhibits galectin-3 shows anti-tumor activity in vivo (Pienta et al., 1995; Nangia-Makker et al., 2002). Cluster molecules having up to four lactose moieties showed a strong multivalency effect when binding to galectin-3, but not to galectin-1 and galectin-5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. Multivalent lactose derivatives have been shown to have a pronounced cluster effect towards galectin-1 (Tejler et. al., 2006). In addition, these compounds were selective over other galectins. Peptide based compounds such as Anginex and non-peptidic topomimetics (Dings et. al. 2012) have been reported to be allosteric galectin-1 inhibitors. The aforementioned synthetic compounds that have been identified as galectin-1 ligands are not suitable for use as active components in pharmaceutical compositions, because they are hydrophilic in nature and are not readily absorbed from the gastrointestinal tract following oral administration. In addition the aforementioned compounds have moderate affinity and selectivity.

Natural oligosaccharides, glycoclusters, glycodendrimers, peptides, non-peptidic topomimetics and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules.

Thiodigalactoside is known to be a synthetic and hydrolytically stable, yet polar inhibitor, approximately as efficient as N-acetyllactosamine (Leffler and Barondes, 1986). N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 µM, which is a 20-fold improvement in comparison with the natural N-acetyllactosamine disaccharide (Sörme et al., 2002; Sörme et al., 2003b, 2005). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/113569 and US2007185041; WO/2005/113568, U.S. Pat. No. 7,638,623 B2; T. Delaine, 2016, ChemBioChem 10.1002/cbic.201600285) which lack O-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

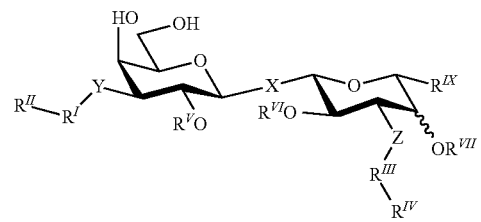

as described in WO/2005/113568,
and

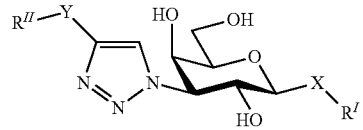

as described in WO/2005/113569, in which $R^1$ can be a D-galactose.

In recently published (T. Delaine, 2016, ChemBioChem 10.1002/cbic.201600285) is disclosed a

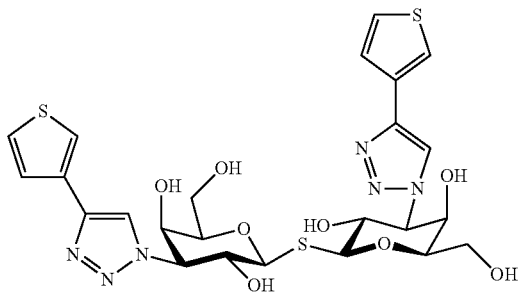

TDG substituted with a thiophene triazole substituent in the C3 and C3' positions with high affinity (<10 nM) to Galectin-1.

In recently published US20140099319, WO2014067986 and T. Delaine, 2016, ChemBioChem 10.1002/cbic.201600285, is disclosed a compound

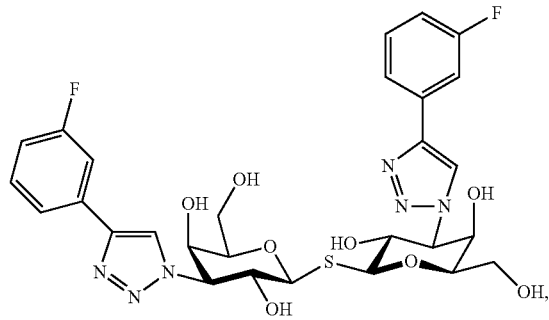

having fluorine (F) in the meta position on both the phenyl rings in relation to the triazole rings. This compound has been shown to be a promising drug candidate for lung fibrosis, and in particular is very selective on galectin-3 with high affinity.

A series of small C1 or C1 and C3-substituted galactopyranosides have been disclosed showing affinity towards galectin-3 and 1. The beta-D-galactopyranosides were reported as having affinity in the same range or less than lactose, which has a Kd of about 91 µM towards galectin 3 and 190 µM towards galectin 1. (Giguere, D et. al. 2011, 2008, 2006).

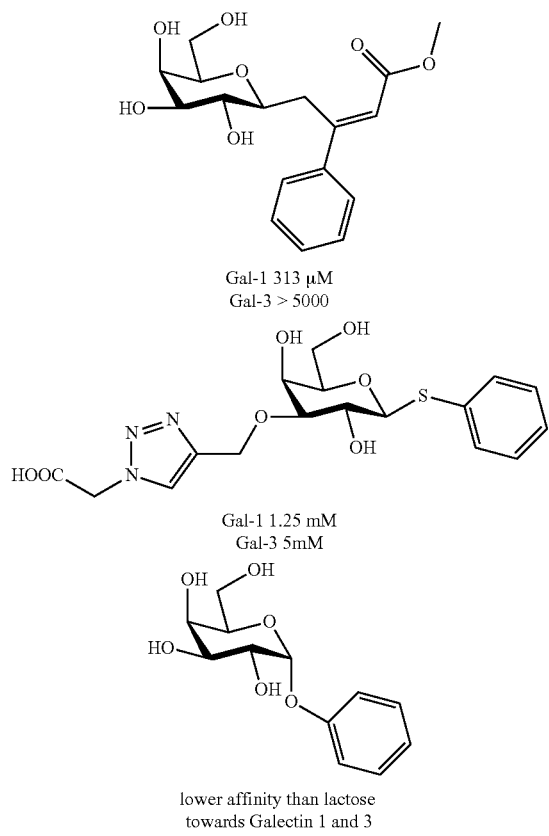

There is no disclosure or mentioning of corresponding alpha-anomers having affinity towards galectin-1 or galectin-3 better than lactose.

SUMMARY OF THE INVENTION

The compounds of the present invention are novel α-D-galactopyranose compounds that unexpectedly have shown high affinity and selectivity for galectin-1, and are considered novel potent drug candidates. Some of these compounds have very good PK properties for e.g. oral administration, such as low clearance and high bioavailability.

In broad aspect the present invention concerns a D-galactopyranose compound of formula (1)

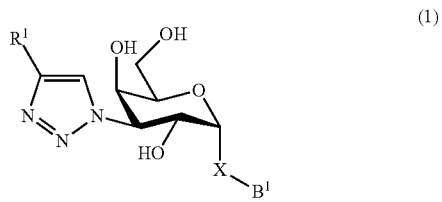

wherein the pyranose ring is α-D-galactopyranose, $R^1$ is a five or six membered heteroaromatic ring selected from the group consisting of formulas 2 to 9, wherein the asterix * indicates the carbon atom of the heteroaromatic ring that is covalently attached to the triazole group of formula (1):

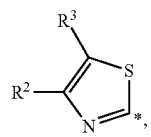

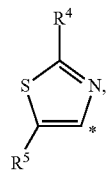

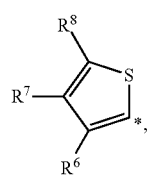

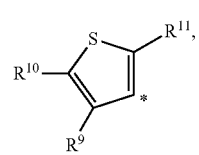

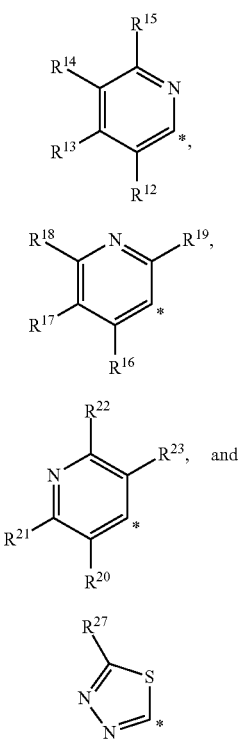

wherein R² to R²³ and R²⁷ are independently selected from H; halogen; OH; CN; SH; S—$C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; $OC_{1-3}$ alkyl optionally substituted with a F; $NR^{24}R^{25}$, wherein $R^{24}$ is selected from H, and $C_{1-3}$ alkyl, and $R^{25}$ is selected from H, $C_{1-3}$ alkyl, and $COR^{26}$, wherein $R^{26}$ is selected from H, and $C_{1-3}$ alkyl;

X is selected from S, SO, $SO_2$;

B¹ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and $R^{27}$—CONH— wherein $R^{27}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and $R^{28}$—CONH— wherein $R^{28}$ is selected from $C_{1-3}$ alkyl and cyclopropyl; b) an aryl, such as phenyl or naphthyl, optionally substituted with a group selected from a halogen; CN; —COOH; —$CONR^{29}R^{30}$, wherein $R^{29}$ and $R^{30}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclpropyl, optionally substituted with a F; O-isopropyl, optionally substituted with a F; $NR^{31}R^{32}$, wherein $R^{31}$ and $R^{32}$ are independently selected from H, $C_{1-3}$ alkyl and isopropyl; OH; and $R^{33}$—CONH—, wherein $R^{33}$ is selected from $C_{1-3}$ alkyl and cyclopropyl; c) a $C_{5-7}$ cycloalkyl, optionally substituted with a substituent selected from a halogen, CN, methyl optionally substituted with a F, $OCH_3$ optionally substituted with a F, $OCH_2CH_3$ optionally substituted with a F, OH, and $R^{34}$—CONH— wherein $R^{34}$ is selected from $C_{1-3}$ alkyl and cyclopropyl; and d) a heterocycle, such as heteroaryl or heterocycloalkyl, optionally substituted with a group selected from a halogen; CN; —COOH; —$CONR^{35}R^{36}$, wherein $R^{35}$ and $R^{36}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{37}R^{38}$, wherein $R^{37}$ and $R^{38}$ are independently selected from H, $C_{1-3}$ alkyl and isopropyl; OH; and $R^{39}$—CONH— wherein $R^{39}$ is selected from $C_{1-3}$ alkyl and cyclopropyl; e) a $C_{1-6}$ alkyl or branched $C_{3-6}$ alkyl; or a pharmaceutically acceptable salt or solvate thereof.

In an embodiment $R^1$ is selected from a five or six membered heteroaromatic ring selected from the group consisting of formulas 2, 3, 4, 5, and 9, wherein the remaining substituents are as defined above. In a further embodiment $R^1$ is selected from a five or six membered heteroaromatic ring selected from the group consisting of formulas 2, 3, 4, and 5, wherein the remaining substituents are as defined above.

In an embodiment $R^1$ is selected from formula 2 wherein $R^2$ and $R^3$ are independently selected from H, halogen, and $C_{1-3}$ alkyl, optionally substituted with a F, typically both are H. In another embodiment $R^1$ is selected from formula 2 wherein $R^2$ and $R^3$ are independently selected from H, halogen, and $C_{1-3}$ alkyl. In a further embodiment $R^1$ is selected from formula 3 wherein $R^4$ and $R^5$ are independently selected from H, halogen, and $C_{1-3}$ alkyl, typically both are H or methyl, or $R^4$ is methyl and $R^5$ is H. In a further embodiment $R^1$ is selected from formula 4 wherein $R^6$-$R^8$ are independently selected from H, halogen, and $C_{1-3}$ alkyl, typically $R^6$-$R^8$ are all H, or $R^8$ is halogen, such as F, and $R^6$ and $R^7$ are both H. In a further embodiment $R^1$ is selected from formula 5 wherein $R^9$-$R^{11}$ are independently selected from H, halogen, and $C_{1-3}$ alkyl, typically $R^9$-$R^{11}$ are all H. In a further embodiment $R^1$ is selected from formula 6 wherein $R^{12}$-$R^{15}$ are independently selected from H, halogen, and $C_{1-3}$ alkyl, typically $R^{12}$-$R^{15}$ are all H, or $R^{14}$ is halogen, such as F, and $R^{12}$, $R^{13}$ and $R^{15}$ are all H. In a further embodiment $R^1$ is selected from formula 7 wherein $R^{16}$-$R^{19}$ are independently selected from H, halogen, and $C_{1-3}$ alkyl. In a further embodiment $R^1$ is selected from formula 8 wherein $R^{20}$-$R^{23}$ are independently selected from H, halogen, and $C_{1-3}$ alkyl. In a further embodiment $R^1$ is selected from formula 9 wherein $R^{27}$ is selected from H, halogen, and $C_{1-3}$ alkyl, such as H.

In a further embodiment X is selected from S.

In a still further embodiment B¹ is selected from an aryl, such as phenyl or naphthyl, optionally substituted with a group selected from halogen; CN; and methyl optionally substituted with a F. In a further embodiment B¹ is selected from a phenyl or phenyl substituted with one, two or three substituents selected from Cl, F, Br, CN, and $CF_3$. In a still further embodiment B¹ is selected from a heterocycle, such as heteroaryl or heterocycloalkyl, optionally substituted with a group selected from a halogen; CN; and a methyl optionally substituted with a F. In a still further embodiment B¹ is selected from a heterocycle, such as heteroaryl or heterocycloalkyl, optionally substituted with a group selected from a halogen; and a methyl optionally substituted with a F. In a still further embodiment B¹ is selected from a pyridinyl, optionally substituted with a group selected from a halogen, CN, and a methyl optionally substituted with a F. In a still further embodiment B¹ is selected from a pyridinyl, optionally substituted with a group selected from a halogen, and a methyl optionally substituted with a F. In a still further embodiment B¹ is selected from a pyridinyl, optionally substituted with one, or two substituents selected from Cl, Br, CN and CF₃. In a still further embodiment B¹ is selected from a pyridinyl, optionally substituted with one, or two substituents selected from Br and CF₃.

In a further embodiment the compound of the present invention selected from:

3,4-Dichlorophenyl 3-deoxy-3-[4-(3-thiophenyl)-1H-1,2,3-triazol-1-yl]-1-thio-α-D-galactopyranoside,
2-Chloro-5-fluoro-benzonitril-4-yl 3-deoxy-3-[4-(3-thiophenyl)-1H-1,2,3-triazol-1-yl]-1-thio-α-D-galactopyranoside,
5-Bromopyridin-3-yl 3-deoxy-3-[4-(3-thiophenyl)-1H-1,2,3-triazol-1-yl]-1-thio-α-D-galactopyranoside,
5-Bromo-6-trifluoromethyl-pyridin-3-yl 3-deoxy-3-[4-(3-thiophenyl)-1H-1,2,3-triazol-1-yl]-1-thio-α-D-galactopyranoside,
3,5-Dichloro-4-fluoro-phenyl 3-deoxy-3-[4-(3-thiazolyl)-1H-1,2,3-triazol-1-yl]-1-thio-α-D-galactopyranoside,
3,4-Dichlorophenyl 3-deoxy-3-[4-(5-fluoro-2-pyridyl)-1H-1,2,3-triazol-1-yl]-1-thio-α-D-galactopyranoside,
5-Bromopyridin-3-yl 3-deoxy-3-[4-(2-thiophenyl)-1H-1,2,3-triazol-1-yl]-1-thio-α-D-galactopyranoside,
3,5-Dichloro-4-fluoro-phenyl 3-deoxy-3-[4-(2-thiophenyl)-1H-1,2,3-triazol-1-yl]-1-thio-α-D-galactopyranoside,
3,4-Dichlorophenyl 3-deoxy-3-[4-(5-fluoro-2-thiophenyl)-1H-1,2,3-triazol-1-yl]-1-thio-α-D-galactopyranoside,
5-Bromopyridin-3-yl 3-deoxy-3-[4-(4-thiazolyl)-1H-1,2,3-triazol-1l-yl]-1-thio-α-D-galactopyranoside,
5-Bromo-6-trifluoromethyl-pyridin-3-yl 3-deoxy-3-[4-(4-thiazolyl)-1H-1,2,3-triazol-1-yl]-1-thio-α-D-galactopyranoside,
3,4-Dichlorophenyl 3-deoxy-3-[4-(4-thiazolyl)-1H-1,2,3-triazol-1-yl]-1-thio-α-D-galactopyranoside,
2-Chloro-benzonitril-4-yl 3-deoxy-3-[4-(4-thiazolyl)-1H-1,2,3-triazol-1-yl]-1-thio-α-D-galactopyranoside,
3,5-Dichloro-4-fluoro-phenyl 3-deoxy-3-[4-(4-thiazolyl)-1H-1,2,3-triazol-1-yl]-1-thio-α-D-galactopyranoside,
5-Bromopyridin-3-yl 3-deoxy-3-[4-(2-methyl-4-thiazolyl)-1H-1,2,3-triazol-1-yl]-1-thio-α-D-galactopyranoside,
2,6-Dichloro-bensonitril-4-yl 3-deoxy-3-[4-(2-thiazolyl)-1H-1,2,3-triazol-1-yl]-1-thio-α-D-galactopyranoside,
3,4,5-Trichlorophenyl 3-deoxy-3-[4-(2-thiazolyl)-1H-1,2,3-triazol-1-yl]-1-thio-α-D-galactopyranoside,
3,4-Dichlorophenyl 3-deoxy-3-[4-(2-thiazolyl)-1H-1,2,3-triazol-1-yl]-1-thio-α-D-galactopyranoside, and
3,4,5-Trichlorophenyl 3-deoxy-3-[4-(1,3,4-thiadiazol-2-yl)-1H-1,2,3-triazol-1-yl]-1-thio-α-D-galactopyranoside.

In a further embodiment the compound of the present invention is selected from:

5-Bromopyridin-3-yl 3-deoxy-3-[4-(2-thiazolyl)-1H-1,2,3-triazol-1-yl]-1-thio-α-D-galactopyranoside,
5-Chloropyridin-3-yl 3-deoxy-3-[4-(2-thiazolyl)-1H-1,2,3-triazol-1-yl]-1-thio-α-D-galactopyranoside,
5-Bromo-2-cyano-pyridine-3-yl 3-deoxy-3-[4-(2-thiazolyl)-1H-1,2,3-triazol-1-yl]-1-thio-α-D-galactopyranoside,
5-Chloro-6-cyano-pyridine-3-yl 3-deoxy-3-[4-(2-thiazolyl)-1H-1,2,3-triazol-1-yl]-1-thio-α-D-galactopyranoside,
3,5-Dichlorophenyl 3-deoxy-3-[4-(2-thiazolyl)-1H-1,2,3-triazol-1-yl]-1-thio-α-D-galactopyranoside
3-Bromo-4-chlorophenyl 3-deoxy-3-[4-(2-thiazolyl)-1H-1,2,3-triazol-1-yl]-1-thio-α-D-galactopyranoside,
5-Bromo-6-trifluoromethyl-pyridine-3-yl 3-deoxy-3-[4-(2-thiazolyl)-1H-1,2,3-triazol-1-yl]-1-thio-α-D-galactopyranoside,
3-Bromo-4-fluoro-phenyl 3-deoxy-3-[4-(2-thiazolyl)-1H-1,2,3-triazol-1-yl]-1-thio-α-D-galactopyranoside,
2,5-Dichlorophenyl 3-deoxy-3-[4-(2-thiazolyl)-1H-1,2,3-triazol-1-yl]-1-thio-α-D-galactopyranoside,
3,4-Dichlorophenyl 3-deoxy-3-[4-(4-bromo-thiazol-2-yl)-1H-1,2,3-triazol-1-yl]-1-thio-α-D-galactopyranoside,
3,4-Dichlorophenyl 3-deoxy-3-[4-(5-fluoro-thiazol-2-yl)-1H-1,2,3-triazol-1-yl]-1-thio-α-D-galactopyranoside,
3,4-Dichlorophenyl 3-deoxy-3-[4-(4-chloro-thiazol-2-yl)-1H-1,2,3-triazol-1-yl]-1-thio-α-D-galactopyranoside,
3,4-Dichlorophenyl 3-deoxy-3-[4-(4-trifluoromethyl-thiazol-2-yl)-1H-1,2,3-triazol-1-yl]-1-thio-α-D-galactopyranoside.

In a further aspect the present invention relates to a compound of formula (i) for use as a medicine.

In a still further aspect the present invention relates to a pharmaceutical composition comprising the compound of any one of the previous claims and optionally a pharmaceutically acceptable additive, such as a carrier and/or excipient.

In a further aspect the present invention relates to a compound of formula (1) of the present invention for use in a method for treating a disorder relating to the binding of a galectin-1 to a ligand in a mammal, such as a human. In a further embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; scleroderma; sclerosis; surgical adhesions; septic shock; cancer, such as carcinomas, sarcomas, leukemias and lymphomas, such as T-cell lymphomas; metastasising cancers; neovascularization related to cancer; autoimmune diseases, such as psoriasis, rheumatoid arthritis, Crohn's disease, ulcerative colitis, ankylosing spondylitis, systemic lupus erythematosus; transplant rejection; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; obesity; asthma and other interstitial lung diseases, including Hermansky-Pudlak syndrome, mesothelioma; liver disorders, such as non-alcoholic steatohepatitis.

In a still further aspect the present invention relates to a method for treatment of a disorder relating to the binding of a galectin-1 to a ligand in a mammal, such as a human, wherein a therapeutically effective amount of at least one compound of formula (1) of the present invention is administered to a mammal in need of said treatment. In a further embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; scleroderma; sclerosis; surgical adhesions; septic shock; cancer, such as carcinomas, sarcomas, leukemias and lymphomas, such as T-cell lymphomas; metastasising cancers; neovascularization related to cancer, autoimmune diseases, such as psoriasis, rheumatoid arthritis, Crohn's disease, ulcerative colitis, ankylosing spondylitis, systemic lupus erythematosus; transplant rejection; metabolic disorders; heart disease; heart failure; pathological angiogenesis, such as ocular angiogenesis or a disease or condition associated with ocular angiogenesis, e.g. neovascularization related to cancer, and eye diseases, such as age-related macular degeneration and corneal neovascularization; atherosclerosis; metabolic diseases such as diabetes; obesity; asthma and other interstitial lung diseases, including Hermansky-Pudlak syndrome, mesothelioma; liver disorders, such as non-alcoholic steatohepatitis.

As mentioned above some of the compounds of the present invention have high galectin-1 affinity and very good PK properties, showing high oral bioavailability and are suitable for oral administration, and the data presented herein supports that at least the compounds of formula (1) of the present invention wherein; have these very good PK properties and high galectin-1 affinity.

Another aspect of the present invention concerns combination therapy involving administering a compound of formula (1) of the present invention together with a therapeutically active compound different from the compound of formula (1) (interchangeable with "a different therapeutically active compound"). In one embodiment, the present invention relates to a combination of a compound of formula (1) and a different therapeutically active compound for use in treatment of a disorder relating to the binding of a galectin-1 to a ligand in a mammal. Such disorders are disclosed below.

In an embodiment of the present invention, a therapeutically effective amount of at least one compound of formula (1) of the present invention is administered to a mammal in need thereof in combination with a different therapeutically active compound. In a further embodiment, said combination of a compound of formula (1) together with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; scleroderma; sclerosis; surgical adhesions; septic shock; cancer, such as carcinomas, sarcomas, leukemias and lymphomas, such as T-cell lymphomas; metastasising cancers; neovascularization related to cancer; autoimmune diseases, such as psoriasis, rheumatoid arthritis, Crohn's disease, ulcerative colitis, ankylosing spondylitis, systemic lupus erythematosus; transplant rejection; metabolic disorders; heart disease; heart failure; pathological angiogenesis, such as ocular angiogenesis or a disease or condition associated with ocular angiogenesis, e.g. neovascularization related to cancer, and eye diseases, such as age-related macular degeneration and corneal neovascularization; atherosclerosis; metabolic diseases such as diabetes; obesity; asthma and other interstitial lung diseases, including Hermansky-Pudlak syndrome, mesothelioma; liver disorders, such as non-alcoholic steatohepatitis.

A non-limiting group of cancers given as examples of cancers that may be treated, managed and/or prevented by administration of a compound of formula (1) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, cholangiocarcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myclomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In some aspects of the present invention, the administration of at least one compound of formula (1) of the present invention and at least one additional therapeutic agent demonstrates therapeutic synergy. In some aspects of the methods of the present invention, a measurement of response to treatment observed after administering both at least one compound of formula (1) of the present invention and the additional therapeutic agent is improved over the same measurement of response to treatment observed after administering either the at least one compound of formula (1) of the present invention or the additional therapeutic agent alone.

A further aspect of the present invention concerns combination therapy involving administering a compound of formula (1) of the present invention together with an anti-fibrotic compound different form the compound of formula (1) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, and PBI-4050.

A still further aspect of the present invention concerns combination therapy involving administering a compound of formula (1) in combination with a further conventional cancer treatment such as chemotherapy or radiotherapy, or treatment with immunostimulating substances, gene therapy, treatment with antibodies, vaccines and cellular therapies including eg dendritic cells, haematopoetic stem cells and adoptive T cell transfer, to a mammal in need thereof.

In an embodiment, the compound of formula (1) is administered together with at least one additional therapeutic agent selected from an antineoplastic chemotherapy agent. In a further embodiment, the antineoplastic chemotherapeutic agent is selected from: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In some embodiments of the present invention the compound of formula (1) is administered together with at least one additional therapeutic agent selected from the class of immune checkpoint inhibitors*. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITR, OX40, CD137, CD40, IDO, and TDO. These are known targets and some of these targets are described in Melero et al., Nature Reviews Cancer (2015).

In some embodiments of the present invention the compound of formula (1) is administered together with at least one additional therapeutic agent selected from an inhibitor of indoleamine-2,3-dioxygenase (IDO).

In some embodiments of the present invention the compound of formula (1) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (1) is administered together with at least one additional therapeutic agent selected from one or more inhibitors of the PD-1/PD-L pathway. In some embodiments, the one or more inhibitors of the PD-1/PD-L pathway are selected from one or more antibodies against PD-1, PD-L1, and/or PD-L2.

In a still further aspect the present invention relates to a process of preparing a compound of formula III or a pharmaceutically acceptable salt or solvate thereof comprising the step a1 where X, B and $R^1$ are defined as above under formula 1;

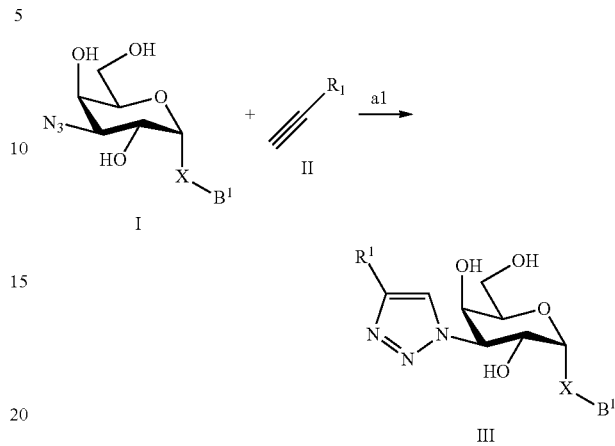

a1) Reacting the compound of formula I with a compound of formula II in an inert solvent, such as DMF or acetonitrile, using a base, such as diisopropylethylamine, catalyzed by CuI to provide the compound of the formula III.

In a still further aspect the present invention relates to a process of preparing a compound of formula V or a pharmaceutically acceptable salt or solvate thereof comprising the step a1 where X, $B^1$, $R^4$ and $R^5$ are defined as above under formula 1;

a2) Reacting a compound of formula IV wherein Z is a leaving group such as a halide or a sulfonate ester with a compound of the formula $R^5$—C(=S)NH$_2$ in the presence of silver trifluoromethanesulfonate in an inert solvent such as ethyl acetate to provide a compound of the formula V.

In a still further aspect the present invention relates to a process of preparing a compound of formula VII and/or VIII or a pharmaceutically acceptable salt or solvate thereof comprising the step a3 where B and $R^1$ are defined as above under formula 1;

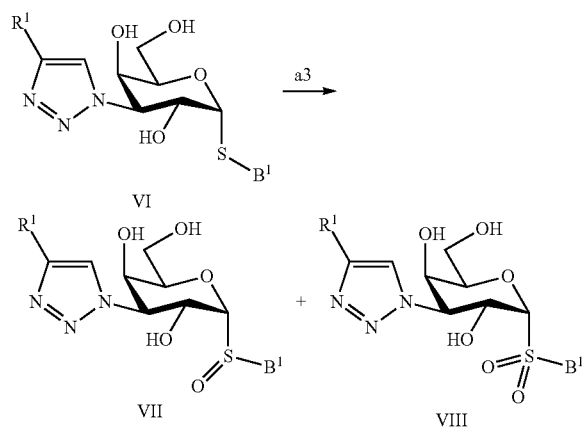

a3) reacting a compound of formula VI with an oxidant such as hydrogen peroxide in a solvent such as acetic acid, alternatively 3-chloroperoxybenzoic acid in an inert solvent such as dichloromethane to give a compound of formula VII and/or VIII.

In a still further aspect the present invention relates to a process of preparing a compound of formula XII or a pharmaceutically acceptable salt or solvate thereof comprising the steps a4 and a5;

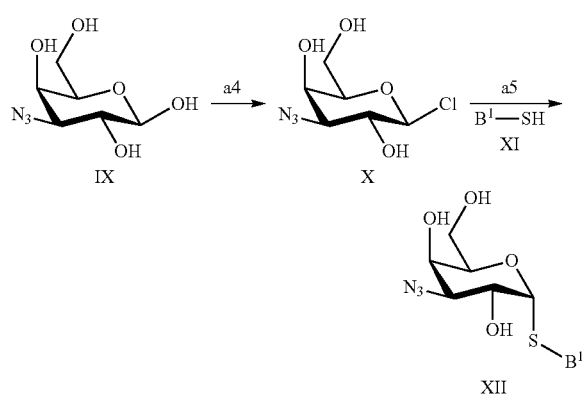

a4) Reacting a compound IX with a chlorinating reagent such as dichloromethylmethylether or $PCl_5$ in the presence of a lewis acid such as $BF_3Et_2O$ in an inert solvent such as dichloromethane or chloroform to give a compound of formula X.

a5) Reacting a compound of the formula X with a nucleophile like XI in the presence of a base like sodium hydride in an inert solvent such as DMF to give a compound of formula XII.

In a still further aspect the present invention relates to a process of preparing a compound of the formula XI comprising step a6-a7, wherein $B^1$ is defined as above under formula (1);

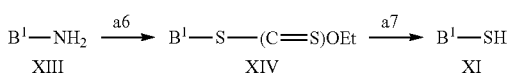

a6) A compound of the formula XIII could upon treatment with sodium nitrite form the corresponding diazocompound. This compound could be further reacted with a sulfurus source such as potassium ethyl xantogenate to form a compound of the formula XIV.

a7) Reacting a compound of formula XIV with a base such as potassium hydroxide to give a compound of formula XI.

In a still further aspect the present invention relates to a process of preparing a compound of the formula XI comprising step a8, wherein $B^1$ is defined as above under formula (1);

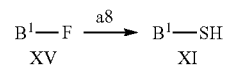

a8) Reacting a compound of the formula XV with $Na_2S*10H_2O$ in the presence of a base such as NaOH in an inert solvent such as DMF to give a compound of formula XI.

In a still further aspect the present invention relates to a process of preparing a compound of the formula XI comprising step a9-a11, wherein $B^1$ is defined as above under formula (1);

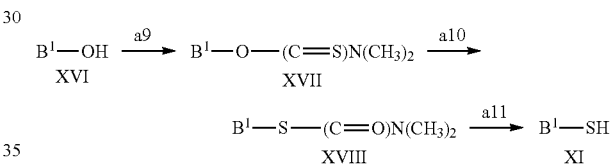

a9) Reacting a compound of the formula XVI with an activated thioamide such as dimethylcarbamoyl chloride using a base such as sodium hydride in an inert solvent such as DMF to give a compound of formula XVII.

a10) Heating a compound of the formula XVII at elevated temperatures to form compound XVIII.

a11) Reacting a compound of formula XVIII with a base such as potassium hydroxide to give a compound of the formula XI.

In a still further aspect the present invention relates to a process of preparing a compound of formula XX comprising the step a12 wherein $R^1$ is defined as above under formula (1):

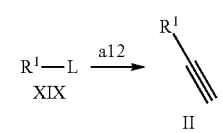

a12) Reacting a compound of formula XIX wherein L is defined as a leaving group such as bromine with trimethylsilane-acetylene using a palladium catalyst such as bis(triphenylphosphine)palladium-(II)-chloride, copper iodide and a base like diisopropylethylamine in an inert solvent, such as tetrahydrofuran (THF), to give a compound of formula II.

In a still further aspect the present invention relates to a process of preparing a compound of the formula IV comprising step a13-a15, wherein $B^1$, X and $R^4$ are defined as above under formula (1);

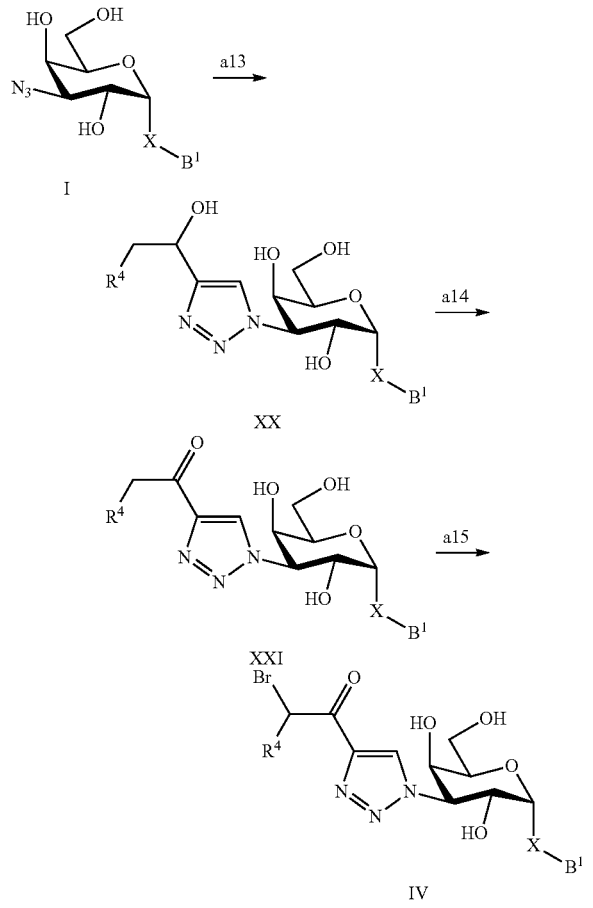

a13) Reacting a compound of formula I with a compound of formula $R^4$—CH$_2$CHOH—CC—H to give a compound of formula XX, using CuI in an inert solvent such as DMF or acetonitrile, using a base, such as diisopropylethylamine.

a14) Reacting a compound of formula XX with an oxidizing reagent such as Dess-Martin periodinane in an inert solvent such as DCM to give a compound of formula XXI.

a15) Introduction of bromine by reacting a compound of the formula XXI first with TBSOTf in the presence of a base such as TEA in an inert solvent such as DCM, to give an intermediate which is further reacted with NBS in an inert solvent such as THF to give a compound of formula IV.

In a still further aspect the present invention relates to a process of preparing a compound of the formula XXIII comprising step a16;

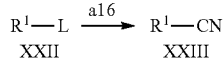

a16) Reacting a compound of the formula XXII, wherein $B^1$ is defined as above and L is a leaving group such as Bromine, with CuCN in an inert solvent such as dimethylformamide (DMF), optionally at elevated temperatures, to give a compound of formula XXIII.

In a still further aspect the present invention relates to a process of preparing a compound of the formula XXV comprising step a17;

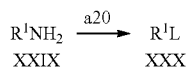

a17) Reacting a compound of the formula XXIV, wherein $B^1$ is defined as above and L is a leaving group such as Iodine, with KF and CuI, optionally at elevated temperatures to give an intermediate which is further reacted with trimethyl (trifluoromethyl)silane to give an intermediate which is dissolved in an inert solvent such as 1-Methyl-2-pyrrolidinone (NMP) and added 3,5-dichloro-2-iodopyridine to give a compound of formula XXV.

In a still further aspect the present invention relates to a process of preparing a compound of the formula XXVIII comprising step a18-a19;

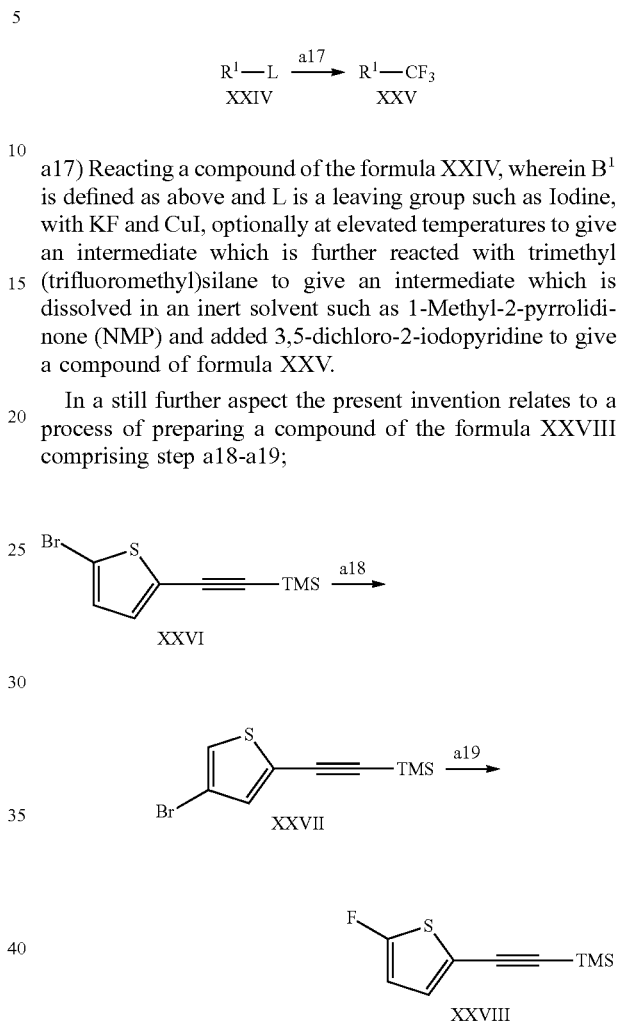

a18) Reacting a compound of the formula XXVI with Lithium diisopropylamine (LDA) in an inert solvent to give compound XXVII. Optionally at low temperatures.

a19) Reacting a compound of the formula XXVII with n-Butyllithium to give an intermediate which is further reacted with N-Fluorobenzenesulfonimide in an inert solvent, optionally at low temperatures, to give a compound of formula XXVIII.

In a still further aspect the present invention relates to a process of preparing a compound of the formula XXX comprising step a20;

$$R^1NH_2 \xrightarrow{a20} R^1L$$
$$\text{XXIX} \quad\quad \text{XXX}$$

a20) Reacting a compound of the formula XXIX wherein $R^1$ is defined as above with with isoamylnitrite followed by reaction with CuL, wherein L is defined as a halogen like chlorine or bromine to give a compound of formula XXX.

In a still further aspect the present invention relates to a process of preparing a compound of the formula XXXII comprising step a21;

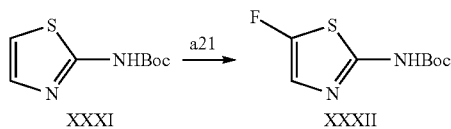

a21) Reacting a compound of formula XXXI with an alkyl lithium such as butyllithium followed by fluorination reagent such as N-fluorobenzene-sulfonylimide to give a compound of the formula XXXII.

DETAILED DESCRIPTION OF THE INVENTION

The present compounds of formula (1) differ from prior art compounds in particular in that the pyranose ring is α-D-galactopyranose. It is important to emphasize that alpha and beta anomers are very different isomers and it is by no means considered to be obvious to the skilled person to expect same or similar activity of both anomers. Consequently alpha and beta anomers do not in general posses the same activity, and this is common knowledge to the skilled person. The compounds of the present invention are novel α-D-galactopyranose compounds that unexpectedly have shown very high affinity for galectin-1, and are considered novel potent drug candidates. Some of these compounds have very good PK properties for e.g. oral administration, such as low clearance and high bioavailability.

In a broad aspect, the present invention concerns a compound of the above formula (1) wherein $R^1$, X and $B^1$ are as defined. Below are described further embodiments.

In an embodiment $R^1$ is selected from formula 2 wherein $R^2$ and $R^3$ are independently selected from H, halogen, and $C_{1-3}$ alkyl. In a further embodiment $R^2$ and $R^3$ are H. In a further embodiment $R^1$ is selected from formula 2 wherein $R^2$ is H and $R^1$ is selected from a halogen, such as F. In a further embodiment $R^1$ is selected from formula 2 wherein $R^2$ is selected from a halogen and $C_{1-3}$ alkyl, optionally substituted with a F and $R^3$ is selected from H. Typically, $R^1$ is selected from formula 2 wherein $R^2$ is selected from Cl, F, Br and $CF_3$ and $R^3$ is selected from H.

In another embodiment $R^1$ is selected from formula 3 wherein $R^4$ and $R^5$ are independently selected from H, halogen, and $C_{1-3}$ alkyl. In a further embodiment $R^4$ and $R^5$ are H. In a still further embodiment $R^4$ is $C_{1-3}$ alkyl and $R^5$ is H. In a particular embodiment $R^4$ is methyl and $R^5$ is H.

In a further embodiment $R^1$ is selected from formula 4 wherein $R^6$-$R^8$ are independently selected from H, halogen, and $C_{1-3}$ alkyl. In a further embodiment $R^6$-$R^8$ are all H. In a still further embodiment $R^8$ is halogen and $R^6$ and $R^7$ are both H. In a particular embodiment $R^8$ is F and $R^6$ and $R^7$ are both H.

In a further embodiment $R^1$ is selected from formula 5 wherein $R^9$-$R^{15}$ are independently selected from H, halogen, and $C_{1-3}$ alkyl. In a further embodiment $R^9$-$R^{11}$ are all H.

In a further embodiment $R^1$ is selected from formula 6 wherein $R^{12}$-$R^{15}$ are independently selected from H, halogen, and $C_{1-3}$ alkyl. In a further embodiment $R^{14}$ is halogen and $R^{12}$, $R^{13}$ and $R^{15}$ are all H. In a particular embodiment $R^{14}$ is F and $R^{12}$, $R^1$ and $R^5$ are all H.

In a further embodiment $R^1$ is selected from formula 9 wherein $R^{27}$ is selected from H, halogen, and $C_{1-3}$ alkyl. In a particular embodiment $R^{27}$ is selected from H.

In a further embodiment X is selected from S.

In a still further embodiment $B^1$ is selected from an aryl, such as phenyl or naphthyl, optionally substituted with a group selected from halogen; CN; and methyl optionally substituted with a F.

In a further embodiment $B^1$ is selected from a phenyl or phenyl substituted with one, two or three substituents selected from Cl, F, Br, CN, and $CF_3$. In a further embodiment $B^1$ is selected from a phenyl substituted with two substituents selected from Cl and CN. In a further embodiment $B^1$ is selected from a phenyl substituted with two substituents selected from Cl, Br and F. In a further embodiment $B^1$ is selected from a phenyl substituted with two substituents selected from Cl. In a further embodiment $B^1$ is selected from a phenyl substituted with two substituents wherein one is Cl and the other is Br. In a further embodiment $B^1$ is selected from a phenyl substituted with two substituents wherein one is F and the other is Br. In a further embodiment $B^1$ is selected from a phenyl substituted with three substituents selected from Cl, F, and CN. Typically, $B^1$ is selected from a phenyl substituted with three substituents selected from a group consisting of 3 Cl; 2 Cl and 1 CN; 2 Cl and 1 F; and 1 Cl, 1 F, and 1 CN.

In a still further embodiment $B^1$ is selected from a heterocycle, such as heteroaryl or heterocycloalkyl, optionally substituted with a group selected from a halogen; CN; and a methyl optionally substituted with a F.

In a still further embodiment $B^1$ is selected from a heterocycle, such as heteroaryl or heterocycloalkyl, optionally substituted with a group selected from a halogen; and a methyl optionally substituted with a F.

In a still further embodiment $B^1$ is selected from a pyridinyl, optionally substituted with a group selected from a halogen, CN, and a methyl optionally substituted with a F. In a still further embodiment $B^1$ is selected from a pyridinyl, optionally substituted with a group selected from a halogen, and a methyl optionally substituted with a F. In a still further embodiment $B^1$ is selected from a pyridinyl, optionally substituted with one, or two substituents selected from a halogen, and a methyl optionally substituted with a F. In a still further embodiment $B^1$ is selected from a pyridinyl, optionally substituted with one, or two substituents selected from Br and $CF_3$. In a further embodiment $B^1$ is selected from a pyridinyl substituted with one substituent selected from halogen, such as Br. In a further embodiment $B^1$ is selected from a pyridinyl substituted with one Cl. In a further embodiment $B^1$ is selected from a pyridinyl substituted with two substituents selected from a halogen and a methyl optionally substituted with a F. In a further embodiment $B^1$ is selected from a pyridinyl substituted with two substituents selected from a halogen and CN, such as one Br and one CN or one Cl and one CN. In a still further embodiment $B^1$ is selected from a pyridinyl substituted with two substituents selected from a Br and a $CF_3$, such as one Br and one $CF_3$.

The skilled person will understand that it may be necessary to adjust or change the order of steps in the processes 1 to 21, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g. t-butyldimethylsilyl, t-butyldiphenylsilyl or trimethylsilyl), AcO (acetoxy), TBS (t-butyldimethylsilyl), TMS (trimethylsilyl), PMB (p-methoxybenzyl), and tetrahydropyranyl. Suitable protecting groups for carboxylic acid include $(C_{1-6})$-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)NH$_2$, TIPS.

The protection and deprotection of functional groups may take place before or after any reaction in the above mentioned processes.

Furthermore the skilled person will appreciate, that, in order to obtain compounds of the invention in an alternative, and on some occasions more convenient manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound (1) is on free form. "On free form" as used herein means a compound of formula (1), either an acid form or base form, or as a neutral compound, depending on the substituents. The free form does not have any acid salt or base salt in addition. In one embodiment the free form is an anhydrate. In another embodiment the free form is a solvate, such as a hydrate.

In a further embodiment the compound of formula (1) is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "$C_{1-x}$ alkyl" as used herein means an alkyl group containing 1-x carbon atoms, e.g. $C_{1-5}$ or $C_{1-6}$, such as methyl, ethyl, propyl, butyl, pentyl or hexyl.

The term "branched $C_{3-6}$ alkyl" as used herein means a branched alkyl group containing 3-6 carbon atoms, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "$C_{5-7}$ cycloalkyl" as used herein means a cyclic alkyl group containing 5-7 carbon atoms, such as cyclopentyl, cyclohexyl, or cycloheptyl.

The term "Oxo" as used herein means an oxygen atom with double bonds, also indicated as =.

The term "CN" as used herein means a nitril.

The term "a five or six membered heteroaromatic ring" as used herein means one five membered heteroaromatic ring or one six membered heteroaromatic ring.

The five membered heteroaromatic ring contains 5 ring atoms of which one to four are heteroatoms selected from N, O, and S. The six membered heteroaromatic ring contains 6 ring atoms of which one to five are heteroatoms selected from N, O and S. Examples include thiophene, furan, pyran, pyrrole, imidazole, pyrazole, isothiazole, isooxazole, pyridine, pyrazine, pyrimidine and pyridazine. When such heteroaromatic rings are substituents they are termed thiophenyl, furanyl, pyranyl, pyrrolyl, imidazolyl, pyrazolyl, isothiazolyl, isooxazolyl, pyridinyl, pyrazinyl, pyrimidinyl and pyridazinyl. Also included are oxazoyl, thiazoyl, thiadiazoyl, oxadiazoyl, and pyridonyl.

The term "a heterocycle, such as heteroaryl or heterocycloalkyl" as used herein means a heterocycle consisting of one or more 3-7 membered ring systems containing one or more heteroatoms and wherein such ring systems may optionally be aromatic. The term "a heteroaryl" as used herein means a mono or bicyclic aromatic ring system containing one or more heteroatoms, such as 1-10, e.g. 1-6, selected from O, S, and N, including but not limited to oxazolyl, oxadiazolyl, thiophenyl, thiadiazolyl, thiazolyl, pyridyl, pyrimidinyl, pyridonyl, pyrimidonyl, quinolinyl, azaquionolyl, isoquinolinyl, azaisoquinolyl, quinazolinyl, azaquinazolinyl, bensozazoyl, azabensoxazoyl, bensothiazoyl, or azabensothiazoyl. The term "a heterocycloalkyl" as used herein means a mono or bicyclic 3-7 membered alifatic heterocycle containing one or more heteroatoms, such as 1-7, e.g. 1-5, selected from O, S, and N, including but not limited to piperidinyl, tetrahydropyranyl, tetrahydrothiopyranyl, or piperidonyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular, a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person skilled within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compounds as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context). This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention indiverse forms thereof.

Experimental Procedures

Evaluation of Kd Values

The affinity of Example 1-32 for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47, (Sörme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salonmonsson et al., 2010).

| Example | Name | Structure | Galectin-1 Kd (μM) | Galectin-3 Kd (μM) |
|---|---|---|---|---|
| 1 | 3,4-Dichlorophenyl 3-deoxy-3-[4-(3-thiophenyl)-1H-1,2,3-triazol-1-yl]-1-thio-α-D-galactopyranoside | 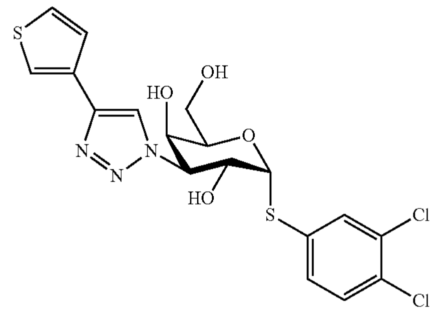 | 0.14 | 2.6 |
| 2 | 2-Chloro-5-fluoro-benzonitril-4-yl 3-deoxy-3-[4-(3-thiophenyl)-1H-1,2,3-triazol-1-yl]-1-thio-α-D-galactopyranoside | 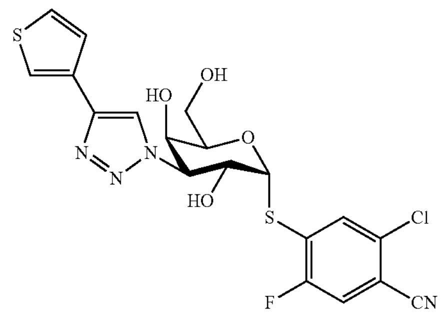 | 0.19 | 1.95 |
| 3 | 5-Bromopyridin-3-yl 3-deoxy-3-[4-(3-thiophenyl)-1H-1,2,3-triazol-1-yl]-1-thio-α-D-galactopyranoside | 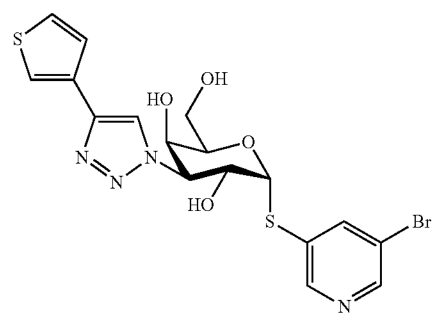 | 0.68 | 1.7 |
| 4 | 5-Bromo-6-trifluoromethyl-pyridin-3-yl 3-deoxy-3-[4-(3-thiophenyl)-1H-1,2,3-triazol-1-yl]-1-thio-α-D-galactopyranoside | 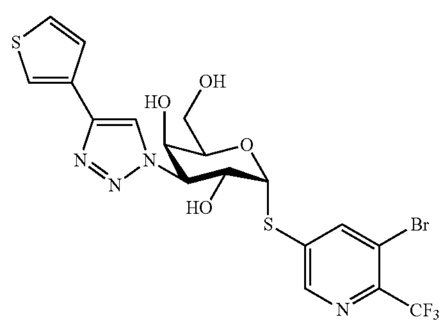 | 0.38 | 1.2 |

| Example | Name | Structure | Galectin-1 Kd (μM) | Galectin-3 Kd (μM) |
|---------|------|-----------|--------------------|--------------------|
| 5 | 3,5-dichloro-4-fluoro-phenyl 3-deoxy-3-[4-(3-thiazolyl)-1H-1,2,3-triazol-1-yl]-1-thio-α-D-galactopyranoside | 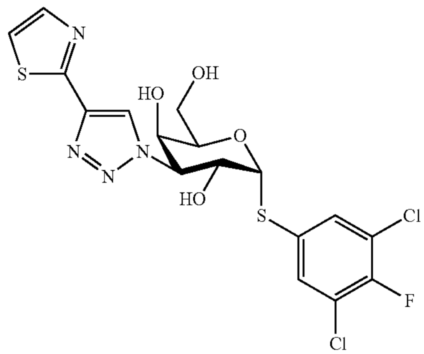 | 0.28 | 10 |
| 6 | 3,4-Dichlorophenyl 3-deoxy-3-[4-(5-fluoro-2-pyridyl)-1H-1,2,3-triazol-1-yl]-1-thio-α-D-galactopyranoside | 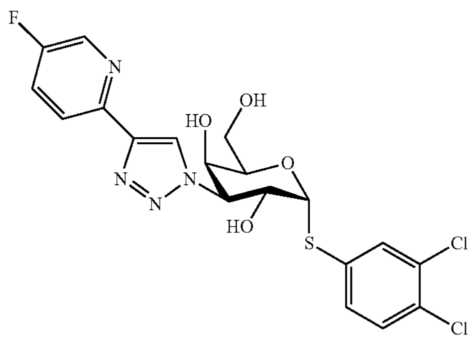 | 0.24 | 0.69 |
| 7 | 5-Bromopyridin-3-yl 3-deoxy-3-[4-(2-thiophenyl)-1H-1,2,3-triazol-1-yl]-1-thio-α-D-galactopyranoside | 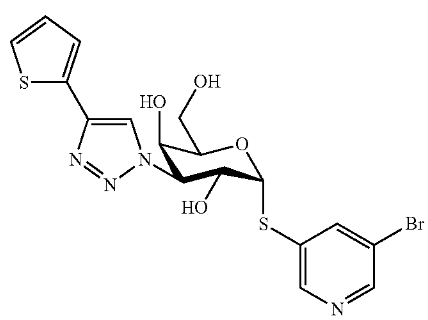 | 0.45 | 1.25 |
| 8 | 3,5-Dichloro-4-fluoro-phenyl 3-deoxy-3-[4-(2-thiophenyl)-1H-1,2,3-triazol-1-yl]-1-thio-α-D-galactopyranoside | 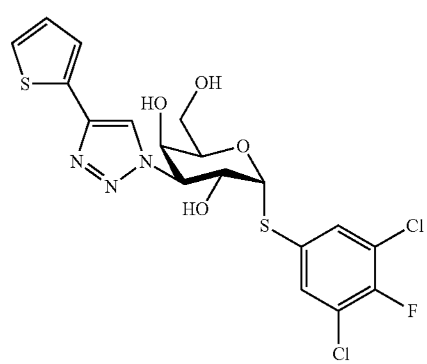 | 0.92 | 2.3 |

-continued

| Example | Name | Structure | Galectin-1 Kd (μM) | Galectin-3 Kd (μM) |
|---|---|---|---|---|
| 9 | 3,4-Dichlorophenyl 3-deoxy-3-[4-(5-fluoro-2-thiophenyl)-1H-1,2,3-triazol-1-yl]-1-thio-α-D-galactopyranoside | 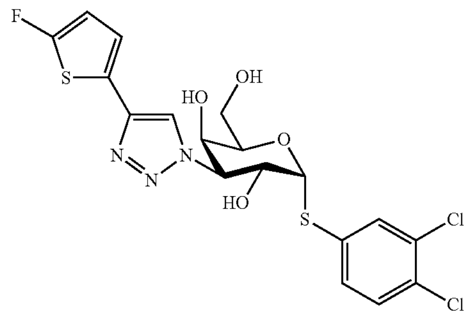 | 0.55 | 0.97 |
| 10 | 5-Bromopyridin-3-yl 3-deoxy-3-[4-(4-thiazolyl)-1H-1,2,3-triazol-1-yl]-1-thio-α-D-galactopyranoside | 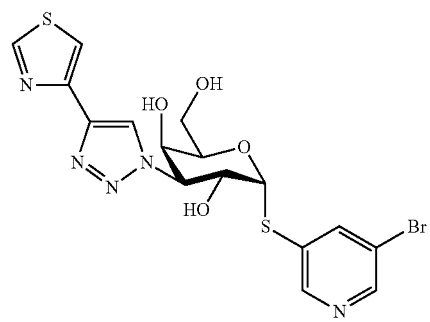 | 0.25 | 4.1 |
| 11 | 5-Bromo-6-trifluoromethyl-pyridin-3-yl 3-deoxy-3-[4-(4-thiazolyl)-1H-1,2,3-triazol-1-yl]-1-thio-α-D-galactopyranoside | 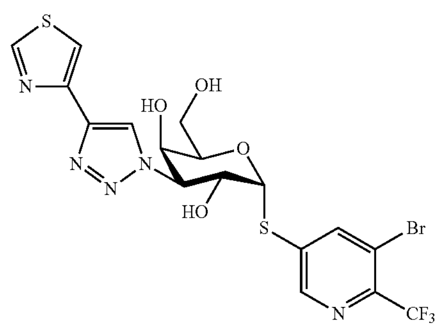 | 0.17 | 2.9 |
| 12 | 3,4-Dichlorophenyl 3-deoxy-3-[4-(4-thiazolyl)-1H-1,2,3-triazol-1-yl]-1-thio-α-D-galactopyranoside | 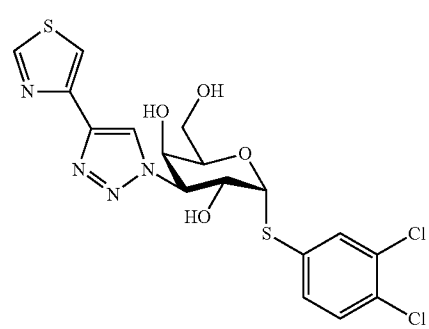 | 0.31 | 5.3 |

-continued

| Example | Name | Structure | Galectin-1 Kd (μM) | Galectin-3 Kd (μM) |
|---|---|---|---|---|
| 13 | 2-Chloro-benzonitril-4-yl 3-deoxy-3-[4-(4-thiazolyl)-1H-1,2,3-triazol-1-yl]-1-thio-α-D-galactopyranoside | 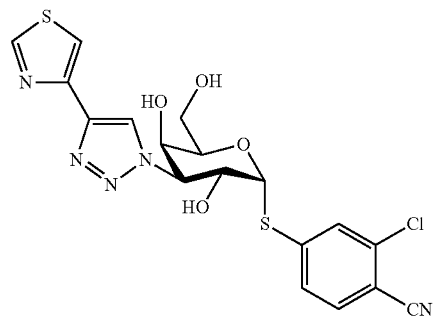 | 0.37 | 6.1 |
| 14 | 3,5-Dichloro-4-fluoro-phenyl 3-deoxy-3-[4-(4-thiazolyl)-1H-1,2,3-triazol-1-yl]-1-thio-α-D-galactopyranoside | 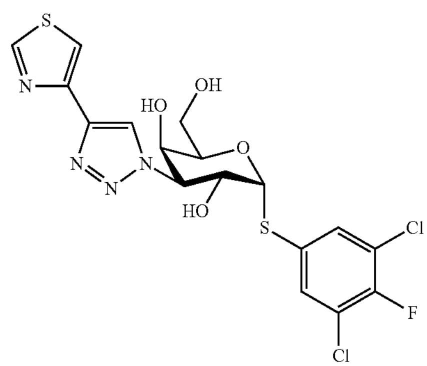 | 0.23 | 6.2 |
| 15 | 5-Bromopyridin-3-yl 3-deoxy-3-[4-(2-methyl-4-thiazolyl)-1H-1,2,3-triazol-1-yl]-1-thio-α-D-galactopyranoside | 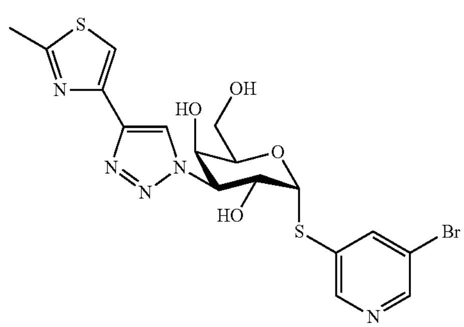 | 0.64 | 3.2 |
| 16 | 2,6-Dichloro-bensonitrile-4-yl 3-deoxy-3-[4-(2-thiazolyl)-1H-1,2,3-triazol-1-yl]-1-thio-α-D-galactopyranoside | 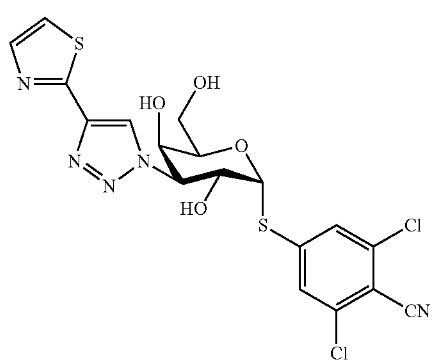 | 0.8 | 12 |

-continued

| Example | Name | Structure | Galectin-1 Kd (μM) | Galectin-3 Kd (μM) |
|---|---|---|---|---|
| 17 | 3,4,5-Trichlorophenyl 3-deoxy-3-[4-(2-thiazolyl)-1H-1,2,3-triazol-1-yl]-1-thio-α-D-galactopyranoside | 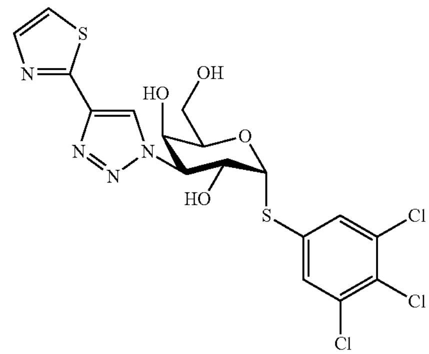 | 0.61 | 1.3 |
| 18 | 3,4-Dichlorophenyl 3-deoxy-3-[4-(2-thiazolyl)-1H-1,2,3-triazol-1-yl]-1-thio-α-D-galactopyranoside | 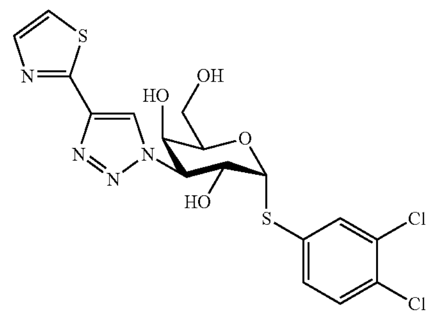 | 0.24 | 4.1 |
| 19 | 3,4,5-Trichlorophenyl 3-deoxy-3-[4-(1,3,4-thiadiazol-2-yl)-1H-1,2,3-triazol-1-yl]-1-thio-α-D-galactopyranoside | 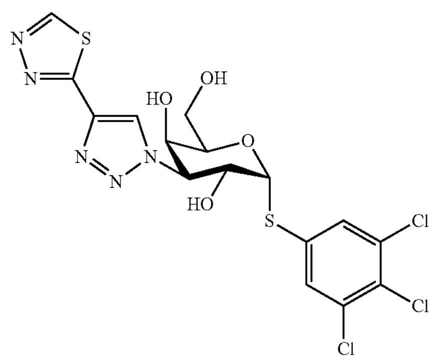 | 0.35 | 4.4 |
| 20 | 5-Bromopyridin-3-yl 3-deoxy-3-[4-(2-thiazolyl)-1H-1,2,3-triazol-1-yl]-1-thio-α-D-galactopyranoside | 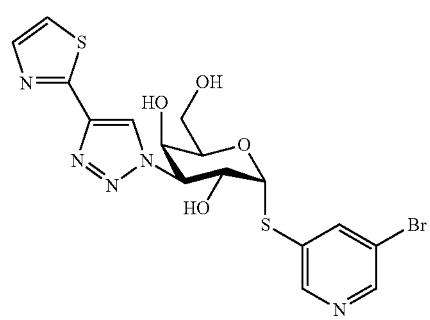 | 0.55 | 4.6 |

-continued

| Example | Name | Structure | Galectin-1 Kd (μM) | Galectin-3 Kd (μM) |
|---|---|---|---|---|
| 21 | 5-Chloropyridin-3-yl 3-deoxy-3-[4-(2-thiazolyl)-1H-1,2,3-triazol-1-yl]-1-thio-α-D-galactopyranoside | 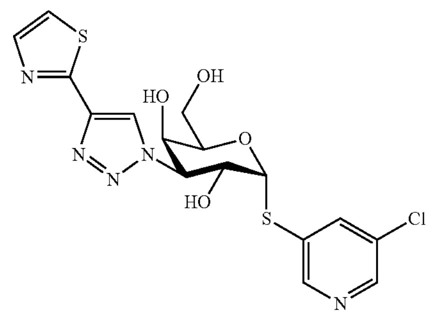 | 0.22 | 1.8 |
| 22 | 5-Bromo-2-cyano-pyridine-3-yl 3-deoxy-3-[4-(2-thiazolyl)-1H-1,2,3-triazol-1-yl]-1-thio-α-D-galactopyranoside | 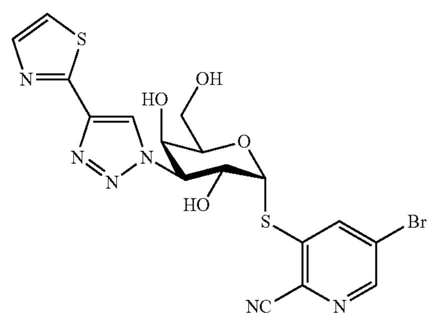 | 0.2 | 1.2 |
| 23 | 5-Chloro-6-cyano-pyridine-3-yl 3-deoxy-3-[4-(2-thiazolyl)-1H-1,2,3-triazol-1-yl]-1-thio-α-D-galactopyranoside | 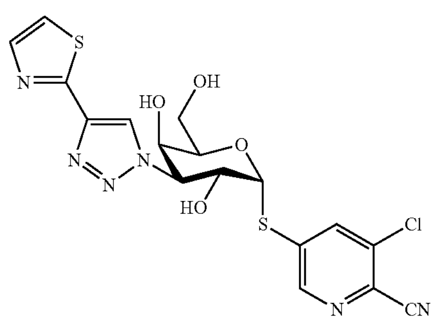 | 0.44 | 4.4 |
| 24 | 3,5-Dichlorophenyl 3-deoxy-3-[4-(2-thiazolyl)-1H-1,2,3-triazol-1-yl]-1-thio-α-D-galactopyranoside | 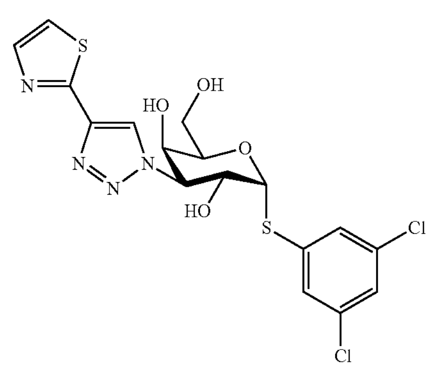 | 0.34 | 1.6 |

-continued

| Example | Name | Structure | Galectin-1 Kd (μM) | Galectin-3 Kd (μM) |
|---------|------|-----------|--------------------|--------------------|
| 25 | 3-Bromo-4-chlorophenyl 3-deoxy-3-[4-(2-thiazolyl)-1H-1,2,3-triazol-1-yl]-1-thio-α-D-galactopyranoside | 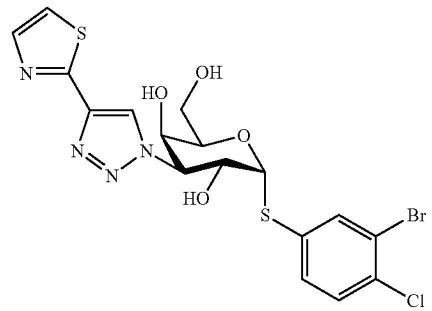 | 0.44 | 4.4 |
| 26 | 5-Bromo-6-trifluoromethyl-pyridine-3-yl 3-deoxy-3-[4-(2-thiazolyl)-1H-1,2,3-triazol-1-yl]-1-thio-α-D-galactopyranoside | 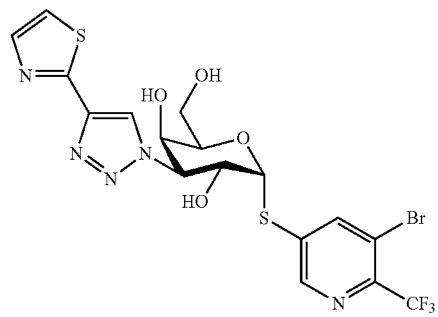 | 0.31 | 2 |
| 27 | 3-Bromo-4-fluoro-phenyl 3-deoxy-3-[4-(2-thiazolyl)-1H-1,2,3-triazol-1-yl]-1-thio-α-D-galactopyranoside | 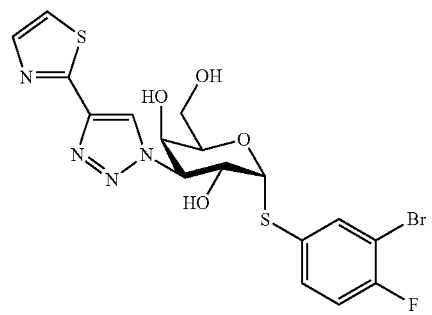 | 0.49 | 4.7 |
| 28 | 2,5-Dichlorophenyl 3-deoxy-3-[4-(2-thiazolyl)-1H-1,2,3-triazol-1-yl]-1-thio-α-D-galactopyranoside | 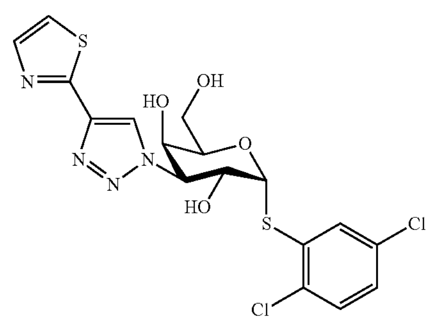 | 0.91 | 8.2 |
| 29 | 3,4-Dichlorophenyl 3-deoxy-3-[4-(4-bromo-thiazol-2-yl)-1H-1,2,3-triazol-1-yl]-1-thio-α-D-galactopyranoside | 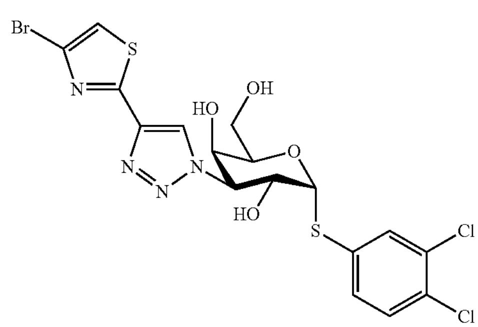 | 0.15 | 0.81 |

| Example | Name | Structure | Galectin-1 Kd (μM) | Galectin-3 Kd (μM) |
|---------|------|-----------|---------------------|---------------------|
| 30 | 3,4-Dichlorophenyl 3-deoxy-3-[4-(5-fluoro-thiazol-2-yl)-1H-1,2,3-triazol-1-yl]-1-thio-α-D-galactopyranoside | 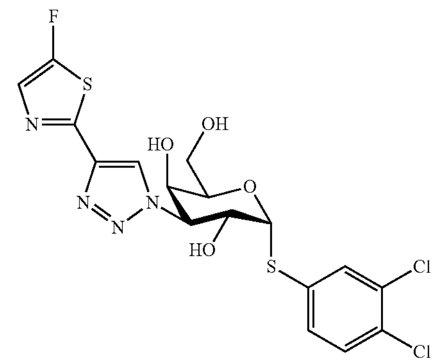 | 0.4 | 1.6 |
| 31 | 3,4-Dichlorophenyl 3-deoxy-3-[4-(4-chloro-thiazol-2-yl)-1H-1,2,3-triazol-1-yl]-1-thio-α-D-galactopyranoside | 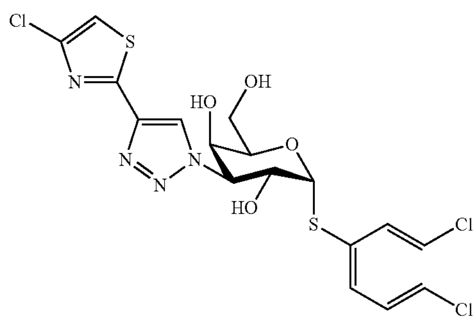 | 0.12 | 0.46 |
| 32 | 3,4-Dichlorophenyl 3-deoxy-3-[4-(4-trifluoromethyl-thiazol-2-yl)-1H-1,2,3-triazol-1-yl]-1-thio-α-D-galactopyranoside | 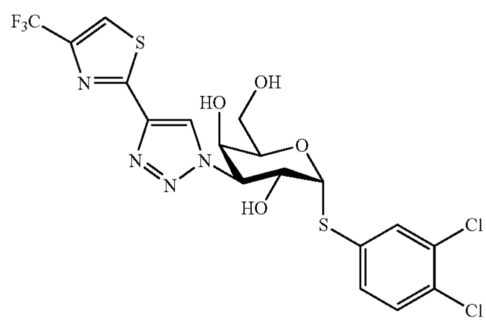 | 0.79 | 0.21 |

In Vitro ADME Properties

The permeability (Papp) (Caco-2 A>B) was determined from the apical (A) to the basolateral (B) direction in adenocarcinoma cells from human colon. The human hepatic stability ($CL_{int}$) was determined in human hepatocytes.

| Example | CACO-2 A > B Papp (10^−6 cm/s) | Human hepatic Clint $CL_{int}$ (ml/min/kg) |
|---------|-------------------------------|---------------------------------------------|
| 1 | 10.1 | 12.1 |
| 4 | 2.5 | 11.3 |
| 5 | 10.5 | 0.38 |
| 14 | 8.8 | 0* |

*No degradation was observed under the assay conditions.

Synthesis of Examples and Intermediates

General Experimental:

Nuclear Magnetic Resonance (NMR) spectra were recorded on a 400 MHz Bruker AVANCE III 500 instrument at 25° C. Chemical shifts are reported in ppm using the residual solvent as internal standard. Peak multiplicities are expressed as follow: s, singlet; d, doublet; dd, doublet of doublets; t, triplet; dt, doublet of triplet; q, quartet; m, multiplet; br s, broad singlet.

LC-MS spectra were acquired on an Agilent 1200 HPLC coupled with an Agilent MSD mass spectrometer operating in ES (+) ionization mode. Column: XBridge C18 (4.6×50 mm, 3.5 μm) or SunFire C18 (4.6×50 mm, 3.5 μm). Solvent A (0.1% TFA in water) and solvent B (Acetonitrile+0.1% TFA) or solvent A (10 mM Ammonium hydrogen carbonate in water) and solvent B (Acetonitrile). Wavelength: 254 nM. Preparative HPLC was performed on a Gilson 215. Flow: 25 mL/min Column: XBrige prep C18 10 μm OBD (19×250 mm) column. Wavelength: 254 nM. Solvent A (10 mM Ammonium hydrogen carbonate in water) and solvent B (Acetonitrile).

The following abbreviations are used:
Calcd: Calculated
$CH_3CN$: Acetonitrile
DCM: Dichloromethane DIPEA: N,N-Diisopropylethylamine
DMF: N,N-dimethylformamide
ESI-MS: Electrospray ionization mass spectrometry
EtOAc or EA: Ethylacetate
GC: Gas chromatography
HPLC: High performance liquid chromatography
MeOH: Methanol
MeOD-d4: Deuterated methanol
MS: Mass spectroscopy
MTBE: tert-butyl methyl ether
NaOMe: Sodium methoxide
NMR: Nuclear magnetic resonance
PE: petroleum ether
Prep: Preparative
rt: Room temperature
TBSOTf: tert-Butyldimethylsilyl trifluoromethane-sulfonate
TBME: tert-Butyl methyl ether
TEA: Triethylamine
TFA: trifluoroacetic acid
THF: Tetrahydrofuran
TMS: Trimethyl silyl
UV: Ultraviolet Example 1

3,4-Dichlorophenyl 3-deoxy-3-[4-(3-thiophenyl)-1H-1,2,3-triazol-1-yl]-1-thio-α-D-galactopyranoside

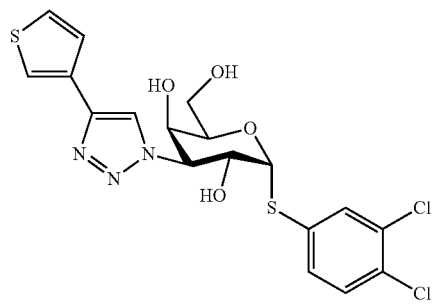

To a solution of 3,4-Dichlorophenyl 2,4,6-tri-O-acetyl-3-deoxy-3-[4-(3-thiophenyl)-1H-1,2,3-triazol-1-yl]-1-thio-α-D-galactopyranoside (130 mg, 0.22 mmol) in MeOH (10 mL), NaOMe (11.7 mg, 0.22 mmol) was added and the reaction mixture was stirred at rt for 16 h. The reaction mixture was acidified by hydrogen form resin followed by filtration and evaporation. The residue was purified by Preparative HPLC to give 45 mg (44%) of the title compound.

$^1$H NMR (400 MHz, DMSO) δ 8.47 (s, 1H), 7.95-7.77 (m, 2H), 7.71-7.40 (m, 4H), 5.89 (dd, J=14.3, 4.0 Hz, 2H), 5.49 (d, J=6.4 Hz, 1H), 4.84-4.63 (m, 3H), 4.25 (t, J=6.4 Hz, 1H), 4.03 (d, J=6.6 Hz, 1H), 3.62-3.49 (m, 1H), 3.46-3.38 (m, 1H). ESI-MS m/z calcd for $[C_{18}H_{18}Cl_2N_3O_4S_2]^+$ (M+H)$^+$: 474.0; found: 474.0.

Example 2

2-Chloro-5-fluoro-benzonitril-4-yl 3-deoxy-3-[4-(3-thiophenyl)-1H-1,2,3-triazol-1-yl]-1-thio-α-D-galactopyranoside

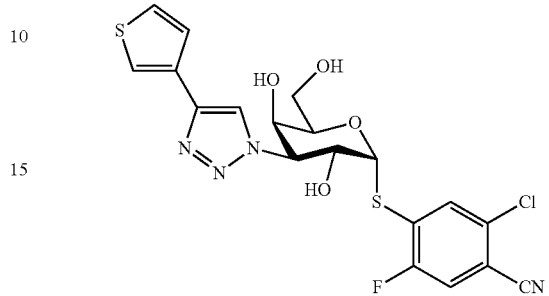

A solution of 2-Chloro-5-fluoro-benzonitril-4-yl 2,4,6-tri-O-acetyl-3-deoxy-3-[4-(3-thiophenyl)-1H-1,2,3-triazol-1-yl]-1-thio-α-D-galactopyranoside (150 mg, 0.25 mmol) in MeOH/TEA/H$_2$O (2.5/1.5/0.5) (4.5 mL) was stirred at room temperature with for 4 h. The mixture was evaporated to dryness. The crude product was purified by HPLC to afford the title compound as a white solid (75 mg, 63%) m/z calcd for $[C_{19}H_{16}ClFN_4O_4S_2]^+$ [M+H]$^+$: 484.0; found: 484.0.

$^1$H NMR (400 MHz, MeOD-d4) δ 8.38 (s, 1H), 8.03 (d, J=6.4 Hz, 1H), 7.79 (dd, J=2.4, 1.7 Hz, 1H), 7.68 (d, J=9.0 Hz, 1H), 7.56-7.51 (m, 2H), 6.21 (d, J=5.2 Hz, 1H), 5.08 (dd, J=11.4, 2.7 Hz, 1H), 5.00 (dd, J=11.3, 5.3 Hz, 1H), 4.32 (t, J=6.1 Hz, 1H), 4.21 (d, J=1.9 Hz, 1H), 3.66 (qd, J=11.5, 6.1 Hz, 2H).

Example 3

5-Bromopyridin-3-yl 3-deoxy-3-[4-(3-thiophenyl)-1H-1,2,3-triazol-1-yl]-1-thio-α-D-galactopyranoside

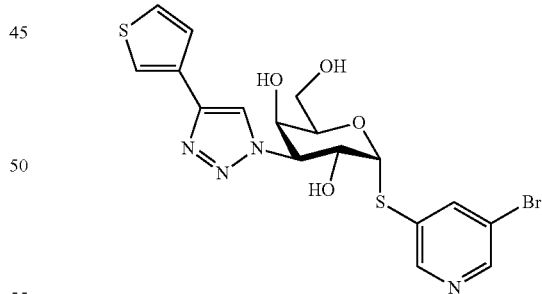

5-Bromopyridin-3-yl 2,4,6-tri-O-acetyl-3-deoxy-3-[4-(3-thiophenyl)-1H-1,2,3-triazol-1-yl]-1-thio-α-D-galactopyranoside (80 mg, 0.13 mmol) was dissolved in MeOH (4 mL). Sodium methoxide (7.07 mg, 0.13 mmol) was added. The mixture was stirred at rt for 16 hours. The mixture was concentrated in vacuum and the residue was purified on C-18 column using a gradient of CH$_3$CN/10 mM NH$_4$HCO$_3$ from 0-42% to give 30 mg (47.2%) of the title compound.

$^1$H NMR (400 MHz, DMSO) δ 8.67 (d, J=1.9 Hz, 1H), 8.61 (d, J=2.1 Hz, 1H), 8.47 (s, 1H), 8.30 (t, J=2.0 Hz, 1H), 7.87 (dd, J=2.9, 1.2 Hz, 1H), 7.65 (dd, J=5.0, 3.0 Hz, 1H), 7.56 (dd, J=5.0, 1.2 Hz, 1H), 5.95 (dd, J=12.9, 4.8 Hz, 2H), 5.51 (d, J=6.4 Hz, 1H), 4.85-4.69 (m, 3H), 4.25 (t, J=6.2 Hz, 1H), 4.08-3.96 (m, 1H), 3.60-3.47 (m, 1H), 3.43-3.36 (m, 1H). ESI-MS J/z calcd for [C$_{17}$H$_{18}$BrN$_4$O$_4$S$_2$]$^+$ (M+H)$^+$: 485.0; found: 485.0.

Example 4

5-Bromo-6-trifluoromethyl-pyridin-3-yl 3-deoxy-3-[4-(3-thiophenyl)-1H-1,2,3-triazol-1-yl]-1-thio-α-D-galactopyranoside

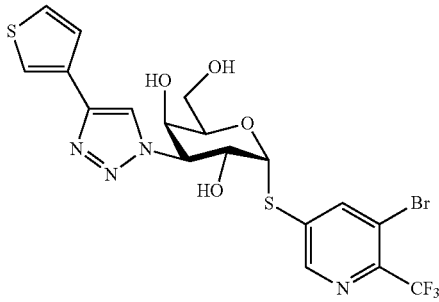

5-Bromo-6-trifluoromethyl-pyridin-3-yl 2,4,6-tri-O-acetyl-3-azido-3-deoxy-1-thio-α-D-galactopyranoside (70 mg, 0.12 mmol) and 3-ethynylthiophene (39.8 mg, 0.37 mmol) were dissolved in CH$_3$CN (10 mL). Then Copper(I) Iodide (23.3 mg, 0.12 mmol) and TEA (37.19 mg, 0.37 mmol) were added. The mixture was stirred at rt over night. Then the mixture was filtered and concentrated. The residue was dissolved in MeOH (4 mL). NaOMe (4.8 mg, 0.09 mmol) was added. The mixture was stirred at rt for another 16 hours. Then the mixture was concentrated and the residue was purified on C-18 column using a gradient of CH$_3$CN/10 mM NH$_4$HCO$_3$ from 0-29%. 8 mg (16.4%) of the title compound was obtained as white solid.

$^1$H NMR (400 MHz, MeOD-d4) δ 8.77 (d, J=1.5 Hz, 1H), 8.53 (s, 1H), 8.39 (s, 1H), 7.84-7.77 (m, 1H), 7.58-7.50 (m, 2H), 6.15 (d, J=5.0 Hz, 1H), 5.08-4.96 (m, 2H), 4.43 (t, J=6.0 Hz, 1H), 4.21 (s, 1H), 3.82-3.64 (m, 2H).

ESI-MS m/z calcd for [C$_{18}$H$_{17}$BrF$_3$N$_4$O$_4$S$_2$]$^+$ (M+H)$^+$: 553.0; found: 553.0.

Example 5

3,5-Dichloro-4-fluoro-phenyl 3-deoxy-3-[4-(3-thiazolyl)-1H-1,2,3-triazol-1-yl]-1-thio-α-D-galactopyranoside

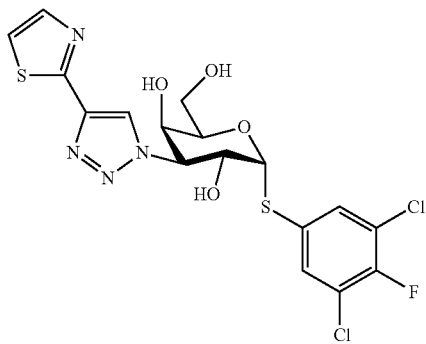

To a solution of 3,5-Dichloro-4-fluoro-phenyl 2,4,6-tri-O-acetyl-3-deoxy-3-[4-(3-thiazolyl)-1H-1,2,3-triazol-1-yl]-1-thio-α-D-galactopyranoside (30 mg, 0.05 mmol) in MeOH/TEA/H$_2$O (10/3/1)(2 mL) was stirred at room temperature for 20 h. The reaction mixture was evaporated to dryness and the residue was purified by Prep-HPLC to afford the title compound as a white solid. (10 mg, 41%).

ESI-MS m/z calcd for [C$_{17}$H$_{15}$Cl$_2$FN$_4$O$_4$S$_2$]$^+$ [M+H]$^+$: 493.0; found: 493.0.

$^1$H NMR (400 MHz, MeOD-d4) δ 8.60 (s, 1H), 7.91 (d, J=3.2 Hz, 1H), 7.76 (d, J=6.3 Hz, 2H), 7.66 (d, J=3.3 Hz, 1H), 5.85 (d, J=5.3 Hz, 1H), 5.05 (dd, J=11.4, 2.7 Hz, 1H), 4.93 (dd, J=11.4, 5.2 Hz, 1H), 4.51 (t, J=6.0 Hz, 1H), 4.22 (d, J=2.3 Hz, 1H), 3.79-3.68 (m, 2H).

Example 6

3,4-Dichlorophenyl 3-deoxy-3-[4-(5-fluoro-2-pyridyl)-1H-1,2,3-triazol-1-yl]-1-thio-α-D-galactopyranoside

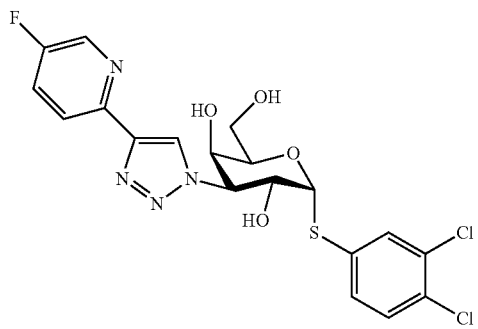

To a solution of 3,4-Dichlorophenyl 2,4,6-tri-O-acetyl-3-deoxy-3-[4-(5-fluoro-2-pyridyl)-1H-1,2,3-triazol-1-yl]-1-thio-α-D-galactopyranoside (200 mg, 0.33 mmol) in methanol (10 mL) was added sodium methoxide (1.76 mg, 0.03 mmol). Then the mixture was held at room temperature with stirring on for 2 h. After completion, the DOWEX 50wx8-200 Ion exchange resin was added (pH=7) and mixture was filtered. The filtrate was concentrated to and purified by preparative HPLC. The appropriate fractions were combined and lyophilized to give the title compound 50 mg (32%) as a white solid.

$^1$H NMR (500 MHz, MeOD-d4) δ 8.58 (s, 1H), 8.52 (d, J=2.4 Hz, 1H), 8.15 (dd, J=8.7, 4.3 Hz, 1H), 7.83 (d, J=2.1 Hz, 1H), 7.74 (td, J=8.6, 2.8 Hz, 1H), 7.54 (dt, J=27.6, 5.2 Hz, 2H), 5.87 (d, J=5.3 Hz, 1H), 5.03 (dd, J=11.4, 2.8 Hz, 1H), 5.01-4.97 (m, 1H), 4.52 (t, J=6.0 Hz, 1H), 4.23 (d, J=2.1 Hz, 1H), 3.74 (qd, J=11.5, 6.1 Hz, 2H).

m/z calcd for [C$_{19}$H$_{17}$Cl$_2$FN$_4$O$_4$S]$^+$ [M+H]$^+$: 487.0; found: 487.0.

Example 7

5-Bromopyridin-3-yl 3-deoxy-3-[4-(2-thiophenyl)-1H-1,2,3-triazol-1-yl]-1-thio-α-D-galactopyranoside

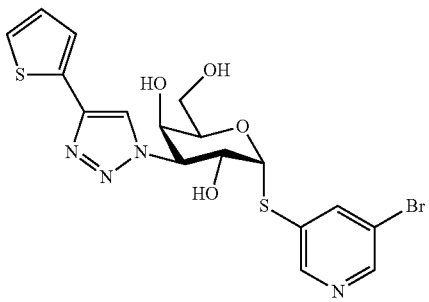

A solution of 5-Bromopyridin-3-yl 2,4,6-tri-O-acetyl-3-deoxy-3-[4-(2-thiophenyl)-1H-1,2,3-triazol-1-yl]-1-thio-α-D-galactopyranoside (30 mg, 0.05 mmol) in MeOH/TEA/H$_2$O (5/3/1) (1 mL) was stirred at room temperature for 20 h. The mixture was evaporated to dryness and the residue was purified by HPLC (H$_2$O/CH$_3$CN=40%) to afford the title compound as a white solid (21 mg, 87%).

m/z calcd for [C$_{17}$H$_{17}$BrN$_4$O$_4$S$_2$]$^+$ [M+H]$^+$: 485.0: found: 485.0.

$^1$H NMR (400 MHz, MeOD-d4) δ 8.70 (d, J=1.8 Hz, 1H), 8.58 (d, J=2.0 Hz, 1H), 8.35 (dd, J=6.0, 4.0 Hz, 2H), 7.45 (dd, J=9.1, 4.2 Hz, 2H), 7.13 (dd, J=5.0, 3.7 Hz, 1H), 5.93 (d, J=5.2 Hz, 1H), 5.02 (dd, J=11.5, 2.7 Hz, 1H), 4.98-4.92 (dd, J=11.5, 5.2 Hz, 1H), 4.50 (t, J=5.9 Hz, 1H), 4.22 (d, J=1.9 Hz, 1H), 3.78-3.67 (m, 2H).

Example 8

3,5-Dichloro-4-fluoro-phenyl 3-deoxy-3-[4-(2-thiophenyl)-1H-1,2,3-triazol-1-yl]-1-thio-α-D-galactopyranoside

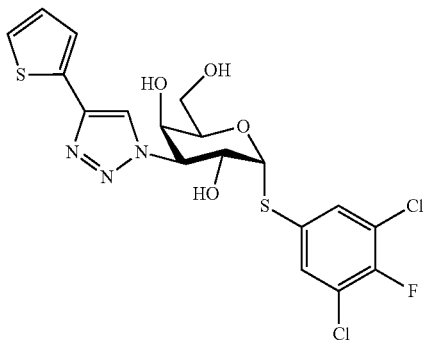

A solution of 1,3-dideoxy-2,4,6-tri-O-acetyl-1-(3,5-dichloro-4-fluorophenylthio)-3-[4-(thiophen-2-yl)-1H-1,2,3-triazol-1-yl]-α-D-galactopyranoside (30 mg, 0.05 mmol) in MeOH/TEA/H$_2$O (10/3/1)(2 mL) was stirred at room temperature for 20 h. The mixture was evaporated to dryness and the residue was purified by Prep-HPLC to afford the title compound as a white solid. (10 mg, 41%).

ESI-MS m/z calcd for [C$_{17}$H$_{16}$Cl$_2$FN$_3$O$_4$S$_2$]$^+$ [M+H]$^+$: 492.0; found: 492.0.

$^1$H NMR (400 MHz, MeOD-d4) δ 8.35 (s, 1H), 7.75 (d, J=6.3 Hz, 2H), 7.45 (ddd, J=6.1, 4.3, 1.1 Hz, 2H), 7.13 (dd, J=5.1, 3.6 Hz, 1H), 5.84 (d, J=5.0 Hz, 1H), 4.98 (dd, J=11.4, 2.6 Hz, 1H), 4.93 (dd, J=11.4, 5.0 Hz, 1H), 4.50 (t, J=6.0 Hz, 1H), 4.21 (d, J=1.6 Hz, 1H), 3.79-3.62 (m, 2H).

Example 9

3,4-Dichlorophenyl 3-deoxy-3-[4-(5-fluoro-2-thiophenyl)-1H-1,2,3-triazol-1-yl]-1-thio-α-D-galactopyranoside

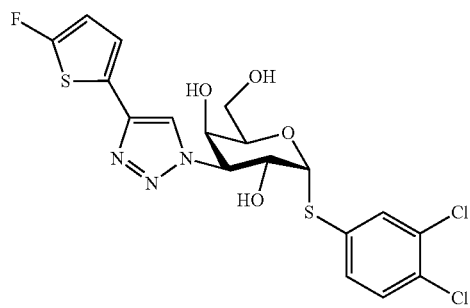

3,4-Dichlorophenyl 2,4,6-tri-O-acetyl-3-deoxy-3-[4-(5-fluoro-2-thiophenyl)-1H-1,2,3-triazol-1-yl]-1-thio-α-D-galactopyranoside (8 mg, 0.013 mmol) was dissolved in water (1 ml), methanol (2 ml) followed by addition of TEA (0.5 ml). The reaction mixture was stirred at rt for 5 h. The reaction mixture was concentrated and purified by column chromatography on C-18 silica gel eluted with CH$_3$CN/Water (5:95~10:90~50:50) to give the title compound, 3.4 mg, 50%.

1H NMR (400 MHz, MeOD-d4) δ 8.35 (s, 1H), 7.81 (d, J=2.0 Hz, 1H), 7.60-7.53 (m, 1H), 7.53-7.46 (m, 1H), 7.09 (t, J=3.8 Hz, 1H), 6.60 (dd, J=4.1, 2.1 Hz, 1H), 5.85 (d, J=5.1 Hz, 1H), 5.01-4.94 (m, 2H), 4.50 (t, J=6.1 Hz, 1H), 4.20 (d, J=1.7 Hz, 1H), 3.80-3.64 (m, 2H). ESI-MS m/z calcd for [C$_{18}$H$_{16}$Cl$_2$FN$_3$O$_4$S$_2$]$^+$ (M+H)$^+$: 492.0; found: 492.0.

Example 10

5-Bromopyridin-3-yl 3-deoxy-3-[4-(4-thiazolyl)-1H-1,2,3-triazol-1-yl]-1-thio-α-D-galactopyranoside

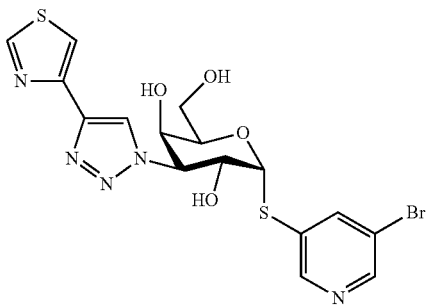

2,4,6-tri-o-acetyl-3-(4-(thiazol-4-yl)-1H-1,2,3-triazol-1-yl)-1-(5-bromopyridin-3-ylthio)-1,3-dideoxy-α-D-galactopyranoside (50 mg, 0.08 mmol) was dissolved in MeOH (4 mL). NaOMe (4.4 mg, 0.08 mmol) was added. The reaction mixture was stirred at rt for 16 h. The mixture was purified on C-18 column using a gradient of $CH_3CN$/10 mM $NH_4HCO_3$ from 0-28% to obtain the title compound 15 mg (38%).

$^1$H NMR (400 MHz, MeOD-d4) δ 9.12 (d, J=2.0 Hz, 1H), 8.70 (d, J=1.8 Hz, 1H), 8.58 (d, J=2.1 Hz, 1H), 8.48 (s, 1H), 8.35 (t, J=2.0 Hz, 1H), 8.01 (d, J=2.0 Hz, 1H), 5.93 (d, J=5.3 Hz, 1H), 5.09-5.03 (m, 1H), 5.00-4.90 (m, 1H), 4.51 (t, J=6.1 Hz, 1H), 4.24 (d, J=2.6 Hz, 1H), 3.79-3.66 (m, 2H).

ESI-MS m/z calcd for $[C_{16}H_{17}BrN_5O_4S_2]^+$ $(M+H)^+$: 486.0; found: 486.0.

Example 11

5-Bromo-6-trifluoromethyl-pyridin-3-yl 3-deoxy-3-[4-(4-thiazolyl)-1H-1,2,3-triazol-1-yl]-1-thio-α-D-galactopyranoside

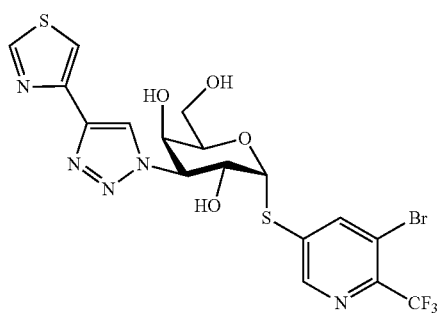

NaOMe (0.4 mg, 0.007 mmol) was added to a solution of crude mixture of 5-Bromo-6-trifluoromethyl-pyridin-3-yl 2,4,6-tri-O-acetyl-3-deoxy-3-[4-(4-thiazolyl)-1H-1,2,3-triazol-1-yl]-1-thio-α-D-galactopyranoside (50 mg, 0.07 mmol) in MeOH (5 mL) at room temperature. The mixture was stirred at room temperature for 1 h. The mixture was acidified with dowex 50 wx8 hydrogen form to pH=5~6. The solution was filtered, washed with MeOH (20 mL) and concentrated in vacuo to afford crude product, which was purified by Prep-HPLC to afford the title compound (20.7 mg, 53% yield).

$^1$H NMR (400 MHz, MeOD-d4) δ 9.13 (s, 1H), 8.77 (d, J=1.8 Hz, 1H), 8.51 (d, J=18.8 Hz, 2H), 8.02 (s, 1H), 6.15 (d, J=5.2 Hz, 1H), 5.09 (dd, J=11.3, 2.7 Hz, 1H), 4.99 (dd, J=11.5, 5.3 Hz, 1H), 4.43 (t, J=6.0 Hz, 1H), 4.23 (s, 1H), 3.72 (d, J=5.3 Hz, 2H).

ESI-MS m/z calcd for $[C_{17}H_{15}BrF_3N_5O_4S_2]^+$ $(M+H)^+$: 553.0; found: 554.0.

Example 12

3,4-Dichlorophenyl 3-deoxy-3-[4-(4-thiazolyl)-1H-1,2,3-triazol-1-yl]-1-thio-α-D-galactopyranoside

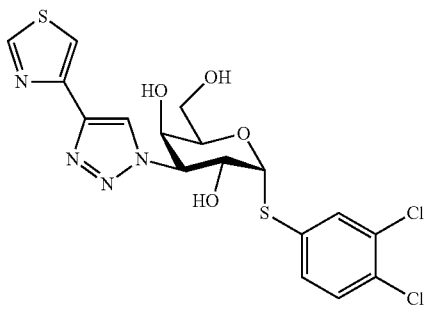

A solution of 1,3-dideoxy-2,4,6-tri-O-acetyl-1-(3,4-dichlorophenylthio)-3-[4-(thiazol-4-yl)-1H-1,2,3-triazol-1-yl]-α-D-galactopyranoside (70 mg, 0.12 mmol) in MeOH/TEA/$H_2O$ (10/3/1) (3 mL) was stirred at room temperature for 20 h. The mixture was evaporated to dryness and the residue was purified by Prep-HPLC to afford product as a white solid (20 mg, 68.6%).

ESI-MS m/z calcd for $[C_{17}H_{16}Cl_2N_4O_4S_2]^+$ $[M+H]^+$: 475.0; found: 475.0.

$^1$H NMR (400 MHz, MeOD-d4) δ 9.12 (d, J=2.0 Hz, 1H), 8.47 (s, 1H), 8.01 (d, J=2.0 Hz, 1H), 7.82 (d, J=2.0 Hz, 1H), 7.56 (dd, J=8.4, 2.0 Hz, 1H), 7.50 (d, J=8.4 Hz, 1H), 5.87 (d, J=5.3 Hz, 1H), 5.03 (dd, J=11.4, 2.8 Hz, 1H), 4.95 (dd, J=11.4, 5.3 Hz, 1H), 4.51 (t, J=6.1 Hz, 1H), 4.23 (d, J=2.1 Hz, 1H), 3.79-3.68 (m, 1H).

Example 13

2-Chloro-benzonitril-4-yl 3-deoxy-3-[4-(4-thiazolyl)-1H-1,2,3-triazol-1-yl]-1-thio-α-D-galactopyranoside

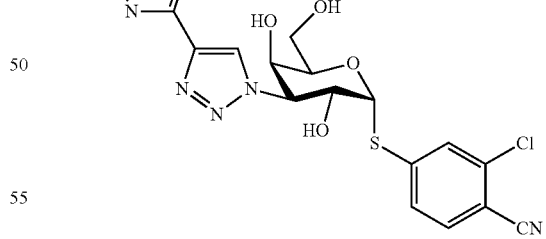

A solution of 2-chloro-benzonitril-4-yl 2,4,6-tri-O-acetyl-3-deoxy-3-[4-(4-thiazolyl)-1H-1,2,3-triazol-1-yl]-1-thio-α-D-galactopyranoside (50 mg, 0.08 mmol) in MeOH/TEA/$H_2O$ (10/3/1) (3 mL) was stirred at room temperature for 20 h. The reaction mixture was evaporated to dryness and the residue was purified by Prep-HPLC to afford the title compound as a white solid (15 mg, 40%).

ESI-MS m/z calcd for $[C_{18}H_{16}ClN_5O_4S_2]^-$ $[M+H]^-$: 466.0; found: 466.0.

$^1$H NMR (400 MHz, McOD-d4) δ 9.12 (d, J=2.0 Hz, 1H), 8.48 (s, 1H), 8.01 (d, J=2.0 Hz, 1H), 7.88 (d, J=1.5 Hz, 1H), 7.70 (dt, J=8.3, 4.9 Hz, 2H), 6.13 (d, J=5.2 Hz, 1H), 5.06 (dd, J=11.4, 2.7 Hz, 1H), 4.98 (dd, J=11.4, 5.3 Hz, 1H), 4.40 (t, J=6.0 Hz, 1H), 4.23 (d, J=1.9 Hz, 1H), 3.81-3.66 (m, 2H).

Example 14

3,5-Dichloro-4-fluoro-phenyl 3-deoxy-3-[4-(4-thiazolyl)-1H-1,2,3-triazol-1-yl]-1-thio-α-D-galactopyranoside

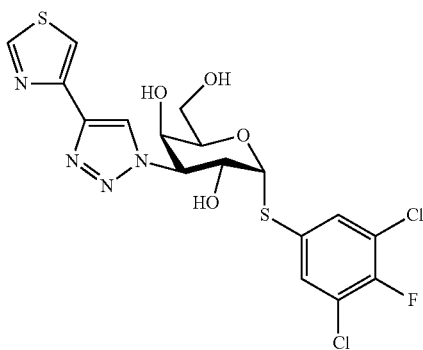

A solution of 3,5-dichloro-4-fluoro-phenyl 2,4,6-tri-O-acetyl-3-deoxy-3-[4-(4-thiazolyl)-1H-1,2,3-triazol-1-yl]-1-thio-α-D-galactopyranoside (30 mg, 0.05 mmol) in MeOH/TEA/H$_2$O (10/3/1) (2 mL) was stirred at room temperature for 20 h. The mixture was evaporated to dryness and the residue was purified by Prep-HPLC to afford product as a white solid (10 mg, 40.65%).

ESI-MS m/z calcd for $[C_{17}H_{15}Cl_2FN_4O_4S_2]^+$ [M+H]$^+$: 493.0; found: 493.0.

$^1$H NMR (400 MHz, MeOD-d4) δ 9.12 (d, J=1.5 Hz, 1H), 8.47 (s, 1H), 8.01 (d, J=1.6 Hz, 1H), 7.76 (d, J=6.3 Hz, 2H), 5.85 (d, J=5.3 Hz, 1H), 5.02 (dd, J=11.5, 2.6 Hz, 1H), 4.94 (dd, J=11.5, 5.6 Hz, 1H), 4.51 (t, J=6.0 Hz, 1H), 4.22 (d, J=1.8 Hz, 1H), 3.79-3.66 (m, 2H).

Example 15

5-Bromopyridin-3-yl 3-deoxy-3-[4-(2-methyl-4-thiazolyl)-1H-1,2,3-triazol-1-yl]-1-thio-α-D-galactopyranoside

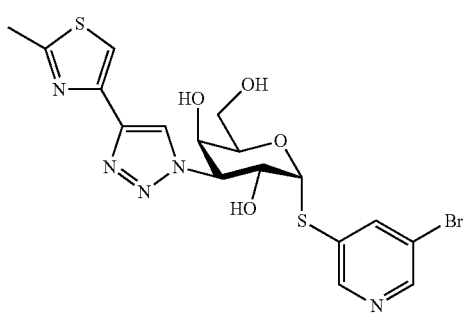

A solution of 5-Bromopyridin-3-yl 3-deoxy-3-[4-(2-methyl-4-thiazolyl)-1H-1,2,3-triazol-1-yl]-1-thio-α-D-galactopyranoside (30 mg, 0.05 mmol) in MeOH/TEA/H$_2$O (5/3/1) (1 mL) was stirred at room temperature for 20 h. The mixture was evaporated to dryness and the residue was purified by HPLC (H$_2$O/CH$_3$CN=40%) to afford the title compound as a white solid (10 mg, 40%).

m/z calcd for $[C_{17}H_{18}BrN_5O_4S_2]^+$ [M+H]$^+$: 500.0; found: 500.0.

$^1$H NMR (400 MHz, MeOD-d4) δ 8.58 (d, J=2.1 Hz, 1H), 8.42 (s, 1H), 8.35 (t, J=2.0 Hz, 1H), 7.77 (s, 1H), 5.93 (d, J=5.3 Hz, 1H), 5.05 (dd, J=11.4, 2.8 Hz, 1H), 4.96-4.91 (dd, J=11.4, 5.3 Hz, 1H), 4.51 (t, J=5.9 Hz, 1H), 4.23 (d, J=2.0 Hz, 1H), 3.78-3.67 (m, 2H), 2.78 (s, 3H).

Example 16

2,6-Dichloro-bensonitril-4-yl 3-deoxy-3-[4-(2-thiazolyl)-1H-1,2,3-triazol-1-yl]-1-thio-α-D-galactopyranoside

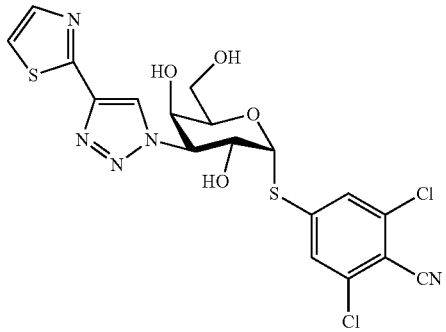

To a solution of 2,6-dichloro-bensonitril-4-yl 2,4,6-tri-O-acetyl-3-deoxy-3-[4-(2-thiazolyl)-1H-1,2,3-triazol-1-yl]-1-thio-α-D-galactopyranoside (4 mg, 0.01 mmol) in MeOH/TEA/H$_2$O (10/3/1) (2 mL) was held at room temperature with stirring on for 20 h. The mixture was evaporated to dryness and the residue was purified by Prep-HPLC to afford the title compound as a white solid (0.8 mg, 16%).

ESI-MS m/z calcd for $[C_{18}H_{15}Cl_2N_5O_4S_2]^-$ [M+H]$^-$: 500.0; found: 500.0.

$^1$H NMR (400 MHz, MeOD-d4) δ 8.49 (s, 1H), 7.79 (d, J=3.3 Hz, 1H), 7.72 (s, 2H), 7.54 (d, J=3.3 Hz, 1H), 6.08 (d, J=5.3 Hz, 1H), 4.97 (dd, J=11.5, 2.9 Hz, 2H), 4.87 (d, J=11.4, 5.3 Hz, 3H), 4.25 (t, J=5.7 Hz, 1H), 4.10 (d, J=2.4 Hz, 1H), 3.63-3.59 (m, 2H).

Example 17

3,4,5-Trichlorophenyl 3-deoxy-3-[4-(2-thiazolyl)-1H-1,2,3-triazol-1-yl]-1-thio-α-D-galactopyranoside

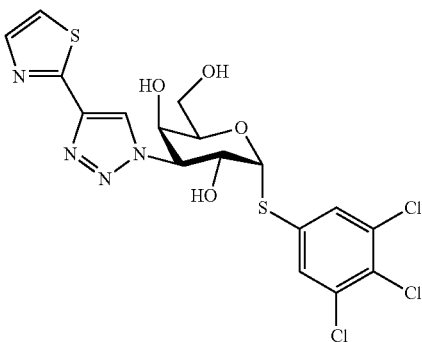

A solution of 1,3-dideoxy-2,4,6-tri-O-acetyl-1-(3,4,5-trichlorobenzenethiol)-3-[4-(thiazole-2-yl)-1H-1,2,3-triazol-1-yl]-D-galactopyranoside (30 mg, 0.05 mmol) in MeOH/TEA/H$_2$O (10/3/1) (2 mL) was stirred at room temperature for 20 h. The mixture was evaporated to dryness and the residue was purified by Prep-HPLC to afford product as a white solid. (2 mg, 21%).

ESI-MS m/z calcd for $[C_{17}H_{15}Cl_2FN_4O_4S_2]^+$ [M+H]$^+$: 509.0; found: 509.0.

$^1$H NMR (400 MHz, MeOD-d4) δ, 8.60 (s, 1H), 7.90 (d, J=3.2 Hz, 1H), 7.79 (s, 2H), 7.65 (d, J=3.2 Hz, 1H), 5.94 (d, J=5.2 Hz, 1H), 5.04 (dd, J=11.4, 2.7 Hz, 1H), 4.94 (dd, J=11.4, 5.2 Hz, 1H), 4.47 (t, J=6.1 Hz, 1H), 4.22 (d, J=2.0 Hz, 1H), 3.74-3.70 (m, 2H).

Example 18

3,4-Dichlorophenyl 3-deoxy-3-[4-(2-thiazolyl)-1H-1,2,3-triazol-1-yl]-1-thio-α-D-galactopyranoside

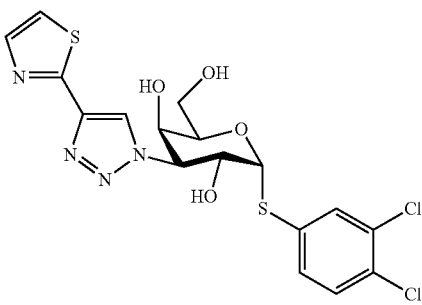

A solution of 3,4-Dichlorophenyl 2,4,6-tri-O-acetyl-3-deoxy-3-[4-(2-thiazolyl)-1H-1,2,3-triazol-1-yl]-1-thio-α-D-galactopyranoside (30 mg, 0.05 mmol) in MeOH/TEA/H$_2$O (10/3/1) (2 mL) was stirred at rt for 20 h. The mixture was evaporated to dryness and the residue was purified by Prep-HPLC to afford the product as a white solid. (10 mg, 41%).

ESI-MS m/z calcd for $[C_{17}H_{15}Cl_2FN_4O_4S_2]^+$ [M+H]$^+$: 475.0; found: 475.0.

1H NMR (400 MHz, McOD-d4) δ 8.48 (s, 1H), 7.79 (d, J=3.3 Hz, 1H), 7.70 (d, J=2.0 Hz, 1H), 7.54 (d, J=3.3 Hz, 1H), 7.44 (dd, J=8.4, 2.0 Hz, 1H), 7.38 (d, J=8.4 Hz, 1H), 5.75 (d, J=5.3 Hz, 1H), 4.94 (dd, J=11.4, 2.8 Hz, 1H), 4.79 (dd, J=11.4, 5.2 Hz, 1H), 4.39 (t, J=6.1 Hz, 1H), 4.12 (d, J=1.7 Hz, 1H), 3.68-3.54 (m, 2H).

Example 19

3,4,5-Trichlorophenyl 3-deoxy-3-[4-(1,3,4-thiadiazol-2-yl)-1H-1,2,3-triazol-1-yl]-1-thio-α-D-galactopyranoside

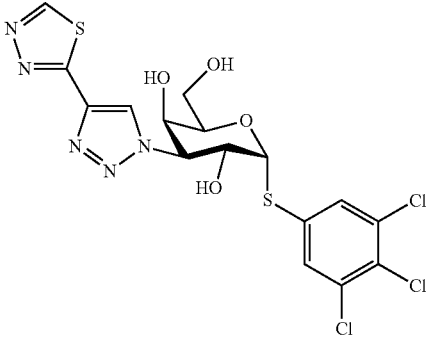

A solution of 3,4,5-Trichlorophenyl 2,4,6-tri-O-acetyl-3-deoxy-3-[4-(1,3,4-thiadiazol-2-yl)-1H-1,2,3-triazol-1-yl]-1-thio-α-D-galactopyranoside (30 mg, 0.05 mmol) in MeOH/TEA/H$_2$O (10/3/1) (2 mL) was stirred at room temperature for 20 h. The mixture was evaporated to dryness and the residue was purified by Prep-HPLC to afford the title compound as a white solid. (6 mg, 21%).

ESI-MS m/z calcd for $[C_{17}H_{15}Cl_2FN_4O_4S_2]^+$ [M+H]$^+$: 510.0; found: 510.0.

$^1$H NMR (400 MHz, MeOD-d4) δ 9.37 (s, 1H), 8.67 (s, 1H), 7.68 (s, 2H), 5.83 (d, J=5.2 Hz, 1H), 4.99 (dd, J=11.4, 2.7 Hz, 1H), 4.95 (dd, J=11.4, 5.2 Hz, 1H), 4.36 (t, J=6.1 Hz, 1H), 4.12 (d, J=2.0 Hz, 1H), 3.70-3.63 (m, 2H).

Example 20

5-Bromopyrdin-3-yl 3-deoxy-3-[4-(2-thiazolyl)-1H-1,2,3-triazol-1-yl]-1-thio-α-D-galactopyranoside

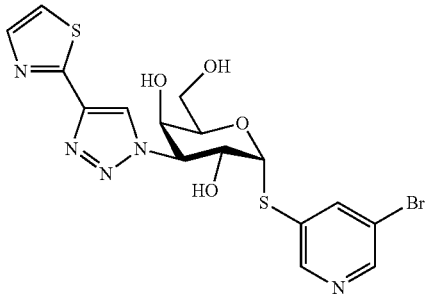

NaOMe (12.3 mg, 0.23 mmol) was added to a solution of 5-Bromopyridin-3-yl 2,4,6-tri-O-acetyl-3-deoxy-3-[4-(2-thiazolyl)-1H-1,2,3-triazol-1-yl]-1-thio-α-D-galactopyranoside (140 mg, 0.229 mmol) in methanol (6.00 mL). The mixture was stirred at room temperature overnight. The mixture was concentrated to a small volume. The residue was purified by chromatography on C-18 column using a gradient of $CH_3CN$/10 mM $NH_4HCO_3$ from 0-37% to afford 40.0 mg (36.0% yield) of the title compound as a white solid.

$^1$H NMR (400 MHz, MeOD) δ 8.70 (d, J=1.9 Hz, 1H), 8.61 (s, 1H), 8.58 (d, J=2.1 Hz, 1H), 8.35 (t, J=2.0 Hz, 1H), 7.91 (d, J=3.3 Hz, 1H), 7.66 (d, J=3.3 Hz, 1H), 5.94 (d, J=5.3 Hz, 1H), 5.09 (dd, J=11.4, 2.8 Hz, 1H), 4.95 (m, 1H), 4.51 (t, J=5.9 Hz, 1H), 4.24 (d, J=1.9 Hz, 1H), 3.79-3.56 (m, 2H). ESI-MS m/z calcd for $[C_{16}H_{17}BrN_5O_4S_2]^+$ $[M+H]^+$: 485.0; found: 485.0.

Example 21

5-Chloropyridin-3-yl 3-deoxy-3-[4-(2-thiazolyl)-1H-1,2,3-triazol-1-yl]-1-thio-α-D-galactopyranoside

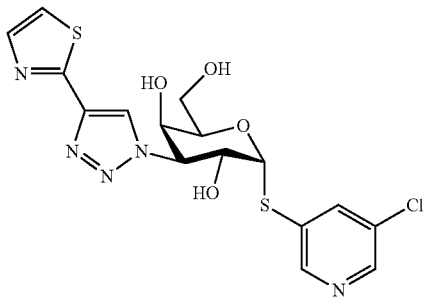

5-Chloropyridin-3-yl 2,4,6-tri-O-acetyl-3-deoxy-3-[4-(2-thiazolyl)-1H-1,2,3-triazol-1-yl]-1-thio-α-D-galactopyranoside (80.0 mg, 0.141 mmol) was dissolved in MeOH/Et$_3$N/H$_2$O (10/3/1) (5 mL), then it was stirred at room temperature for 4 h. The mixture was evaporated to dryness and the residue was triturated with ether and filtered to afford 53.0 mg (85%) of the title compound as a white solid $^1$H NMR (400 MHz, MeOD) δ 8.54 (d, J=1.9 Hz, 1H), 8.49 (s, 1H), 8.37 (d, J=2.2 Hz, 1H), 8.10 (t, J=2.1 Hz, 1H), 7.79 (d, J=3.3 Hz, 1H), 7.54 (d, J=3.3 Hz, 1H), 5.83 (d, J=5.3 Hz, 1H), 4.97 (dd, J=11.4, 2.8 Hz, 1H), 4.83 (dd, J=11.4, 5.4 Hz, 2H), 4.39 (t, J=6.2 Hz, 1H), 4.12 (d, J=2.1 Hz, 1H), 3.66-3.55 (m, 2H). ESI-MS m/z calcd for $[C_{19}H_{16}ClF_3N_4O_4S]^+$ $[M+H]^+$:442.0; found: 442.0.

Example 22

5-Bromo-2-cyano-pyridine-3-yl 3-deoxy-3-[4-(2-thiazolyl)-1H-1,2,3-triazol-1-yl]-1-thio-α-D-galactopyranoside

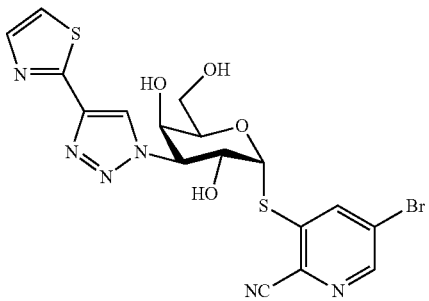

5-Bromo-2-cyano-pyridine-3-yl 2,4,6-tri-O-acetyl-3-deoxy-3-[4-(2-thiazolyl)-1H-1,2,3-triazol-1-yl]-1-thio-α-D-galactopyranoside (60.0 mg, 0.0941 mmol) was dissolved in MeOH/Et$_3$N/H$_2$O (10/3/1) (2 mL), The solution was stirred at room temperature for 4 h. The mixture was evaporated to dryness. The crude product was purified by prep-HPLC to afford 20.0 mg (42%) of the title compound as a white solid.

$^1$H NMR (400 MHz, MeOD) δ 8.69 (d, J=2.0 Hz, 1H), 8.62 (d, J=1.3 Hz, 2H), 7.91 (d, J=3.3 Hz, 1H), 7.66 (d, J=3.3 Hz, 1H), 6.24 (d, J=5.3 Hz, 1H), 5.15 (dd, J=11.3, 2.8 Hz, 1H), 5.01 (dd, J=11.3, 5.3 Hz, 1H), 4.39 (t, J=6.1 Hz, 1H), 4.25 (d, J=2.1 Hz, 1H), 3.72-3.67 (m, 2H). ESI-MS m/z calcd for $[C_{17}H_{15}BrN_6O_4S_2]^+$ $[M+H]^+$: 511.0; found: 511.0.

Example 23

5-Chloro-6-cyano-pyridine-3-yl 3-deoxy-3-[4-(2-thiazolyl)-1H-1,2,3-triazol-1-yl]-1-thio-α-D-galactopyranoside

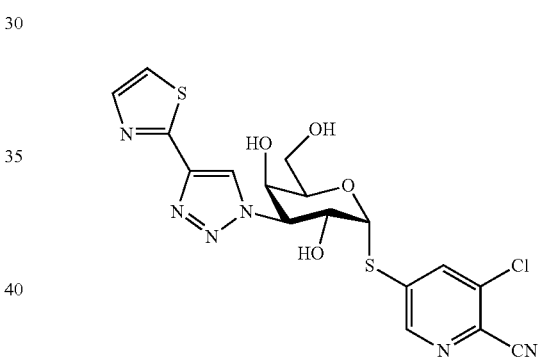

5-Chloro-6-cyano-pyridine-3-yl 2,4,6-tri-O-acetyl-3-deoxy-3-[4-(2-thiazolyl)-1H-1,2,3-triazol-1-yl]-1-thio-α-D-galactopyranoside (120 mg, 0.202 mmol) was dissolved in MeOH/Et$_3$N/H$_2$O (10/3/1)(3 mL), then the mixture was stirred at room temperature for 4 h. The mixture was evaporated to dryness. The crude product was purified by prep-HPLC to afford 40.0 mg (42%) of the title compound as a white solid. $^1$H NMR (400 MHz, MeOD) δ 8.74 (d, J=1.9 Hz, 1H), 8.61 (s, 1H), 8.36 (d, J=1.9 Hz, 1H), 7.91 (d, J=3.3 Hz, 1H), 7.66 (d, J=3.3 Hz, 1H), 6.23 (d, J=5.3 Hz, 1H), 5.12 (dd, J=11.4, 2.8 Hz, 1H), 4.99 (dd, J=11.4, 5.3 Hz, 2H), 4.37 (t, J=6.1 Hz, 1H), 4.22 (d, J=2.1 Hz, 1H), 3.71 (d, J=6.0 Hz, 2H). ESI-MS m/z calcd for $[C_{17}H_{15}ClN_6O_4S_2]^+$ $[M+H]^+$: 467.0; found: 467.0.

Example 24

3,5-Dichlorophenyl 3-deoxy-3-[4-(2-thiazolyl)-1H-1,2,3-triazol-1-yl]-1-thio-α-D-galactopyranoside

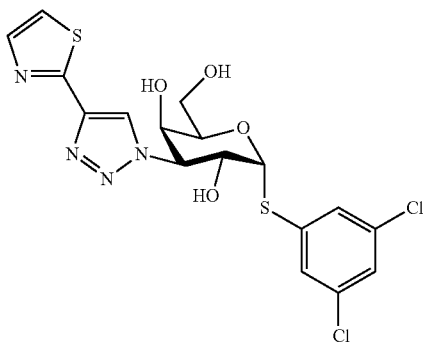

NaOMe (13.5 mg, 0.249 mmol) was added to a solution of 3,5-dichlorophenyl 2,4,6-tri-O-acetyl-3-deoxy-3-[4-(2-thiazolyl)-1H-1,2,3-triazol-1-yl]-1-thio-α-D-galactopyranoside (150 mg, 0.249 mmol) in methanol (10.0 mL). The mixture was stirred at room temperature over night. The mixture was concentrated to a small volume. The residue was purified by chromatography on C-18 column using a gradient of $CH_3CN$/10 mM $NH_4HCO_3$ from 0-37% to afford 70.0 mg (59.0%) of the title compound as a white solid.
$^1$H NMR (400 MHz, MeOD) δ 8.60 (s, 1H), 7.91 (d, J=3.3 Hz, 1H), 7.66 (d, J=3.3 Hz, 1H), 7.62 (d, J=1.8 Hz, 2H), 7.39 (t, J=1.8 Hz, 1H), 5.93 (d, J=5.3 Hz, 1H), 5.05 (dd, J=11.4, 2.8 Hz, 1H), 4.95 (m, 1H), 4.49 (t, J=6.2 Hz, 1H), 4.23 (d, J=1.7 Hz, 1H), 3.73 (m, J=11.4, 6.1 Hz, 2H). ESI-MS m/z calcd for $[C_{17}H_{17}Cl_2N_4O_4S_2]^+$ $[M+H]^+$: 475.0; found: 475.0.

Example 25

3-Bromo-4-chlorophenyl 3-deoxy-3-[4-(2-thiazolyl)-1H-1,2,3-triazol-1-yl]-1-thio-α-D-galactopyranoside

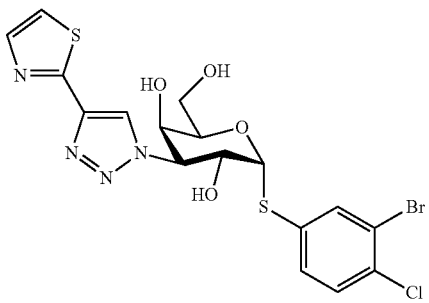

3-Bromo-4-chlorophenyl 2,4,6-tri-O-acetyl-3-deoxy-3-[4-(2-thiazolyl)-1H-1,2,3-triazol-1-yl]-1-thio-α-D-galactopyranoside (150 mg, 0.232 mmol) was dissolved in MeOH/$Et_3N$/$H_2O$ (0.5/0.3/0.1) (5 mL). The mixture was stirred at room temperature overnight for 4 h. The mixture was evaporated to dryness. The crude product was purified by Prep-HPLC to afford 52.3 mg (43.3%) of the title compound as a white solid. $^1$H NMR (400 MHz, MeOD) δ 8.60 (s, 1H), 7.97 (d, J=2.1 Hz, 1H), 7.91 (d, J=3.3 Hz, 1H), 7.66 (d, J=3.3 Hz, 1H), 7.60 (dd, J=8.4, 2.1 Hz, 1H), 7.50 (d, J=8.4 Hz, 1H), 5.86 (d, J=5.3 Hz, 1H), 5.05 (dd, J=11.4, 2.8 Hz, 1H), 4.95-4.91 (m, 1H), 4.51 (t, J=6.1 Hz, 1H), 4.24 (d, J=1.9 Hz, 1H), 3.73 (qd, J=11.5, 6.1 Hz, 2H).
ESI-MS m/z calcd for $[C_{17}H_{16}BrClN_4O_4S_2]^+$ $[M+H]^+$: 517.9; found: 519.0.

Example 26

5-Bromo-6-trifluoromethyl-pyridine-3-yl 3-deoxy-3-[4-(2-thiazolyl)-1H-1,2,3-triazol-1-yl]-1-thio-α-D-galactopyranoside

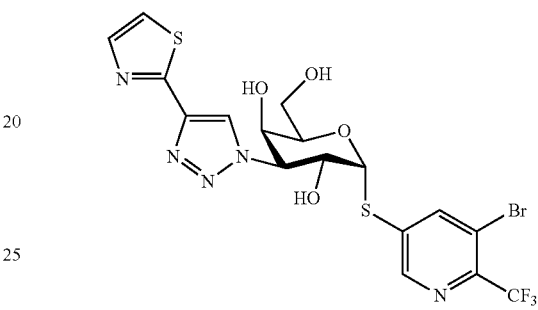

5-Bromo-6-trifluoromethyl-pyridine-3-yl 2,4,6-tri-O-acetyl-3-deoxy-3-[4-(2-thiazolyl)-1H-1,2,3-triazol-1-yl]-1-thio-α-D-galactopyranoside (66.0 mg, 0.0970 mmol) was dissolved in MeOH/$Et_3N$/$H_2O$ (0.5/0.3/0.1)(5 mL) and stirred at room temperature for 4 h. The reaction mixture was evaporated to dryness and the crude product was purified by prep-HPLC to afford 18.6 mg (34.6%) of the title compound as a white solid. $^1$H NMR (400 MHz, MeOD) δ 8.65 (d, J=1.8 Hz, 1H), 8.49 (s, 1H), 8.41 (d, J=1.3 Hz, 1H), 7.79 (d, J=3.3 Hz, 1H), 7.54 (d, J=3.3 Hz, 1H), 6.03 (d, J=5.3 Hz, 1H), 5.00 (dd, J=11.4, 2.8 Hz, 1H), 4.87 (dd, J=11.4, 5.3 Hz, 1H), 4.31 (t, J=6.0 Hz, 1H), 4.12 (d, J=2.0 Hz, 1H), 3.62-3.59 (m, 2H). ESI-MS m/z calcd for $[C_{17}H_{15}BrF_3N_5O_4S_2]^+$ $[M+H]^+$: 553.0; found: 554.0.

Example 27

3-Bromo-4-fluoro-phenyl 3-deoxy-3-[4-(2-thiazolyl)-1H-1,2,3-triazol-1-yl]-1-thio-α-D-galactopyranoside

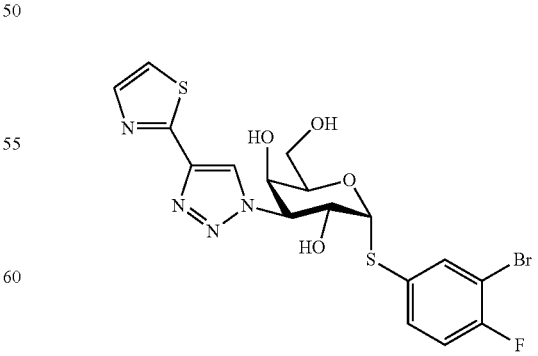

NaOMe (7.04 mg, 0.130 mmol) was added to a solution of 3-Bromo-4-fluoro-phenyl 2,4,6-tri-O-acetyl-3-deoxy-3-[4-(2-thiazolyl)-1H-1,2,3-triazol-1-yl]-1-thio-α-D-galactopyranoside (82.0 mg, 0.130 mmol) in methanol (10.00 mL). The mixture was stirred at room temperature overnight. The mixture was concentrated to a small volume. The residue was purified by chromatography on C-18 column using a gradient of $CH_3CN$/10 mM $NH_4HCO_3$ from 0-44% to give the title compound as a white solid, 43.0 mg (65.6%).

ESI-MS m/z calcd for $[C_{17}H_{16}BrFN_4O_4S_2]^+$ $[M+H]^+$: 502.0; found: 503.0.

$^1$H NMR (400 MHz, MeOD) δ 8.59 (s, 1H), 7.93 (dd, J=6.6, 2.2 Hz, 1H), 7.91 (d, J=3.3 Hz, 1H), 7.68-7.61 (m, 2H), 7.22 (t, J=8.7 Hz, 1H), 5.77 (d, J=5.3 Hz, 1H), 5.04 (dd, J=11.3, 2.8 Hz, 1H), 4.94-4.97 (m, 1H), 4.55 (t, J=5.9 Hz, 1H), 4.23 (s, 1H), 3.80-3.64 (m, 2H).

Example 28

2,5-Dichlorophenyl 3-deoxy-3-[4-(2-thiazolyl)-1H-1,2,3-triazol-1-yl]-1-thio-α-D-galactopyranoside

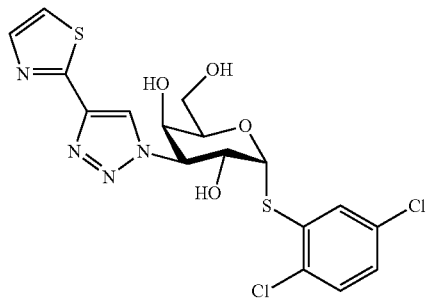

NaOMe (15.3 mg, 0.283 mmol) was added to a solution of 2,5-Dichlorophenyl 2,4,6-tri-O-acetyl-3-deoxy-3-[4-(2-thiazolyl)-1H-1,2,3-triazol-1-yl]-1-thio-α-D-galactopyranoside (170 mg, 0.283 mmol) in methanol (6.00 mL). The mixture was stirred at room temperature over night. The mixture was concentrated to a small volume. The residue was purified by chromatography on C-18 column using a gradient of $CH_3CN$/10 mM $NH_4HCO_3$ from 0-42% to afford the title compound as a white solid, 53.0 mg (39.4%).

$^1$H NMR (400 MHz, MeOD) δ 8.50 (s, 1H), 7.79 (d, J=3.3 Hz, 1H), 7.72 (d, J=2.4 Hz, 1H), 7.54 (d, J=3.3 Hz, 1H), 7.33 (d, J=8.6 Hz, 1H), 7.16 (dd, J=8.6, 2.4 Hz, 1H), 5.93 (d, J=5.4 Hz, 1H), 5.01 (dd, J=11.4, 2.8 Hz, 1H), 4.87 (dd, J=11.4, 5.4 Hz, 1H), 4.33 (t, J=6.2 Hz, 1H), 4.14 (d, J=2.0 Hz, 1H), 3.62 (dd, J=11.3, 6.1 Hz, 1H), 3.52 (dd, J=11.3, 6.4 Hz, 1H). ESI-MS m/z calcd for $[C_{17}H_{17}Cl_2N_4O_4S_2]^+$ $[M+H]^+$: 475.0; found: 475.0.

Example 29

3,4-dichlorophenyl 3-deoxy-3-[4-(4-bromo-2-thiazol-2-yl)-1H-1,2,3-triazol-1-yl]-1-thio-α-D-galactopyranoside

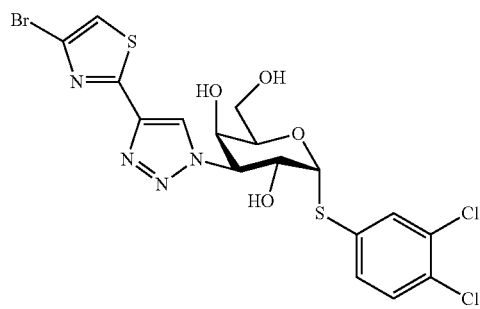

3,4-Dichlorophenyl 2,4,6-tri-O-acetyl-3-deoxy-3-[4-(2-thiazolyl)-1H-1,2,3-triazol-1-yl]-1-thio-α-D-galactopyranoside (120 mg, 0.176 mmol) was dissolved in MeOH/$Et_3$N/$H_2$O (0.5/0.3/0.1) (3 mL), then the mixture was stirred at room temperature for 4 h. The mixture was evaporated to dryness and the crude product was purified by Prep-HPLC to afford the title compound as a white solid, 50.0 mg (51.1%).

$^1$H NMR (400 MHz, MeOD) δ 8.62 (s, 1H), 7.82 (d, J=2.0 Hz, 1H), 7.61 (s, 1H), 7.56-7.52 (m, 1H), 7.50 (d, J=8.4 Hz, 1H), 5.86 (d, J=5.3 Hz, 1H), 5.05 (dd, J=11.4, 2.8 Hz, 1H), 4.92 (dd, J=11.5, 5.4 Hz, 6H), 4.51 (t, J=6.2 Hz, 1H), 4.23 (d, J=2.0 Hz, 1H), 3.73 (qd, J=11.5, 6.1 Hz, 2H). ESI-MS m/z calcd for $[C_{17}H_{15}BrCl_2N_4O_4S_2]^-$ $[M-H]^-$: 551.9; found: 553.0.

Example 30

3,4-Dichlorophenyl 3-deoxy-3-[4-(5-fluoro-thiazol-2-yl)-1H-1,2,3-triazol-1-yl]-1-thio-α-D-galactopyranoside

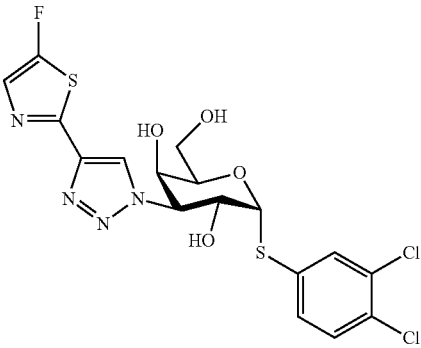

3,4-Dichlorophenyl 2,4,6-tri-O-acetyl-3-deoxy-3-[4-(5-fluoro-thiazol-2-yl)-1H-1,2,3-triazol-1-yl]-1-thio-α-D-galactopyranoside (100 mg, 0.161 mmol) was dissolved in MeOH/$Et_3$N/$H_2$O (0.5/0.3/0.1) (5 mL). The mixture was stirred at room temperature for 4 h. The solvents were removed in vacuo to afford crude product, which was purified by Prep-HPLC to give the title compound as a grey solid, 18.29 mg (23.0%).

$^1$H NMR (400 MHz, MeOD) δ 8.54 (s, 1H), 7.80 (d, J=2.0 Hz, 1H), 7.53 (dd, J=7.9, 2.6 Hz, 2H), 7.48 (d, J=8.4 Hz, 1H), 5.84 (d, J=5.3 Hz, 1H), 5.02 (dd, J=11.5, 2.9 Hz, 2H), 4.90 (d, J=5.4 Hz, 1H), 4.48 (t, J=6.2 Hz, 1H), 4.20 (d, J=2.0 Hz, 1H), 3.71 (qd, J=11.4, 6.1 Hz, 2H). ESI-MS m/z calcd for $[C_{17}H_{15}Cl_2FN_4O_4S_2]^+$ [M+H]$^+$: 493.0; found: 493.0.

Example 31

3,4-Dichlorophenyl 3-deoxy-3-[4-(4-chloro-thiazol-2-yl)-1H-1,2,3-triazol-1-yl]-1-thio-α-D-galactopyranoside

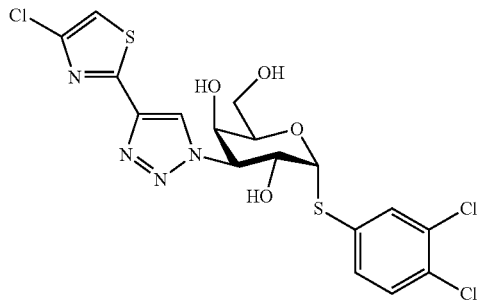

A solution of 3,4-Dichlorophenyl 2,4,6-tri-O-acetyl-3-deoxy-3-[4-(4-chloro-thiazol-2-yl)-1H-1,2,3-triazol-1-yl]-1-thio-α-D-galactopyranoside (70.0 mg, 0.110 mmol) in MeOH/Et$_3$N/H$_2$O (1/0.6/0.2) (1.8 mL) was stirred at room temperature for 4 h. The solvents were removed in vacuo to afford crude product, which was purified by Prep-HPLC to give the title compound as a white solid, 10.4 mg (18.6%).

$^1$H NMR (400 MHz, MeOD) δ 8.49 (s, 1H), 7.70 (d, J=2.0 Hz, 1H), 7.46-7.35 (m, 3H), 5.75 (d, J=5.3 Hz, 1H), 4.93 (dd, J=11.5, 2.8 Hz, 1H), 4.81 (dd, J=10.7, 4.7 Hz, 2H), 4.39 (t, J=6.2 Hz, 1H), 4.11 (d, J=2.1 Hz, 1H), 3.64-3.57 (m, 2H). ESI-MS m/z calcd for $[C_{17}H_{15}Cl_3N_4O_4S_2]^+$ [M+H]$^+$: 509.0; found: 509.0.

Example 32

3,4-Dichlorophenyl 3-deoxy-3-[4-(4-trifluoromethyl-thiazol-2-yl)-1H-1,2,3-triazol-1-yl]-1-thio-α-D-galactopyranoside

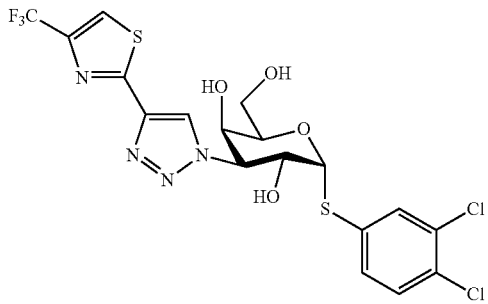

3,4-Dichlorophenyl 2,4,6-tri-O-acetyl-3-deoxy-3-[4-(4-trifluoromethyl-thiazol-2-yl)-1H-1,2,3-triazol-1-yl]-1-thio-α-D-galactopyranoside (110 mg, 0.164 mmol) was dissolved in MeOH/Et$_3$N/H$_2$O (0.5/0.3/0.1) (1.8 mL). The mixture was stirred at room temperature for 4 h. The solvents were removed in vacuo to afford crude product, which was purified by Prep-HPLC to give the title compound as a white solid, 18.6 mg (20.9%). $^1$H NMR (400 MHz, MeOD) δ 8.58 (s, 1H), 8.10 (s, 1H), 7.70 (d, J=2.0 Hz, 1H), 7.42 (dt, J=21.4, 5.2 Hz, 2H), 5.75 (d, J=5.3 Hz, 1H), 4.95 (dd, J=11.4, 2.9 Hz, 2H), 4.85-4.81 (m, 1H), 4.40 (t, J=5.9 Hz, 1H), 4.12 (d, J=2.1 Hz, 1H), 3.64-3.58 (m, 2H). ESI-MS m/z calcd for $[C_{18}H_{15}ClF_3N_4O_4S_2]^+$ [M+H]$^+$: 543.0; found: 543.0.

Synthesis of Intermediates i1-i19 i1) 3,4-Dichlorophenyl 2,4,6-tri-O-acetyl-3-deoxy-3-[4-(3-thiophenyl)-1H-1,2,3-triazol-1-yl]-1-thio-α-D-galactopyranoside

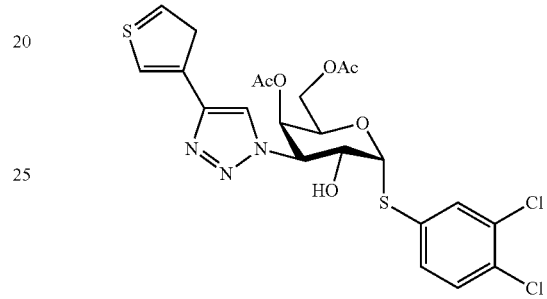

3,4-Dichlorophenyl 2,4,6-tri-O-acetyl-3-azido-3-deoxy-1-thio-α-D-galactopyranoside (200 mg, 0.41 mmol) and 3-ethynylthiophene (43.9 mg, 0.41 mmol) were dissolved in CH$_3$CN (20 mL). Then Copper(I)Iodide (23.2 mg, 0.12 mmol) and TEA (205.5 mg, 2.03 mmol) were added. The mixture was stirred at rt over night. The mixture was concentrated and the residue was purified on silica gel using a gradient of EtOAc/PE from 0-30% to give 100 mg (41%) of the title compound.

ESI-MS m/z calcd for $[C_{24}H_{24}Cl_2N_3O_7S_2]^+$ (M+H)$^+$: 600.0; found: 600.0.

i2) 2-Chloro-5-fluoro-benzonitril-4-yl 2,4,6-tri-O-acetyl-3-deoxy-3-[4-(3-thiophenyl)-1H-1,2,3-triazol-1-yl]-α-D-galactopyranoside 2-chloro-5-fluoro-4-mercaptobenzonitrile

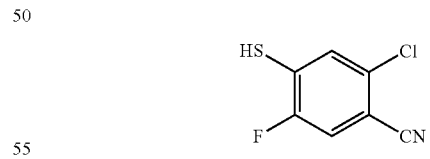

To a solution of 2-chloro-4,5-difluorobenzonitrile (500 mg, 2.88 mmol) in DMF (10 mL) was added Na$_2$S.9H$_2$O (1.03 g, 4.32 mmol). The reaction was stirred at room temperature for 20 h. The mixture was added NaHSO$_4$ (aq) to adjust to pH 4-5 followed by addition of MTBE (20 mL). The organic phase was washed with water (30 mL) and brine (30 mL), dried over anhydrous sodium sulphate. Removal of solvents gave the crude product which was used immediately in the next step.

m/z calcd for $[C_7H_3ClFNS]^-$ [M-H]$^-$: 186.0; found: 186.0.

2-Chloro-5-fluoro-benzonitril-4-yl 2,4,6-tri-O-acetyl-3-azido-3-deoxy-1-thio-α-D-galactopyranoside

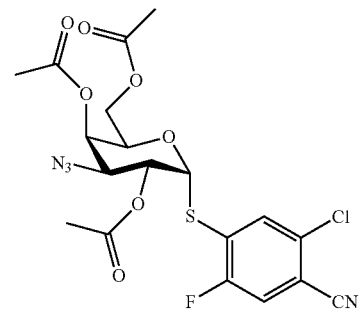

To a solution of 2-chloro-5-fluoro-4-mercaptobenzonitrile (450 mg, 2.41 mmol) in DMF (10 mL) was added NaH (92 mg, 2.30 mmol) at 0° C. After 10 min, 2,4,6-tri-O-acetyl-3-azido-1-chloro-3-deoxy-β-D-galactopyranoside (500 mg, 1.44 mmol) was added. The mixture was stirred at room temperature for 4 h. Water (30 mL) and DCM (30 mL) were added. The aqueous phase was extracted with DCM (30 mL×2), the combined organic phases were washed with water (30 mL) and brine (30 mL), dried over anhydrous sodium sulphate. Removal of solvent gave a residue. The residue was purified by column chromatography (PE/EA=3/1) to obtain the title product (230 mg, 32%).

m/z calcd for $[C_{19}H_{18}ClFN_4O_7S]^-$ $[M+H]^+$: 501.0; found: 501.0.

2-Chloro-5-fluoro-benzonitril-4-yl 2,4,6-tri-O-acetyl-3-deoxy-3-[4-(3-thiophenyl)-1H-1,2,3-triazol-1-yl]-1-thio-α-D-galactopyranoside

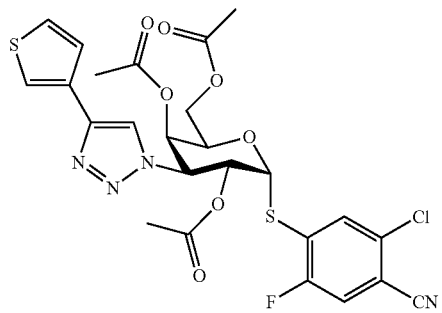

To a solution of 2-Chloro-5-fluoro-benzonitril-4-yl 2,4,6-tri-O-acetyl-3-azido-3-deoxy-1-thio-α-D-galactopyranoside (230 mg, 0.46 mmol) in DMF (5 mL) were added DIPEA (0.4 mL), Copper(I)Iodide (26 mg, 0.14 mmol), 3-ethynylthiophene (75 mg, 0.69 mmol). The reaction was stirred at room temperature for 20 h under $N_2$. Water (20 mL) and DCM (20 mL) were added. The aqueous phase was extracted with DCM (20 mL×2), the combined organic phase was washed with water (40 mL) and brine (40 mL), dried over anhydrous sodium sulphate. Removal of solvent gave a residue. The residue was purified by column chromatography (PE/EA=2/1) to obtain the desired product (150 mg, 54%).

m/z calcd for $[C_{25}H_{22}ClFN_4O_7S_2]^+$ $[M+H]^+$: 609.0; found: 609.0.

i3) 5-Bromopyridin-3-yl 2,4,6-tri-O-acetyl-3-deoxy-3-[4-(3-thiophenyl)-1H-1,2,3-triazol-1-yl]-1-thio-α-D-galactopyranoside

O-[(5-bromo-3-pyridyl)]N,N-dimethylcarbamothioate

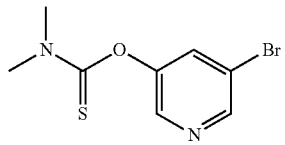

To a solution of 5-bromopyridin-3-ol (17.4 g, 0.10 mol) in DMF (0.15 L) was added sodium hydride (2.64 g, 0.11 mol, 96% in mineral oil) at 0° C., followed by stirring at 0° C. for 30 min. Dimethylthiocarbamoyl chloride (14.83 g, 0.12 mol) was added to the reaction mixture followed by stirring at room temperature over night. LC-MS analysis indicated formation of the target compound. The reaction mixture was quenched with water (100 mL) followed by extraction with EtOAc (100 mL×3). The combined organic layers were washed with brine (100 mL), dried over $Na_2SO_4$ and concentrated in vacuo. The crude product was purified by flash chromatography (EtOAc/PE=5%~40%, ISCO® 120 g, 50 mL/min, normal phase silica gel, uv254) to afford the target compound (9.93 g, 36.5% yield) as yellow oil.

ESI-MS m/z calcd for $[C_8H_9BrN_2OS]^-$ $[M+H]^+$: 261.0; found: 261.0.

S-[(5-bromo-3-pyridyl)] N,N-dimethylcarbamothioate

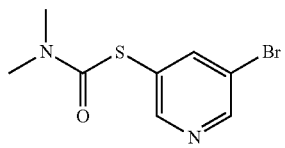

O-[(5-bromo-3-pyridyl)] N,N-dimethylcarbamothioate (9.93 g, 0.04 mol) was dissolved in phenoxybenzene (100 mL). The mixture was heated at reflux for 2 h. The reaction mixture was cooled to room temperature and directly purified by flash chromatography on a Biotage (EtOAc/PE=5%~50%, ISCO 120 g, 50 mL/min, normal phase silica gel, uv 254) to afford the target compound (4.63 g, 44% yield) as a yellow solid.

ESI-MS m/z calcd for $[C_8H_9BrN_2OS]^-$ $[M+H]^+$: 261.0; found: 261.0.

3-bromo-5-methoxy-benzenethiol

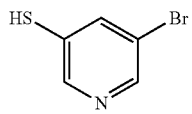

S-(3-chloro-5-methoxy-phenyl) N,N-dimethylcarbamothioate (1.044 g, 4 mmol) and KOH (897.21 mg, 16 mmol) was taken up in ethanol/water (40 mL, 3/1). The reaction mixture was heated at reflux for 2 h. LC-MS analysis indicated total consumption of the starting material. The mixture was concentrated followed by addition of 10% aq NaOH (30 mL). The reaction mixture was washed with ether (15 mL×3). The aqueous layer was acidified with aq KHSO$_4$ to adjust the pH~2, followed by extraction with EtOAc (20 mL×5). The combined organic layers were washed with brine, dried over Na$_2$SO$_4$ and concentrated in vacuo to afford crude product, which was used for next step directly without further purification.

ESI-MS m/z calcd for [C$_5$H$_4$BrNS]$^-$ [M−H]$^-$: 188.9; found: 188.0.

5-Bromopyridin-3-yl 2,4,6-tri-O-acetyl-3-azido-3-deoxy-1-thio-α-D-galactopyranoside

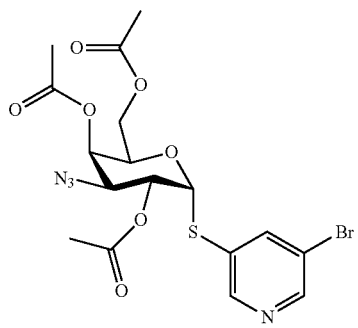

NaH (82.99 mg, 3.47 mmol) was added to a solution of 5-bromopyridine-3-thiol (658.67 mg, 3.47 mmol) in DMF (10 mL) at 0° C. The solution was stirred at rt for 30 min. Then 2,4,6-tri-O-acetyl-3-azido-1-chloro-3-deoxy-D-galactopyranoside (1.01 g, 2.89 mmol) was added. The reaction mixture was stirred at 50° C. for 2 h followed by cooling to room temperature. Water (50 mL) was added and the reaction mixture was extracted with EtOAc (15 mL×3). The combined organic layers were washed with brine, dried over Na$_2$SO$_4$ and concentrated in vacuo to afford crude product, which was purified by flash chromatography (EtOAc/PE=5%~40%, ISCO® 40 g, 30 mL/min, normal phase silica gel, uv 254) to afford the title compound (650 mg, 44.7% yield) as a white solid.

ESI-MS m/z calcd for [C$_{17}$H$_{19}$BrN$_4$O$_7$S]$^+$ [M+H]$^+$: 503.0; found: 503.0.

5-Bromopyridin-3-yl 2,4,6-tri-O-acetyl-3-deoxy-3-[4-(3-thiophenyl)-1H-1,2,3-triazol-1-yl]-1-thio-α-D-galactopyranoside

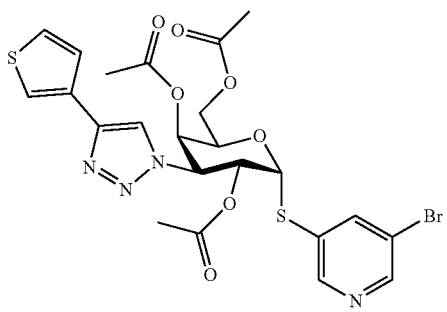

5-Bromopyridin-3-yl 2,4,6-tri-O-acetyl-3-azido-3-deoxy-1-thio-α-D-galactopyranoside (200 mg, 0.4 mmol), TEA (120.63 mg, 1.19 mmol) and 3-ethynylthiophene (85.96 mg, 0.79 mmol) were dissolved in CH$_3$CN (5 mL). Copper(I) Iodide (22.7 mg, 0.12 mmol) was added. The mixture was stirred at rt for 4 hours. Then the mixture was concentrated and the residue was purified on silica gel column using a gradient of EA/PE from 0-40% to give the title compound 150 mg (62%).

ESI-MS m/z calcd for [C$_{23}$H$_{24}$BrN$_4$O$_7$S$_2$]$^+$ (M+H)$^+$: 611.0; found: 611.0.

i5) 3,5-Dichloro-4-fluoro-phenyl 2,4,6-tri-O-acetyl-3-deoxy-3-[4-(3-thiazolyl)-1H-1,2,3-triazol-1-yl]-1-thio-α-D-galactopyranoside 2-((Trimethylsilyl)ethynyl)thiazole

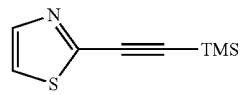 [SMILES: C[Si](C)(C)C#Cc1nccs1]

To a solution of 2-bromothiazole (500 mg, 3.07 mmol) in CH$_3$CN (10 mL) was added CuI (175 mg, 0.92 mmol), DIPEA (2.5 mL), Pd(PPh$_3$)$_2$Cl$_2$ (214 mg, 0.31 mmol). The mixture was heated under N$_2$ at 50° C. for 20 h. Removal of solvent gave a residue. The residue was purified by column chromatography (PE/EA=10/1) to obtain title compound (400 mg, 36%).

S-3,5-Dichloro-4-fluorophenyl O-ethyl carbonodithioate

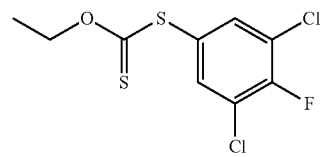

3,5-dichloro-4-fluoroaniline (1.0 g, 5.59 mmol) was dissolved in 10 ml HCl at 0° C., NaNO$_2$ (386 mg, 5.59 mmol) dissolved in water was added slowly and the solution was stirred at 0° C. until the solution was clear. The reaction mixture was slowly added a stirred solution of Potassium ethyl xantogenate (1.34 g, 8.38 mmol) in 15 ml water at 50° C. The reaction mixture was stirred at 70° C. for 2 h followed by extraction with EtOAc (100 mL). The organic phase was washed by brine, dried over Na$_2$SO$_4$, filtered and concentrated to give 1 g crude product which was immediately used in the next step.

3,5-Dichloro-4-fluorobenzenethiol

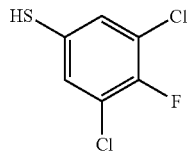

S-3,5-dichloro-4-fluorophenyl O-ethyl carbonodithioate (1 g, 3.52 mmol) was dissolved in 20 ml ethanol and heated to 85° C. KOH (0.98 g, 20 mmol) was added slowly followed by stirring at 85° C. for 2 h. pH was adjusted to 4~5 with HCl followed by and the reaction mixture was extracted using Ethyl acetate (20 mL×2). This gave after removal of solvents the title compound (400 mg, 58%)

ESI-MS m/z calcd for [C$_6$H$_3$Cl$_2$FS]$^-$ [M+H]$^-$: 195.0; found: 195.0.

3,5-Dichloro-4-fluoro-phenyl 2,4,6-tri-O-acetyl-3-azido-3-deoxy-1-thio-α-D-galactopyranoside

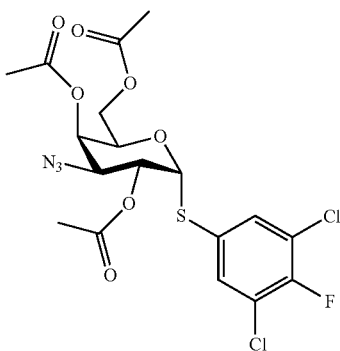

NaH (90 mg, 2.24 mmol) was added to a solution of 3,5-dichloro-4-fluorobenzenethiol (400 mg, 2.04 mmol) in DMF (10 mL) at 0° C. The solution was stirred at room temperature for 30 min. Then 2,4,6-tri-O-acetyl-3-azido-1-chloro-3-deoxy-3-D-galactopyranoside (570 mg, 1.63 mmol) was added to mixture. The reaction was stirred at 50° C. for 2 h. The reaction mixture was cooled to room temperature and water (20 mL) was added followed by extraction with EtOAc (15 mL×3). The combined organic layers were washed with brine, dried over Na$_2$SO$_4$ and concentrated in vacuo to afford crude product. This was purified by flash chromatography (EA/PE=5%~40%, ISCO 40 g, 30 mL/min, normal phase silica gel, UV254) to afford the target compound (150 mg, 18% yield) as a white solid.

ESI-MS m/z calcd for [C$_{18}$H$_{18}$Cl$_2$FN$_3$O$_7$S]$^+$ [M+H]$^+$: 510.0; found: 510.0.

3,5-Dichloro-4-fluoro-phenyl 2,4,6-tri-O-acetyl-3-deoxy-3-[4-(3-thiazolyl)-1H-1,2,3-triazol-1-yl]-1-thio-α-D-galactopyranoside

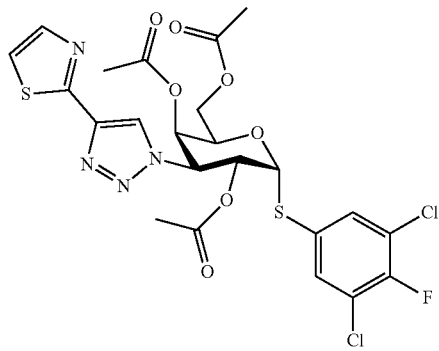

3,5-Dichloro-4-fluoro-phenyl 2,4,6-tri-O-acetyl-3-azido-3-deoxy-1-thio-α-D-galactopyranoside (50 mg, 0.10 mmol) in DMF (3 mL) were added TEA (0.10 mL), Copper(I) Iodide (6 mg, 0.03 mmol), CsF (24 mg, 0.15 mmol), 2-((trimethylsilyl)ethynyl)thiazole (28 mg, 0.15 mmol). The reaction was stirred at room temperature for 20 h under N$_2$ atmosphere. Water (10 mL) and DCM (10 mL) were added. The aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1) to obtain the desired product (30 mg, 48.5%).

ESI-MS m/z calcd for [C$_{23}$H$_{21}$Cl$_2$FN$_4$O$_7$S$_2$]$^+$ [M+H]$^+$: 619.0; found: 619.0.

i6) 2-(5-Fluoro-2-pyridyl)ethynyl-trimethyl-silane

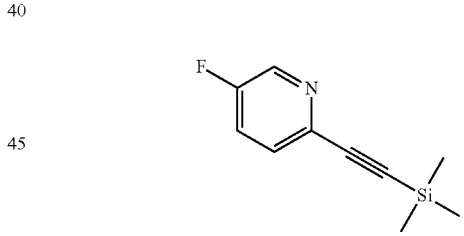

To a solution of 2-bromo-5-fluoro-pyridine (1000 mg, 5.68 mmol) in tetrahydrofuran (20 mL) was added ethynyl (trimethyl)silane (1.12 g, 11.36 mmol), [(C$_6$H$_5$)$_3$P]$_2$PdCl$_2$ (398.8 mg, 0.57 mmol) and Copper(I)Iodide (216.4 mg, 1.14 mmol). The reaction vessel was purged 3 times with nitrogen. Then DIPEA (1.470 g, 11.4 mmol) was added to the mixture. The reaction mixture was stirred at 60° C. for 20 h. The reaction was quenched with water (20 mL). The reaction mixture was extracted with dichloromethane (50 mL×3) and the combined organics were washed with brine (20 mL×1). The material was dried over Na$_2$SO$_4$, filtered, and evaporated. The crude product was purified by flash chromatography on a combiflash (PE, ISCO 40 g, 40 ml/min, normal phase silica, uv254) to afford the title compound 920 mg (84%) as brown oil.

m/z calcd for [C$_{10}$H$_{12}$FNSi]$^+$ [M+H]: 194.0; found: 194.0.

2,4,6-tri-O-acetyl-3-azido-1-chloro-3-deoxy-β-D-galactopyranoside

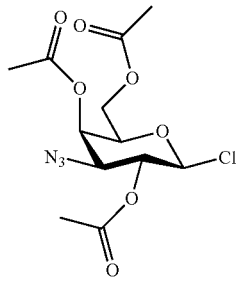

To a stirred suspension of 1,2,4,6-tetra-O-acetyl-3-azido-3-deoxy-β-D-galactopyranoside (5.0 g, 13.39 mmol), Phosphorus pentachloride (3.07 g, 14.7 mmol) in dry methylene chloride (50 mL), boron trifluoride dimethyl etherate (76.3 mg, 0.67 mmol) was added. After stirring for 30 min, the reaction mixture was diluted with DCM (120 mL×2) and then washed with ice-cold water (60 mL×3), saturated ice-cold NaHCO$_3$ solution (2×50 mL), and again ice cold water (30 mL×2), dried over anhydrous Na$_2$SO$_4$ and evaporated under reduced pressure. The residue was co-evaporated with toluene to give the title compound 4510 mg (96%) as a white solid.

$^1$H NMR (500 MHz, CDCl$_3$) δ 5.48 (d, J=2.5 Hz, 1H), 5.38-5.28 (m, 1H), 5.24 (d, J=8.7 Hz, 1H), 4.18 (dd, J=11.6, 6.0 Hz, 1H), 4.10 (dd, J=11.6, 6.8 Hz, 1H), 4.02-3.94 (m, 1H), 3.61 (dd, J=10.3, 3.3 Hz, 1H), 2.20 (s, 3H), 2.17 (s, 3H), 2.08 (s, 3H).

3,4-Dichlorophenyl 2,4,6-tri-O-acetyl-3-azido-3-deoxy-1-thio-α-D-galactopyranoside

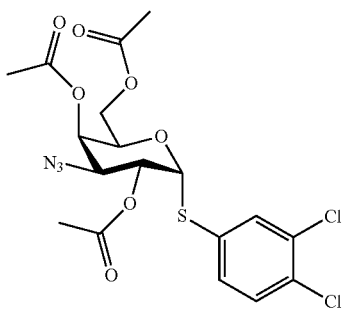

To a solution of 3,4-dichlorobenzenethiol (4.61 g, 0.03 mol) in N,N-dimethylformamide (0.05 L) was added NaH (0.53 g, 0.02 mol). The mixture was stirred at room temperature for 30 min. 2,4,6-Tri-O-acetyl-3-azido-1-chloro-3-deoxy-β-D-galactopyranoside (4.5 g, 0.01 mol) in DMF (10 mL) was added and the reaction mixture was stirred at 50° C. for 20 h. The mixture was diluted with DCM (100 mL), 0.5 M citric acid (50 mL) and water (50 mL). The organic phase was isolated and washed with water (100 mL×2) and concentrated. The residue was purified by column chromatography (SiO$_2$/PE:EA=3:1) to give the title compound 5.1 g (80.5%) as a white solid. m/z calcd for [C$_{18}$H$_{19}$Cl$_2$N$_3$O$_7$S]$^+$ [M+NH$_4$]$^-$: 509.0; found: 509.0.

3,4-Dichlorophenyl 2,4,6-tri-O-acetyl-3-deoxy-3-[4-(5-fluoro-2-pyridyl)-1H-1,2,3-triazol-1-yl]-1-thio-α-D-galactopyranoside

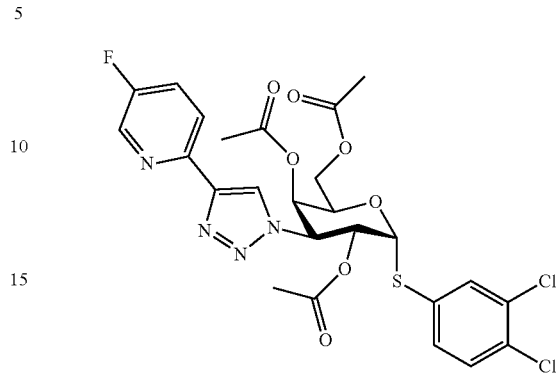

To a solution of 3,4-dichlorophenyl 2,4,6-tri-O-acetyl-3-azido-3-deoxy-1-thio-α-D-galactopyranoside (600 mg, 1.22 mmol) in N,N-dimethylformamide (10 mL) was added 5-fluoro-2-((trimethylsilyl)ethynyl)pyridine (2 eq), triethylamine (246.6 mg, 2.44 mmol), Copper(I)Iodide (69.63 mg, 0.37 mmol). The mixture was purged 3 times with N$_2$. The reaction mixture was stirred at 100° C. for 2 h. The reaction was quenched with water (20 ml). The reaction mixture was extracted with dichloromethane (50 mL×3). The combined organic phases were washed with brine (20 mL XI), dried over Na$_2$SO$_4$, filtered, and evaporated. The crude product was purified using combiflash (EA:PE=1:3, ISCO 40 g, 40 ml/min normal, phase silica, uv254) to give the title compound 550 mg (73%) as a yellow solid.

m/z calcd for [C$_{25}$H$_{23}$Cl$_2$FN$_4$O$_7$S]$^+$ [M+H]$^+$: 618.0; found: 618.0.

i7) 5-Bromopyridin-3-yl 2,4,6-tri-O-acetyl-3-deoxy-3-[4-(2-thiophenyl)-1H-1,2,3-triazol-1-yl]-1-thio-α-D-galactopyranoside

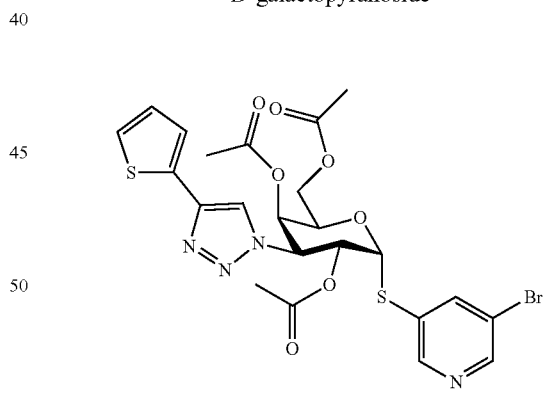

5-Bromopyridin-3-yl 2,4,6-tri-O-acetyl-3-azido-3-deoxy-1-thio-α-D-galactopyranoside (50 mg, 0.1 mmol) in CH$_3$CN (3 mL) were added TEA (0.1 ml), Copper(I)Iodide (6 mg, 0.03 mmol), 2-ethynylthiophene (22 mg, 0.2 mmol). The reaction was stirred at rt for 2 h under N$_2$ atmosphere. Water (10 mL) and DCM (10 mL) were added. The aqueous phase was extracted with DCM (5 mL×2) and the combined organic phases were washed with water (20 mL) and brine (20 mL), dried over anhydrous sodium sulphate. Removal of solvent gave a residue. The residue was purified by column chromatography (PE/EA=3/1) to obtain the desired product (30 mg, 49%).

m/z calcd for [C₂₃H₂₃BrN₄O₇S₂]⁺ [M+H]⁺: 611.0; found: 611.0.

i8) 3,5-Dichloro-4-fluoro-phenyl 2,4,6-tri-O-acetyl-3-deoxy-3-[4-(2-thiophenyl)-1H-1,2,3-triazol-1-yl]-1-thio-α-D-galactopyranoside

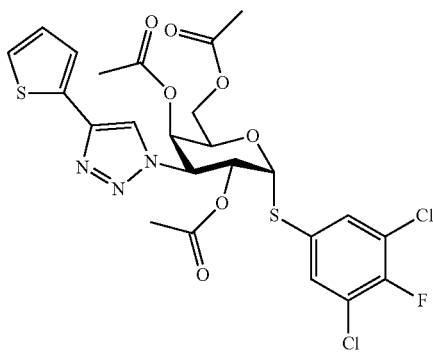

3,5-Dichloro-4-fluoro-phenyl 2,4,6-tri-O-acetyl-3-azido-3-deoxy-1-thio-α-D-galactopyranoside (50 mg, 0.10 mmol) in DMF (3 mL) were added TEA (0.10 mL), Copper(I) Iodide (6 mg, 0.03 mmol), CsF (24 mg, 0.15 mmol), 2-ethynylthiophene (16 mg, 0.15 mmol). The reaction stirred at room temperature for 20 h under N₂ atmosphere. Water (10 mL) and DCM (10 mL) were added. The phases were separated and the aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1) to obtain the desired product (30 mg, 49%).

ESI-MS m/z calcd for [C₂₃H₂₂Cl₂FN₃O₇S₂]⁺ [M+H]⁺: 618.0; found: 618.0.

i9) ((5-bromothiophen-2-yl)ethynyl)trimethylsilane

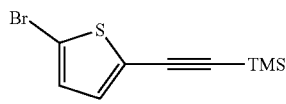

To a solution of 2,5-dibromothiophene (3.66 g, 0.015 mol), CuI (0.07 g, 0.37 mmol), and Pd(PPh₃)₂Cl₂ (0.26 g, 0.37 mmol) in 100 ml of diisopropylamine was added (trimethylsilyl)acetylene (1.47 g, 0.015 mol). The mixture was stirred at room temperature overnight under a nitrogen atmosphere. After removal of the solvent under reduce pressure, the residue was purified by column chromatography with hexane as the mobile-phase to give the title compound 1.63 g (yield 42%).

¹H NMR (400 MHz, CDCl₃) δ 6.78 (dd, J=4.0 Hz, 5.2 Hz, 1H), 0.01 (s, 9H).

((4-bromothiophen-2-yl)ethynyl)trimethylsilane

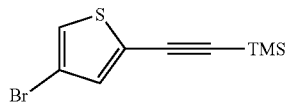 [SMILES: C[Si](C)(C)C#Cc1cc(Br)cs1]

To a stirred solution of 2-(5-bromo-2-thienyl)ethynyl-trimethyl-silane (100 mg, 0.39 mmol) in THF (0.2 mL) at −78° C. under a N₂ atmosphere was added a solution of LDA (41.3 mg, 0.39 mmol) via syringe over 5 min. The reaction mixture was stirred at −78° C. for 0.5 hr. The reaction mixture was quenched by water (0.5 ml) and partitioned between EtOAc (10 mL) and water (50 mL). The organic layer was washed with brine, dried over Na₂SO₄ and evaporated to dryness. The crude product was purified by flash chromatography on silica gel (n-hexane) to give title compound (70 mg, 70%).

¹H NMR (400 MHz, CDCl₃) δ 7.14 (d, J=1.2 Hz, 1H), 6.91 (d, J=1.2 Hz, 1H), 0.01 (s, 9H).

((5-thiophen-2-yl)ethynyl)trimethylsilane

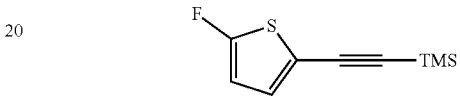

A solution of n-Butyllithium (109 mg, 1.7 mmol) in THF (0.8 mL) was added dropwise into a solution of 2-(4-bromo-2-thienyl) ethynyl-trimethyl-silane (200 mg, 0.77 mmol) in THF (5 mL) at −78° C. under a N₂ atmosphere, while keeping inner temperature between −70° C.−−78° C. The reaction mixture was stirred at −78° C. over 1 h. A solution of N-Fluorobenzenesulfonimide (608.2 mg, 1.93 mmol) in THF (5 mL) was added dropwise and the reaction mixture was stirred at −78° C. for 2 h. After quenching the reaction by water (10 ml), the reaction mixture was poured into separatory funnel and the phases were separated. The aqueous layer was extracted with ethyl acetate (10 mL) twice. The combined organic layers were washed with brine and dried over Na₂SO₄. The organic layer was filtered and concentrated under reduced pressure to provide crude material as an oil. The crude was used as is in the next step.

3,4-Dichlorophenyl 2,4,6-tri-O-acetyl-3-deoxy-3-[4-(5-fluoro-2-thiophenyl)-1H-1,2,3-triazol-1-yl]-1-thio-α-D-galactopyranoside

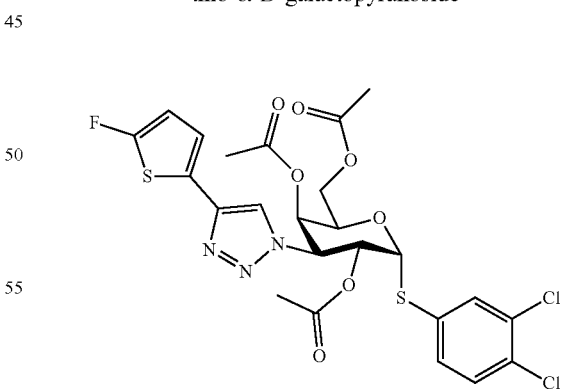

3,4-Dichlorophenyl 2,4,6-tri-O-acetyl-3-azido-3-deoxy-1-thio-α-D-galactopyranoside (0.23 g) and 2-(4,5-difluoro-2-thienyl)ethynyl-trimethyl-silane (0.1 g) were dissolved in CH₃CN (6 mL). Then iodocopper (0.03 g), and DIPEA (0.22 g) were added. The mixture was stirred at rt for 5 min. followed by addition of CsF (0.09 g) was added. The reaction mixture was stirred at rt over night followed by concentration and purification by prep-TLC (PE:EA=5:2) to give 8 mg (2.5%) of the title compound which was used immediately in the next step.

i10) 5-Bromo-6-trifluoromethyl-pyridin-3-yl 2,4,6-tri-O-acetyl-3-deoxy-3-[4-(4-thiazolyl)-1H-1,2,3-triazol-1-yl]-1-thio-α-D-galactopyranoside Trimethyl(2-thiazol-4-ylethynyl)silane

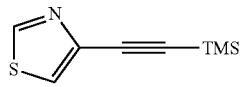 [SMILES: C[Si](C)(C)C#Cc1cscn1]

4-Bromothiazole (1 g, 6.1 mmol), CuI (58.1 mg, 0.3 mmol), Pd(PPh$_3$)$_2$Cl$_2$ (128.4 mg, 0.18 mmol), and ethynyl (trimethyl)silane (898.2 mg, 9.15 mmol) in TEA (4 mL) were degassed, placed under N$_2$, and stirred at 75° C. for 5 hr. The reaction mixture was cooled to RT and partitioned between DCM and water. The organic phase was dried over MgSO$_4$, concentrated, and column chromatography using 0-25% EtOAc/hexane afforded the title product 800 mg (72.4%) as a brown oil.

ESI-MS m/z calcd for [C$_8$H$_{12}$NSSi]$^+$ (M+H)$^+$: 182.0; found: 182.1.

5-Bromo-6-trifluoromethyl-pyridin-3-yl 2,4,6-tri-O-acetyl-3-deoxy-3-[4-(4-thiazolyl)-1H-1,2,3-triazol-1-yl]-1-thio-α-D-galactopyranoside

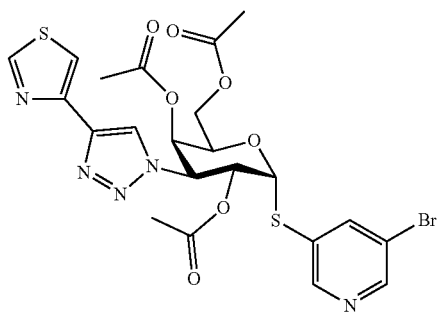

5-Bromopyridin-3-yl 2,4,6-tri-O-acetyl-3-azido-3-deoxy-1-thio-α-D-galactopyranoside (100 mg, 0.2 mmol), TEA (60.31 mg, 0.6 mmol) and trimethyl(2-thiazol-4-ylethynyl)silane (72.05 mg, 0.4 mmol) were dissolved in CH$_3$CN (5 mL). CuI (18.92 mg, 0.1 mmol) and CsF (45.27 mg, 0.3 mmol) were added. The mixture was stirred at rt for 4 hours. Then the mixture was concentrated and the residue was purified on silica gel column using a gradient of EA/PE from 0-40% to give the title compound 50 mg (41.1%).

ESI-MS nm/z calcd for [C$_{22}$H$_{23}$BrN$_5$O$_7$S$_2$]$^+$ (M+H)$^+$: 612.0; found: 612.0.

i11) 5-Bromo-6-trifluoromethyl-pyridin-3-yl 2,4,6-tri-O-acetyl-3-deoxy-3-[4-(4-thiazolyl)-1H-1,2,3-triazol-1-yl]-1-thio-α-D-galactopyranoside 3,5-dichloro-2-iodopyridine

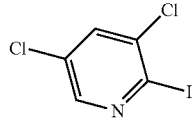

A mixture of 2-bromo-3,5-dichloropyridine (5.672 g, 25 mmol), sodium iodide (11241.7 mg, 75 mmol) and chlorotrimethylsilane (2716 mg, 25 mmol) in MeCN (50 mL) was heated under reflux for 45 min. The reaction mixture was then poured into a 2.0 M aqueous solution of sodium hydroxide (10 mL) and extracted with diethyl ether (20 mL×3). The combined organic layers were washed with brine and evaporated to afford crude product, which was purified by biotage (EtOAc/PE=1%~10%, ISCO 40 g, 25 mL/min, normal phase silica gel, uv 254) to afford the target compound (3800 mg, 55.5% yield) as a white solid.

$^1$H NMR (400 MHz, MeOD) δ 8.35 (t, J=4.5 Hz, 1H), 8.01 (d, J=2.3 Hz, 1H).

GC-MS m/z calcd for [C5H2Cl2IN]: 272.9; found: 273.0.

3,5-dichloro-2-(trifluoromethyl)pyridine

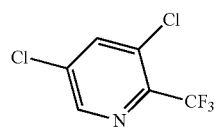

KF (87.18 mg, 1.5 mmol) and CuI (285.80 mg, 1.5 mmol) were thoroughly mixed before being heated under vacuum (1 mm Hg) with the flame of a Bunsen burner with gentle shaking until an homogeneous greenish color was obtained. NMP (25 mL), trimethyl(trifluoromethyl)silane (213.88 mg, 1.5 mmol). The mixture was stirred at 50° C. for 45 min. 3,5-dichloro-2-iodopyridine (2250 mg, 7.45 mmol) was added. The mixture was stirred at 50° C. overnight. The reaction was followed by GC-MS, which indicated formed product. Water (50 mL) was added to mixture and extracted with Ethyl acetate (5 mL×3). The combined organic layers were washed with brine and evaporated to afford crude product, which was purified by biotage (EtOAc/PE=1% 50%, ISCO 12 g, 10 mL/min, normal phase silica gel, uv 254) to afford the target compound (198 mg, 92% yield) as brown oil.

$^1$H NMR (400 MHz, MeOD) δ 8.66 (d, J=2.0 Hz, 1H), 8.34-8.24 (m, 1H).

GC-MS m/z calcd for [C$_6$H$_2$Cl$_2$F$_3$N]: 215.0; found: 215.0.

2.3 5-chloro-6-(trifluoromethyl)pyridine-3-thiol

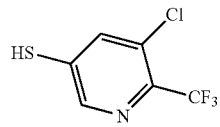 [SMILES: FC(F)(F)c1ncc(S)cc1Cl]

3,5-dichloro-2-(trifluoromethyl)pyridine (1080 mg, 5.0 mmol) and NaSH (336.4 mg, 6.0 mmol) were dissolved in DMF (15 mL). The reaction mixture was stirred at room temperature for 3 h followed by adjustment to pH 9 by addition of 10% aq NaOH. The reaction mixture was extracted with Et$_2$O (10 mL×3) and the aqueous layer was acidified with 2 M NaHSO$_4$ to pH~3. The mixture was extracted with ethyl acetate (15 mL×3). The combined organic layers were washed with brine and evaporated to afford crude product, which was purified by biotage (EtOAc/PE=1%~50%, ISCO 20 g, 15 mL/min, normal phase silica gel, uv 254) to afford 5-chloro-6-(trifluoromethyl)pyridine-3-thiol (650 mg, 61% yield) as brown oil, which was used for next without further purification.

$^1$H NMR (400 MHz, MeOD) δ 8.48 (d, J=1.4 Hz, 1H), 8.02 (d, J=17.1 Hz, 2H).

ESI-MS m/z calcd for [C$_6$H$_3$ClF$_3$NS]$^+$ (M−H)$^−$: 213.0; found: 211.9.

5-Bromo-6-trifluoromethyl-pyridin-3-yl 2,4,6-tri-O-acetyl-3-azido-3-deoxy-1-thio-α-D-galactopyranoside

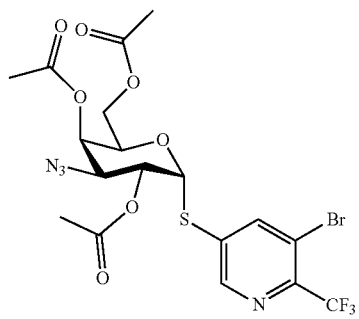

NaH (90 mg, 60% in mineral oil, 2.25 mmol) was added to a solution of 5-bromo-6-(trifluoromethyl)pyridine-3-thiol (578 mg, 2.24 mmol) in DMF (10 mL) at 0° C. The solution was stirred at rt for 30 min. Then 2,4,6-tri-O-acetyl-3-azido-1-chloro-3-deoxy-β-D-galactopyranoside (525 mg, 1.50 mmol) was added to mixture. The reaction was stirred at 50° C. for 2 h. The mixture was cooled to room temperature and water (50 mL) was added. Then it was extracted with EtOAc (10 mL×3). The combined organic layers were washed with brine, dried over Na$_2$SO$_4$ and concentrated in vacuo to afford crude product, which was purified by biotage (EA/PE=5%~40%, ISCO 12 g, 10 mL/min, normal phase silica gel, uv 254) to afford the title compound (120 mg, 14.0% yield) as a gray solid.

ESI-MS m/z calcd for [C$_{18}$H$_{18}$BrF$_3$N$_4$O$_7$S]$^+$ (M+H)$^+$: 570.0; found: 571.0.

5-Bromo-6-trifluoromethyl-pyridin-3-yl 2,4,6-tri-O-acetyl-3-deoxy-3-[4-(4-thiazolyl)-1H-1,2,3-triazol-1-yl]-1-thio-α-D-galactopyranoside

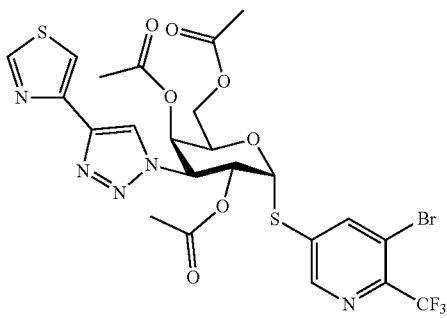

To a solution of 5-Bromo-6-trifluoromethyl-pyridin-3-yl 2,4,6-tri-O-acetyl-3-azido-3-deoxy-1-thio-α-D-galactopyranoside (50 mg, 0.09 mmol) in DMF (15 mL) was added trimethyl-[2-(3,4,5-trifluorophenyl)ethynyl]silane (32 mg, 0.14 mmol), iodocopper (6 mg, 0.03 mmol), CsF (21 mg, 0.14 mmol) and triethylamine (27 mg, 0.27 mmol). The reaction vessel was purged thrice with nitrogen. Then the mixture was stirred at room temperature for 5 h. The mixture was filtered and washed with EtOAc (30 mL), The filtrated was concentrated in vacuo to afford crude product (50 mg), which was used for next step directly without further purification.

ESI-MS m/z calcd for [C$_{23}$H$_{21}$BrF$_3$N$_5$O$_7$S$_2$]$^+$ (M+H)$^+$: 679.0; found: 680.0.

i12) 3,4-Dichlorophenyl 2,4,6-tri-O-acetyl-3-deoxy-3-[4-(4-thiazolyl)-1H-1,2,3-triazol-1-yl]-1-thio-α-D-galactopyranoside

4-((trimethylsilyl)ethynyl)thiazole

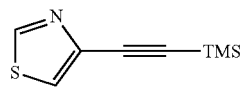 [SMILES: C[Si](C)(C)C#Cc1cscn1]

To a solution of 4-bromothiazole (1 g, 6.13 mmol) in CH$_3$CN (50 mL) was added CuI (348 mg, 1.83 mmol), DIPEA (5 mL), Pd(PPh$_3$)$_2$Cl$_2$ (428 mg, 0.61 mmol). The mixture was heated under N$_2$ at 50° C. for 20 h. Removal of solvent gave a residue. The residue was purified by column chromatography (PE/EA=10/1) to obtain the title compound (400 mg, 36%).

3,4-Dichlorophenyl 2,4,6-tri-O-acetyl-3-azido-3-deoxy-1-thio-α-D-galactopyranoside

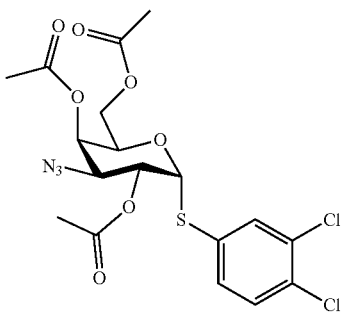

NaH (54 mg, 1.34 mmol) was added to a solution of 3,4-dichlorobenzenethiol (200 mg, 1.12 mmol) in DMF (10 mL) at 0° C. The solution was stirred at rt for 30 min. Then 2,4,6-tri-O-acetyl-3-azido-1-chloro-3-deoxy-β-D-galactopyranoside (313 mg, 0.90 mmol) was added to mixture. The reaction was stirred at 50° C. for 2 h. The mixture was cooled to room temperature and water (20 mL) was added. The reaction mixture was extracted with EtOAc (15 mL×3). The combined organic layers were washed with brine, dried over Na$_2$SO$_4$ and concentrated in vacuo to afford crude product, which was purified by biotage (EA/PE=5%~40%, ISCO 40 g, 30 mL/min, normal phase silica gel, UV 254) to afford the target compound (100 mg, 22.6% yield) as a white solid.

ESI-MS m/z calcd for $[C_{18}H_{19}Cl_2N_3O_7S]^+$ $[M+H]^+$: 492.0; found: 492.0.

3,4-Dichlorophenyl 2,4,6-tri-O-acetyl-3-deoxy-3-[4-(4-thiazolyl)-1H-1,2,3-triazol-1-yl]-1-thio-α-D-galactopyranoside

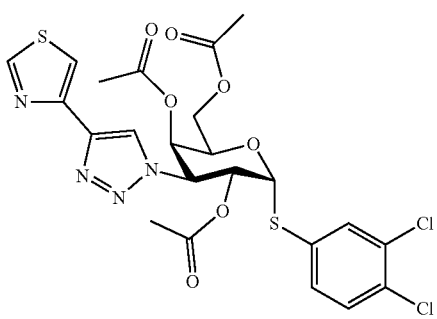

To a solution of 3,4-dichlorophenyl 2,4,6-tri-O-acetyl-3-azido-3-deoxy-1-thio-α-D-galactopyranoside (100 mg, 0.20 mmol) in DMF (3 mL) were added TEA (0.20 mL), Copper (I)Iodide (11 mg, 0.06 mmol), CsF (46 mg, 0.30 mmol), 4-((trimethylsilyl)ethynyl)thiazole (55 mg, 0.30 mmol). The reaction was stirred at room temperature for 20 h under N$_2$. Water (10 mL) and DCM (10 mL) were added. The aqueous phase was extracted with DCM (5 mL×2) and the combined organic phases were washed with water (20 mL) and brine (20 mL), dried over anhydrous sodium sulphate. Removal of solvent gave a residue. The residue was purified by column chromatography (PE/EA=2/1) to obtain the desired product (70 mg, 58.3%).

ESI-MS m/z calcd for $[C_{23}H_{22}Cl_2N_4O_7S_2]^+$ $[M+H]^+$: 601.0; found: 601.0.

i13) 2-Chloro-benzonitril-4-yl 2,4,6-tri-O-acetyl-3-deoxy-3-[4-(4-thiazolyl)-1H-1,2,3-triazol-1-yl]-1-thio-α-D-galactopyranoside 2-chloro-4-mercaptobenzonitrile

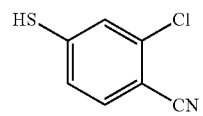

To a solution of 2-chloro-4-fluorobenzonitrile (4 g, 25.81 mmol) in DMF (10 mL) was added Na$_2$S 9H$_2$O (10.8 g, 38.70 mmol). The reaction was held at room temperature with stirring on for 20 h. The mixture was added NaHSO$_4$ aq to adjust pH 4-5 and MTBE (20 ml) was added. The organic phase was washed with water (30 mL) and brine (30 mL), dried over anhydrous sodium sulphate. Removal of solvent gave the crude product (3.7 g, crude).

m/z calcd for $[C_7H_3ClNS]^-$ $[M-H]^-$: 168.0; found: 168.0.

2-Chloro-benzonitril-4-yl 2,4,6-tri-O-acetyl-3-azido-3-deoxy-1-thio-α-D-galactopyranoside

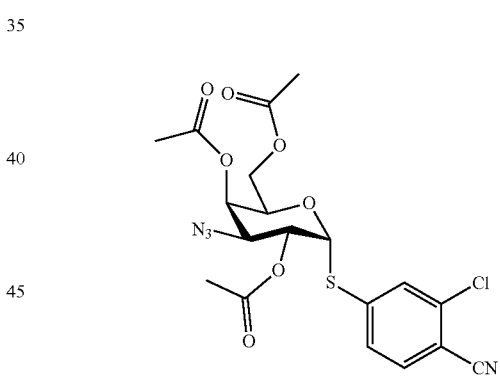

To a solution of 2-chloro-4-mercaptobenzonitrile (3.7 g, 21.9 mmol) in DMF (50 mL) was added NaH (882.7 mg, 22.1 mmol) at 0° C. After 10 min, 2,4,6-tri-O-acetyl-3-azido-1-chloro-3-deoxy-β-D-galactopyranoside (3.5 g, 10.0 mmol) was added. The reaction mixture was stirred at room temperature for 4 h. Water (50 mL) and DCM (50 mL) were added. The aqueous phase was extracted with DCM (50 mL×2) and the combined organic phases were washed with water (100 mL) and brine (100 mL), dried over anhydrous sodium sulphate. Removal of the solvent gave a residue. The residue was purified by column chromatography (PE/EA=3/1) to obtain the desired product (2 g, 41%).

m/z calcd for $[C_{19}H_{18}ClN_4O_7S]^-$ $[M+H]^-$: 483.0; found: 483.0.

2-Chloro-benzonitril-4-yl 2,4,6-tri-O-acetyl-3-deoxy-3-[4-(4-thiazolyl)-1H-1,2,3-triazol-1-yl]-1-thio-α-D-galactopyranoside

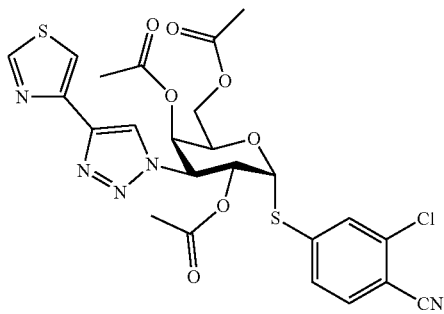

To a solution of 2-chloro-benzonitril-4-yl 2,4,6-tri-O-acetyl-3-azido-3-deoxy-1-thio-α-D-galactopyranoside (50 mg, 0.10 mmol) in DMF (3 mL) were added TEA (0.10 mL), Copper(I)Iodide (6 mg, 0.03 mmol), CsF (24 mg, 0.15 mmol), 4-((trimethylsilyl)ethynyl)thiazole (28 mg, 0.15 mmol). The reaction was held at room temperature with stirring on for 20 h under $N_2$. Water (10 mL) and DCM (10 mL) were added. The aqueous phase was extracted with DCM (5 mL×2), the combined organic phase was washed with water (20 mL) and brine (20 mL), dried over anhydrous sodium sulphate. Removal of solvent gave a residue. The residue was purified by column chromatography (PE/EA=2/1) to obtain the desired product (50 mg, 64%).

ESI-MS m/z calcd for $[C_{24}H_{22}ClN_5O_7S_2]^-$ $[M+H]^-$: 592.0; found: 592.0.

i14) 3,5-Dichloro-4-fluoro-phenyl 2,4,6-tri-O-acetyl-3-deoxy-3-[4-(4-thiazolyl)-1H-1,2,3-triazol-1-yl]-1-thio-α-D-galactopyranoside

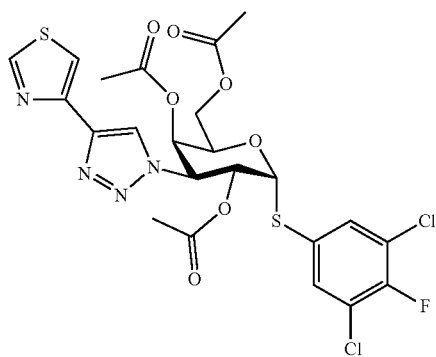

3,5-Dichloro-4-fluoro-phenyl 2,4,6-tri-O-acetyl-3-azido-3-deoxy-1-thio-α-D-galactopyranoside (50 mg, 0.10 mmol) in DMF (3 mL) were added TEA (0.10 mL), Copper(I) Iodide (6 mg, 0.03 mmol), CsF (24 mg, 0.15 mmol), 2-((trimethylsilyl)ethynyl)thiazole (28 mg, 0.15 mmol). The reaction was stirred at room temperature for 20 h under $N_2$. Water (10 mL) and DCM (10 mL) were added. The aqueous phase was extracted with DCM (5 mL×2), the combined organic phase was washed with water (20 mL) and brine (20 mL), dried over anhydrous sodium sulphate. Removal of solvent gave a residue. The residue was purified by column chromatography (PE/EA=2/1) to obtain the desired product (30 mg, 48.5%).

ESI-MS m/z calcd for $[C_{23}H_{21}Cl_2FN_4O_7S_2]^+$ $[M+H]^+$: 619.0; found: 619.0.

i15) 5-Bromopyridin-3-yl 2,4,6-tri-O-acetyl-3-deoxy-3-[4-(1-hydroxyethyl)-1H-1,2,3-triazol-1-yl]-1-thio-α-D-galactopyranoside

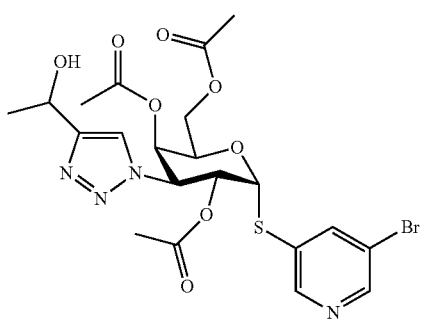

To a solution of 5-Bromopyridin-3-yl 2,4,6-tri-O-acetyl-3-azido-3-deoxy-1-thio-α-D-galactopyranoside (250 mg, 0.50 mmol) in DMF (5 mL) were added DIPEA (0.4 mL), Copper(I)Iodide (29 mg, 0.15 mmol), 3-butyn-2-ol (52 mg, 0.75 mmol). The reaction was stirred at room temperature for 20 h under a $N_2$ atmosphere. Water (10 mL) and DCM (10 mL) were added and the phases were separated. The aqueous phase was extracted with DCM (5 mL×2) and the combined organic phases were washed with water (20 mL) and brine (20 mL), dried over anhydrous sodium sulphate. Removal of solvent gave a residue. The residue was purified by column chromatography (PE/EA=1/1) to obtain the desired product (170 mg, 59.4%).

m/z calcd for $[C_{21}H_{25}BrN_4O_8S]^+$ $[M+H]^+$: 573.0; found: 573.0.

5-Bromopyridin-3-yl 2,4,6-tri-O-acetyl-3-deoxy-3-[4-(acetyl)-1H-1,2,3-triazol-1-yl]-1-thio-α-D-galactopyranoside

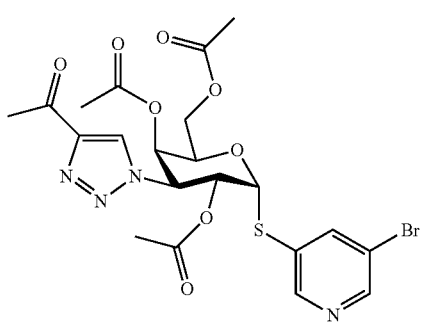

To a solution of 5-bromopyridin-3-yl 2,4,6-tri-O-acetyl-3-deoxy-3-[4-(1-hydroxyethyl)-1H-1,2,3-triazol-1-yl]-1-thio-α-D-galactopyranoside (170 mg, 0.30 mmol) in DCM (4 mL) was added Dess-Martin periodinane (252 mg, 0.60 mmol). The reaction was stirred at room temperature for 20 h under N$_2$. Removal of solvent gave a residue and which was purified by column chromatography (PE/EA=1/1) to obtain the title compound (165 mg, 97%).

m/z calcd for [C$_{21}$H$_{23}$BrN$_4$O$_8$S]$^+$ [M+H]$^+$: 571.0; found: 571.0.

5-Bromopyridin-3-yl 2,4,6-tri-O-acetyl-3-deoxy-3-[4-(2-bromoacetyl)-1H-1,2,3-triazol-1-yl]-1-thio-D-galactopyranoside

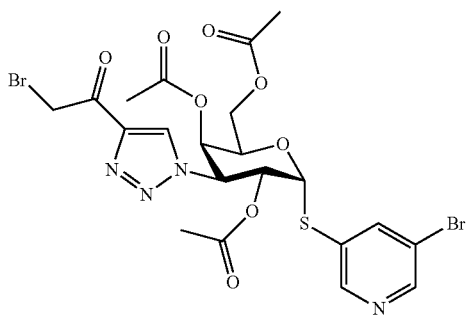

To a solution of 5-bromopyridin-3-yl 2,4,6-tri-O-acetyl-3-deoxy-3-[4-(acetyl)-1H-1,2,3-triazol-1-yl]-1-thio-α-D-galactopyranoside (165 mg, 0.29 mmol) in DCM (5 mL) was added TEA (0.2 mL) in ice bath. After 10 min, TBSOTf (0.2 mL) was added in the mixture. The reaction was held at 0° C. with stirring on for 2 h under N$_2$. Water (10 mL) and DCM (10 mL) were added and the phases were separated. The organic phase was washed with sat. NaHCO$_3$ (20 mL) and brine (20 mL), dried over anhydrous sodium sulphate. Removal of solvent gave a residue. The residue was dissolved in THF (5 ml) and water (0.05 ml) was added in ice bath. After 10 min, NBS (52 mg, 0.29 mmol) was added. The reaction was held at 0° C. with stirring on for 10 min under N$_2$. Water (10 mL) and TBME (10 mL) were added. The organic phase was washed with sat. NaHCO$_3$ (20 mL) and brine (20 mL), dried over anhydrous sodium sulphate. Removal of solvent gave a residue. The residue was purified by column chromatography (PE/EA=2/1) to obtain the title compound (150 mg, 80%).

m/z calcd for [C$_{21}$H$_{22}$Br$_2$N$_4$O$_8$S]$^+$ [M+H]$^+$: 649.0; found: 649.0.

$^1$H NMR (400 MHz, CDCl$_3$) δ 8.63 (d, J=2.0 Hz, 1H), 8.60 (d, J=1.9 Hz, 1H), 8.20 (s, 1H), 8.00 (t, J=2.0 Hz, 1H), 6.14 (d, J=5.5 Hz, 1H), 6.00 (dd, J=11.7, 5.5 Hz, 1H), 5.60 (d, J=2.1 Hz, 1H), 5.27 (dd, J=11.7, 3.0 Hz, 1H), 4.88-4.82 (m, 1H), 4.67 (s, 2H), 4.11 (ddd, J=19.3, 11.7, 6.3 Hz, 2H), 2.08 (s, 3H), 2.04 (s, 3H), 2.00 (s, 3H).

5-Bromopyridin-3-yl 2,4,6-tri-O-acetyl-3-deoxy-3-[4-(2-methyl-4-thiazolyl)-1H-1,2,3-triazol-1-yl]-1-thio-α-D-galactopyranoside

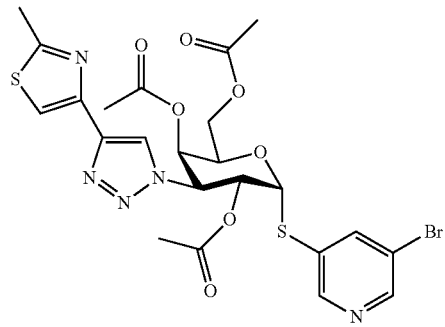

To a solution of 5-Bromopyridin-3-yl 2,4,6-tri-O-acetyl-3-deoxy-3-[4-(2-bromoacetyl)-1H-1,2,3-triazol-1-yl]-1-thio-α-D-galactopyranoside (50 mg, 0.08 mmol) in ethyl acetate (5 mL) was added thioacetamide (18 mg, 0.23 mmol), Silver trifluoromethanesulfonate (40 mg, 0.15 mmol). The reaction was stirred at 50° C. for 20 h under a N$_2$ atmosphere. Removal of solvent gave a residue. The residue was purified by column chromatography (PE/EA=1/1) to obtain the title compound (30 mg, 60%).

m/z calcd for [C$_{23}$H$_{24}$BrN$_5$O$_7$S$_2$]$^+$ [M+H]$^+$: 626.0; found: 626.0.

i16) 2,6-Dichloro-bensonitril-4-yl 2,4,6-tri-O-acetyl-3-deoxy-3-[4-(2-thiazolyl)-1H-1,2,3-triazol-1-yl]-1-thio-α-D-galactopyranoside N-(4-bromo-3,5-dichlorophenyl)acetamide

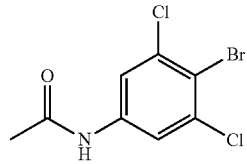

To a solution of 4-bromo-3,5-dichloroaniline (1.00 g, 4.18 mmol) in Ac$_2$O (5 mL) was added pyridine (0.1 mL). The reaction was stirred at room temperature for 2 h. The mixture was poured into 50 mL ice water and extracted with EA (20 mL×3). The organic layer was washed with brine (50 mL), dried with Na$_2$SO$_4$, and concentrated in vacuo to afford product (1 g, 85%).

ESI-MS m/z calcd for [C$_8$H$_6$BrCl$_2$NO]$^+$ [M+H]$^+$: 2820; found: 282.0.

N-(3,5-dichloro-4-cyanophenyl)acetamide

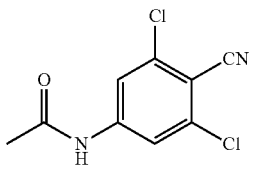

To a solution of N-(4-bromo-3,5-dichlorophenyl)acetamide (700 mg, 2.49 mmol) in DMF (10 mL) was added CuCN (439 mg, 3.73 mmol). The reaction was stirred at 140° C. under N₂ for 20 h. The mixture was cooled to room temperature. Water (50 mL) and EA (30 mL) was added in the mixture. The mixture was filtered and washed with EA (20 mL×2). The organic layer was washed with brine (50 mL), dried with Na₂SO₄, and concentrated in vacuo to afford crude product. The crude product was purified by flash chromatography (EA/PE=5%~40%, ISCO 40 g, 30 mL/min, normal phase silica gel, UV254) to afford the target compound (500 mg, 88%) ESI-MS m/z calcd for $[C_9H_6Cl_2N_2O]^+$ $[M+H]^+$: 229.0; found: 229.0.

4-amino-2,6-dichlorobenzonitrile

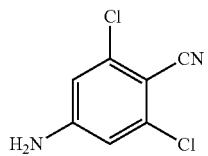

To a solution of N-(3,5-dichloro-4-cyanophenyl)acetamide (500 mg, 2.19 mmol) in EtOH (10 mL) was added con. HCl (0.2 mL). The reaction was stirred at 80° C. under N₂ for 2 h and then concentrated in vacuo. The residue was dissolved into EA (10 mL) and washed with sat. NaHCO₃, dried with Na₂SO₄, concentrated in vacuo to afford product (300 mg, 74%).

ESI-MS m/z calcd for $[C_7H_4Cl_2N_2]^+$ $[M+H]^+$: 187.0; found: 187.0.

S-3,5-dichloro-4-cyanophenyl O-ethyl carbonodithioate

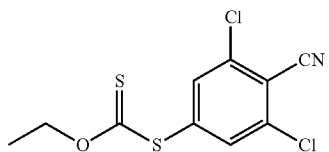 [SMILES: CCOC(=S)Sc1cc(Cl)c(C#N)c(Cl)c1]

4-amino-2,6-dichlorobenzonitrile (300 mg, 1.61 mmol) was dissolved in 10 ml HCl and was cooled to 0° C. An aqueous solution of NaNO₂ (111 mg, 1.61 mmol) was added slowly the reaction mixture was stirred at 0° C. until the mixture was clear. The reaction mixture was heated to 50° C. followed by slow addition of potassium ethyl xantogenate (388 mg, 2.42 mmol) dissolved in 15 ml water. The reaction mixture was stirred at 70° C. for 2 h. The reaction mixture was extracted with EtOAc (100 mL). The organic phase was washed by brine, dried over Na₂SO₄, filtered and concentrated to give 150 mg crude product which was used immediately in the next step.

2,6-dichloro-1-mercaptobenzonitrile

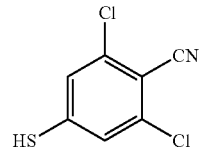 [SMILES: N#Cc1c(Cl)cc(S)cc1Cl]

S-3,5-dichloro-4-cyanophenyl O-ethyl carbonodithioate (150 mg, 0.52 mmol) was dissolved in 5 mL ethanol. The reaction mixture was stirred at 85° C. followed by slow addition of KOH (98 mg, 2 mmol). The reaction was stirred at 85° C. for 2 h. The pH was adjusted to pH 4-5 by addition of HCl. The reaction mixture was extracted with EA (5 mL×2) and the phases were separated, solvents were removed from the combined organics to give product. (70 mg, 60%)

ESI-MS m/z calcd for $[C_7H_3Cl_2NS]^-$ $[M+H]^-$: 202.0; found: 202.0.

2,6-Dichloro-bensonitril-4-yl 2,4,6-tri-O-acetyl-3-azido-3-deoxy-1-thio-α-D-galactopyranoside

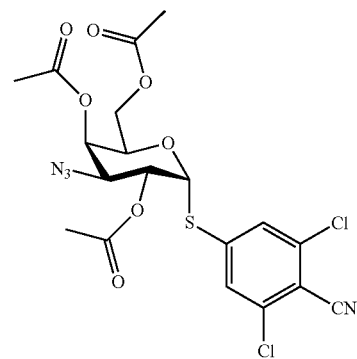

NaH (17 mg, 0.42 mmol) was added to a solution of 2,6-dichloro-4-mercaptobenzonitrile (70 mg, 0.35 mmol) in DMF (5 mL) at 0° C. The solution was stirred at room temperature for 30 min. Then 2,4,6-tri-O-acetyl-3-azido-1-chloro-3-deoxy-β-D-galactopyranoside (98 mg, 0.28 mmol) was added to mixture. The reaction was stirred at 50° C. for 2 h. The mixture was cooled to room temperature and water (10 mL) was added followed by extraction with EtOAc (10 mL×3). The combined organic layers were washed with brine, dried over Na₂SO₄ and concentrated in vacuo to afford crude product, which was purified by flash chromatography on a biotage (EA/PE=5%~40%, ISCO 40 g, 30 mL/min, normal phase silica gel, UV254) to afford the target compound (10 mg, 18.1% yield) as a white solid.

ESI-MS m/z calcd for $[C_{19}H_{18}Cl_2N_4O_7S]^-$ $[M+18]^+$: 534.0; found: 534.0.

2,6-Dichloro-bensonitril-4-yl 2,4,6-tri-O-acetyl-3-deoxy-3-[4-(2-thiazolyl)-1H-1,2,3-triazol-1-yl]-1-thio-α-D-galactopyranoside

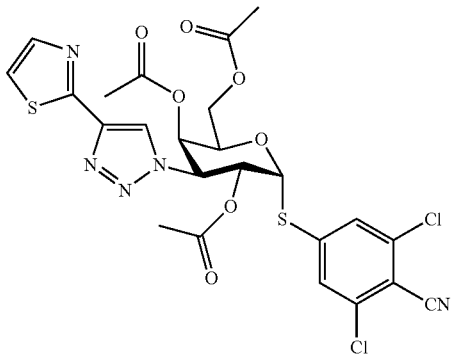

2,6-Dichloro-bensonitril-4-yl 2,4,6-tri-O-acetyl-3-azido-3-deoxy-1-thio-α-D-galactopyranoside (10 mg, 0.02 mmol) in DMF (3 mL) were added TEA (0.05 mL), Copper(I) Iodide (2 mg, 0.006 mmol), CsF (5 mg, 0.03 mmol), 2-((trimethylsilyl)ethynyl)thiazole (6 mg, 0.03 mmol). The reaction was held at room temperature with stirring on for 20 h under $N_2$. Water (5 mL) and DCM (5 mL) were added. The aqueous phase was extracted with DCM (5 mL×2), the combined organic phase was washed with water (20 mL) and brine (20 mL), dried over anhydrous sodium sulphate. Removal of solvent gave a residue. The residue was purified by column chromatography (PE/EA=2/1) to obtain the desired product (4 mg, 32%).

ESI-MS m/z calcd for $[C_{24}H_{21}Cl_2N_5O_7S_2]^-$ $[M+H]^-$: 626.0; found: 626.0.

i17) 3,4,5-Trichlorophenyl 2,4,6-tri-O-acetyl-3-deoxy-3-[4-(2-thiazolyl)-1H-1,2,3-triazol-1-yl]-1-thio-α-D-galactopyranoside

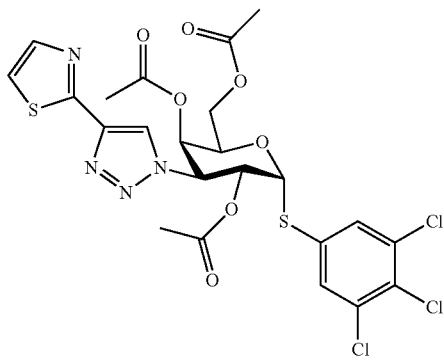

3,4,5-Trichlorophenyl 2,4,6-tri-O-acetyl-3-azido-3-deoxy-1-thio-α-D-galactopyranoside (50 mg, 0.10 mmol) in DMF (3 mL) were added TEA (0.10 mL), Copper(I)Iodide (6 mg, 0.03 mmol), CsF (24 mg, 0.15 mmol), 2-((trimethylsilyl)ethynyl)thiazole (28 mg, 0.15 mmol). The reaction was stirred at room temperature for 20 h under $N_2$. Water (10 mL) and DCM (10 mL) were added. The aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1) to obtain the desired product (30 mg, 49%).

ESI-MS m/z calcd for $[C_{23}H_{21}Cl_2FN_4O_7S_2]^+$ $[M+H]^+$: 636.0; found: 636.0.

i18) 3,4-Dichlorophenyl 2,4,6-tri-O-acetyl-3-deoxy-3-[4-(2-thiazolyl)-1H-1,2,3-triazol-1-yl]-1-thio-α-D-galactopyranoside

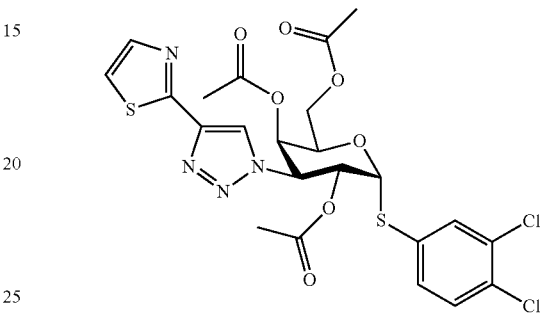

3,4-Dichlorophenyl 2,4,6-tri-O-acetyl-3-azido-3-deoxy-1-thio-α-D-galactopyranoside (50 mg, 0.10 mmol) in DMF (3 mL) were added TEA (0.10 mL), Copper(I)Iodide (6 mg, 0.03 mmol), CsF (24 mg, 0.15 mmol), 2-((trimethylsilyl)ethynyl)thiazole (28 mg, 0.15 mmol). The reaction was stirred at room temperature for 20 h under a $N_2$ atmosphere. Water (10 mL) and DCM (10 mL) were added. The aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1) to obtain the desired product (30 mg, 49%).

ESI-MS m/z calcd for $[C_{23}H_{21}Cl_2FN_4O_7S_2]^+$ $[M+H]^+$: 635.0; found: 635.0.

i19) O-ethyl S-3,4,5-trichlorophenyl Carbonodithioate

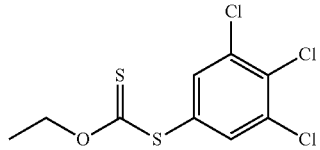

3,4,5-trichloroaniline (2.0 g, 10 mmol) was dissolved in 10 ml HCl and was cooled to 0° C. An aqueous solution of $NaNO_2$ (111 mg, 1.61 mmol) was added slowly the reaction mixture was stirred at 0° C. until the mixture was clear. The reaction mixture was heated to 50° C. followed by slow addition of potassium ethyl xantogenate (2.7 g, 15 mmol) dissolved in 15 ml water. The reaction mixture was stirred at 70° C. for 2 h. The reaction mixture was extracted with EtOAc (100 mL). The organic phase was washed by brine, dried over $Na_2SO_4$, filtered and concentrated to give 2 g crude product which was used immediately in the next step.

3,4,5-trichlorobenzenethiol

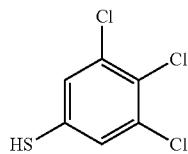

O-ethyl S-3,4,5-trichlorophenyl carbonodithioate (2 g, 7 mmol) was dissolved in 20 mL ethanol, the solution was stirred at 85° C., KOH (0.98 g, 20 mmol) was added in it slowly, then stirred at 85° C. for 2 h, added HCl pH to 4~5, extracted with EA (20 mL×2), give title compound (850 mg, 58%)

ESI-MS m/z calcd for $[C_6H_3Cl_2FS]^-$ $[M+H]^-$: 211.0; found: 211.0.

3-Azido-1,3-dideoxy-2,4,6-tri-O-acetyl-1-(3,4,5-trichlorobenzenethiol)-α-D-galactopyranoside

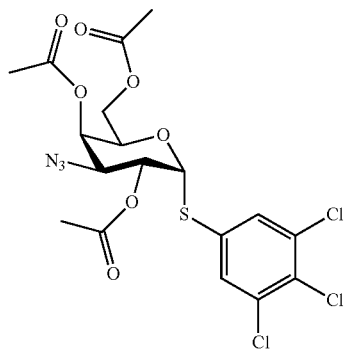

NaH (90 mg, 2.24 mmol) was added to a solution of 3,4,5-trichlorobenzenethiol (400 mg, 2.04 mmol) in DMF (10 mL) at 0° C. The solution was stirred at room temperature for 30 min followed by addition of 2,4,6-tri-O-acetyl-3-azido-1-chloro-3-deoxy-β-D-galactopyranoside (570 mg, 1.63 mmol). The reaction was stirred at 50° C. for 2 h. The mixture was cooled to room temperature and water (20 mL) was added. The reaction mixture was extracted with EtOAc (15 mL×3). The combined organic layers were washed with brine, dried over $Na_2SO_4$ and concentrated in vacuo to afford crude product, which was purified by flash chromatography (EA/PE=5%~40%, ISCO 40 g, 30 mL/min, normal phase silica gel, UV254) to afford the target compound (150 mg, 18% yield) as a white solid.

ESI-MS m/z calcd for $[C_{18}H_{18}C_{12}FN_3O_7S]^+$ $[M+H]^+$: 526.0; found: 526.0.

3,4,5-Trichlorophenyl 2,4,6-tri-O-acetyl-3-deoxy-3-[4-(1,3,4-thiadiazol-2-yl)-1H-1,2,3-triazol-1-yl]-1-thio-α-D-galactopyranoside

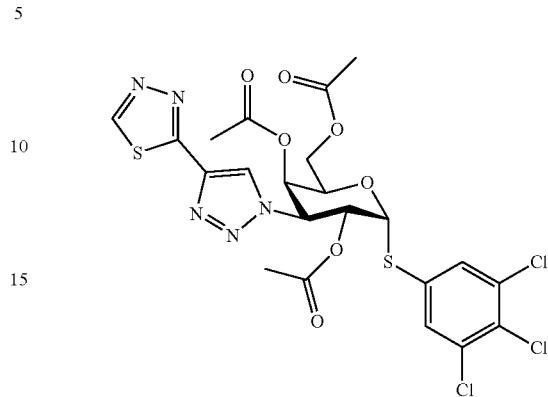

3-Azido-1,3-dideoxy-2,4,6-tri-O-acetyl-1-(3,4,5-trichlorobenzenethiol)-α-D-galactopyranoside (50 mg, 0.10 mmol) in DMF (3 mL) were added TEA (0.10 mL), Copper(I) Iodide (6 mg, 0.03 mmol), CsF (24 mg, 0.15 mmol), 2-((trimethylsilyl)ethynyl)thiazole (28 mg, 0.15 mmol). The reaction was stirred at room temperature for 20 h under a $N_2$ atmosphere. Water (10 mL) and DCM (10 mL) were added. The aqueous phase was extracted with DCM (5 mL×2), the combined organic phases were washed with water (20 mL) and brine (20 mL), dried over anhydrous sodium sulphate. Removal of solvent gave a residue. The residue was purified by column chromatography (PE/EA=2/1) to obtain the desired product (30 mg, 49%).

ESI-MS m/z calcd for $[C_{23}H_{21}Cl_2FN_4O_7S_2]^+$ $[M+H]^+$: 636.0; found: 636.0.

i20) 5-Bromopyridin-3-yl 2,4,6-tri-O-acetyl-3-deoxy-3-[4-(2-thiazolyl)-1H-1,2,3-triazol-1-yl]-1-thio-α-D-galactopyranoside trimethyl(2-thiazol-2-ylethynyl)silane

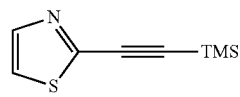

2-Bromothiazole (5 g, 30.5 mmol), ethynyl(trimethyl)silane (8.982 g, 91.5 mmol), iodocopper (1740 mg, 9.15 mmol), bis(Triphenylphosphine)palladium (II) chloride (1113 mg, 1.52 mmol) and DIPEA (11.82 g, 91.5 mmol) were dissolved in THF (200 mL). The mixture was stirred at 60° C. overnight under N2. The mixture was extracted with EtOAc (30 mL×2), the combined organic layers were washed with brine (20 mL), dried over $Na_2SO_4$, filtered and concentrated in vacuo to afford crude product, which was purified by silica gel column chromatography using a gradient of EtOAc/PE (13%) to give the title compound 800 mg (14.5% yield) as brown oil. $^1$H NMR (400 MHz, CDCl3) δ 7.81 (d, J=3.3 Hz, 1H), 7.34 (d, J=3.3 Hz, 1H), 0.28 (s, 9H). ESI-MS m/z calcd for $[C_8H_{12}NSSi]^+$ $[M+H]^+$: 182.0; found: 182.0.

5-Bromopyridin-3-yl 2,4,6-tri-O-acetyl-3-deoxy-3-[4-(2-thiazolyl)-1H-1,2,3-triazol-1-yl]-1-thio-α-D-galactopyranoside

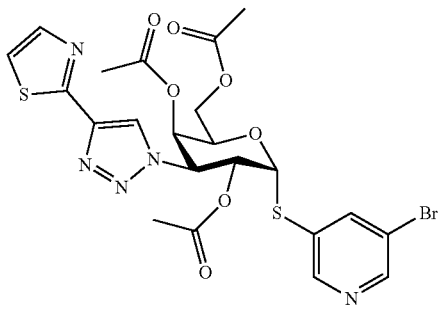

5-Bromopyridin-3-yl 2,4,6-tri-O-acetyl-3-azido-3-deoxy-1-thio-α-D-galactopyranoside (144 mg, 0.286 mmol), trimethyl(2-thiazol-2-ylethynyl)silane (104 mg, 0.572 mmol), Copper(I)Iodide (16.3 mg, 0.0858 mmol), TEA (0.12 mL) 0.858 mmol) and CsF (43.5 mg, 0.286 mmol) were dissolved in acetonitrile (8.00 mL). The mixture was stirred at rt overnight. The mixture was extracted with EtOAc (10 mL×2), the combined organic layers were washed with brine (20 mL), dried over $Na_2SO_4$, filtered and concentrated in vacuo to afford crude product, which was purified by silica gel column chromatography using a gradient of EtOAc/PE (27%) to give the title compound as a white solid, 140 mg (79.9%). $^1H$ NMR (400 MHz, $CDCl_3$) δ 8.62 (dd, J=5.8, 1.9 Hz, 2H), 8.13 (s, 1H), 8.02 (t, J=1.9 Hz, 1H), 7.86 (d, J=3.2 Hz, 1H), 7.40 (d, J=3.2 Hz, 1H), 6.17 (d, J=5.6 Hz, 1H), 6.01 (dd, J=11.7, 5.6 Hz, 1H), 5.64 (d, J=2.3 Hz, 1H), 5.28 (dd, J=11.8, 3.0 Hz, 1H), 4.93-4.81 (m, 1H), 4.26-3.99 (m, 2H), 3.83-3.66 (m, 1H), 2.10 (s, 3H), 2.05 (s, 3H), 1.99 (s, 3H). ESI-MS nm/z calcd for $[C_{22}H_{23}BrN_5O_7S_2]^+$ $[M+H]^+$: 612.0; found: 612.0.

i21) 5-Chloropyridin-3-yl 2,4,6-tri-O-acetyl-3-deoxy-3-[4-(2-thiazolyl)-1H-1,2,3-triazol-1-yl]-1-thio-α-D-galactopyranoside

O-[(5-chloro-3-pyridyl)] N,N-dimethylcarbamothioate

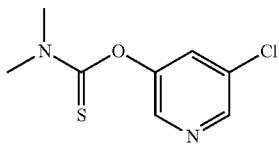

To a solution of 5-chloropyridin-3-ol (3.0 g, 23.2 mmol) in N,N-dimethylformamide (40 mL) was added NaH (1.5 g, 40% in mineral, 25.5 mmol) at 0° C., then the mixture was stirred at 0° C. for 30 min. Dimethylthiocarbamoyl chloride (3.15 g, 25.5 mmol) was added to the mixture, then it was stirred at room temperature for 20 h. The reaction was followed by TLC. The reaction was quenched with water (150 mL). The mixture was extracted with $CH_2Cl_2$ (80 mL×3) and the aqueous phase was discarded. The combined organic layers were washed with brine (80 mL×2), dried over $Na_2SO_4$, filtered and concentrated in vacuo to afford crude product, which was purified by Biotage (EA:PE=1:5 to 1:2, ISCO® 40 g, 40 mL/min, normal phase silica, uv254). 4 g (79.7%) of the title compound as brown oil was obtained.

ESI-MS m/z calcd for $[C_8H_9ClN_2OS]^+$ $[M+H]^-$: 217.0; found: 217.0.

S-[(5-chloro-3-pyridyl)] N,N-dimethylcarbamothioate

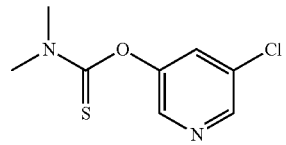

O-[(5-chloro-3-pyridyl)] N,N-dimethylcarbamothioate (4 g, 18.5 mmol) was taken up to in phenoxybenzene (20 mL) was added to 2 mL of refluxing phenoxybenzene. After 2 h, TLC analysis indicated the total consumption of the starting material. The reaction mixture was cooled and run through 200 g $SiO_2$ to remove the phenoxybenzene, subsequent elution with PE:EA=1:2 to give the target compound of 3.9 g (98%) of S-[(5-chloro-3-pyridyl)] N,N-dimethylcarbamothioate as a yellow solid.

ESI-MS m/z calcd for $[C_8H_9ClN_2OS]^+$ $[M+H]^-$: 217.0; found: 217.0.

5-chloropyridine-3-thiol

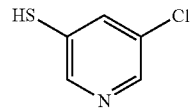

To a solution of S-[(5-chloro-3-pyridyl)] N,N-dimethylcarbamothioate (800 mg, 3.69 mmol) in methanol (5 mL) were added 2 N NaOH (5 mL). The reaction was stirred at 70° C. for 2 h. The mixture was cooled to room temperature and $NaHSO_4$ aq was added to adjust pH 6-7. Then $CH_2Cl_2$/MeOH (10/1) (10 mL) was added. The aqueous phase was extracted with $CH_2Cl_2$/MeOH (10/1) (30 mL×2), the combined organic phase was washed with brine (20 mL), dried over anhydrous sodium sulphate, filtered and concentrated in vacuo to afford 350 mg (65%) of 5-chloropyridine-3-thiol as a yellow solid, which was used for next step without further purification.

ESI-MS m/z calcd for $[C_5H_4ClNS]^-$ $[M-H]^-$: 144.0; found: 144.0.

5-Chloropyridin-3-yl 2,4,6-tri-O-acetyl-3-azido-3-deoxy-1-thio-α-D-galactopyranoside

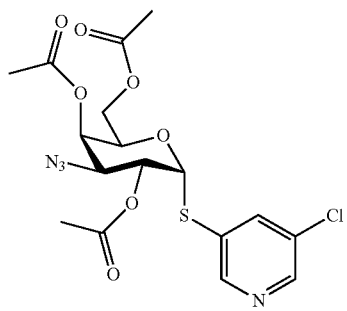

To a solution of 5-chloropyridine-3-thiol (350 mg, 2.40 mmol) in DMF (10 mL) were added Cs$_2$CO$_3$ (783 mg, 2.40 mmol), the mixture was stirred at room temperature for 30 min. 2,4,6-tri-O-Acetyl-3-azido-1-chloro-3-deoxy-β-D-galactopyranoside (420 mg, 1.20 mmol) was added to the solution. The reaction mixture was stirred at room temperature for 20 h. Water (40 mL) and CH$_2$Cl$_2$ (40 mL) were added. The aqueous phase was extracted with CH$_2$Cl$_2$ (40 mL×2), the combined organic phase were washed with brine (150 mL), dried over anhydrous sodium sulphate and concentrated in vacuo to afford crude product, which was purified by column chromatography (PE/EA=2/1) to give 400 mg (73%) of the title compound as a white solid.

$^1$H NMR (400 MHz, MeOD) δ 7.70 (d, J=2.0 Hz, 1H), 7.52 (d, J=8.4 Hz, 1H), 7.44 (dd, J=8.4, 2.0 Hz, 1H), 6.02 (d, J=5.5 Hz, 1H), 5.53 (d, J=3.1 Hz, 1H), 5.24 (dd, J=11.1, 5.5 Hz, 1H), 4.70 (dd, J=7.5, 4.7 Hz, 1H), 4.23 (dd, J=11.1, 3.3 Hz, 1H), 4.07 (ddd, J=19.5, 11.6, 6.2 Hz, 3H), 3.62 (q, J=7.0 Hz, 1H), 2.17 (s, 3H), 2.16 (s, 3H), 1.96 (s, 3H). ESI-MS m/z calcd for [C$_{17}$H$_{19}$ClN$_4$O$_7$S]$^+$ [M+H]$^+$: 459.0; found: 459.0.

5-Chloropyridin-3-yl 2,4,6-tri-O-acetyl-3-deoxy-3-[4-(2-thiazolyl)-1H-1,2,3-triazol-1-yl]-1-thio-α-D-galactopyranoside 5-Chloropyridin-3-yl 2,4,6-tri-O-acetyl-3-azido-3-deoxy-1-thio-α-D-galactopyranoside (100 mg, 0.218 mmol), TEA (0.152 mL) 1.09 mmol), Copper(I)Iodide (12.5 mg, 0.0654 mmol), CsF (49.7 mg, 0.327 mmol) and trimethyl(2-thiazol-2-ylethynyl)silane (59.3 mg, 0.327 mmol) were dissolved in CH$_3$CN (10 mL). The reaction was stirred at room temperature for 20 h under N$_2$. Water (10 mL) and CH$_2$Cl$_2$ (10 mL) were added. The aqueous phase was extracted with CH$_2$Cl$_2$ (5 mL×2), the combined organic phases were washed with water (20 mL) and brine (20 mL), dried over anhydrous sodium sulphate, filtered and concentrated in vacuo to afford crude product, which was purified by column chromatography (PE/EA=2/1). 80.0 mg (65%) of the title compound as a white sold was obtained.

ESI-MS m/z calcd for [C$_{25}$H$_{22}$ClF$_3$N$_4$O$_7$S]$^+$ [M+H]$^+$: 615.0; found: 615.0.

i22) 5-Bromo-2-cyano-pyridine-3-yl 2,4,6-tri-O-acetyl-3-deoxy-3-[4-(2-thiazolyl)-1H-1,2,3-triazol-1-yl]-1-thio-α-D-galactopyranoside and

123) 5-Chloro-6-cyano-pyridine-3-yl 2,4,6-tri-O-acetyl-3-deoxy-3-[4-(2-thiazolyl)-1H-1,2,3-triazol-1-yl]-1-thio-α-D-galactopyranoside

Acetyl 2,4,6-tri-O-acetyl-3-azido-3-deoxy-1-thio-α-D-galactopyranoside

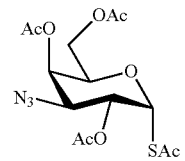

To a solution of 2,4,6-tri-O-acetyl-3-azido-1-chloro-3-deoxy-β-D-galactopyranoside (1.00 g, 2.86 mmol) in DMF (20 mL) was added potassium thioacetate (653 mg, 5.72 mmol) at room temperature for 20 h. Water (50 mL) and CH$_2$Cl$_2$ (50 mL) were added.

The aqueous phase was extracted with CH$_2$Cl$_2$ (50 mL×2), the combined organic phases were washed with water (100 mL) and brine (100 mL), dried over anhydrous sodium sulphate, filtered and concentrated in vacuo to afford crude product, which was purified by silica gel column chromatography (PE/EA=3/1). 400 mg (36%) of the title compound was obtained as a syrup.

ESI-MS m/z calcd for [C$_{14}$H$_{19}$N$_3$O$_8$S]$^+$ [M+18]$^-$: 407.0; found: 407.0.

5-Bromo-2-cyano-pyridine-3-yl 2,4,6-tri-O-acetyl-3-azido-3-deoxy-1-thio-α-D-galactopyranoside

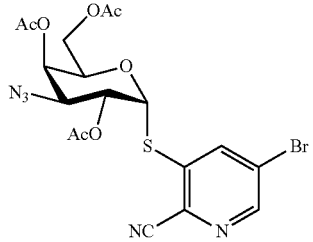

and

5-Chloro-6-cyano-pyridine-3-yl 2,4,6-tri-O-acetyl-3-azido-3-deoxy-1-thio-α-D-galactopyranoside

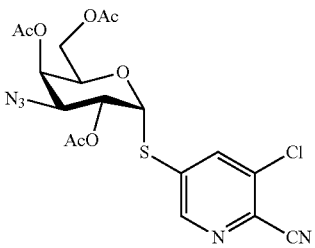

Acetyl 2,4,6-tri-O-acetyl-3-azido-3-deoxy-1-thio-α-D-galactopyranoside (400 mg, 1.03 mmol), 5-bromo-3-chloro-pyridine-2-carbonitrile (447 mg, 0.205 mmol) and N-ethylethanamine (0.213 mL, 2.05 mmol) were dissolved in DMF (16 mL). The reaction was stirred at room temperature for 20 h. Water (50 mL) and CH$_2$Cl$_2$ (50 mL) were added. The aqueous phase was extracted with CH$_2$Cl$_2$ (50 mL×2), the combined organic phase were washed with water (100 mL) and brine (100 mL), dried over anhydrous sodium, filtered and concentrated in vacuo to afford crude product, which was purified by column chromatography (PE/EA=3/1) to obtain the title mixture of products (200 mg, 38%).

5-Bromo-2-cyano-pyridine-3-yl 2,4,6-tri-O-acetyl-3-azido-3-deoxy-1-thio-α-D-galactopyranoside ESI-MS nm/z calcd for [C$_{18}$H$_{18}$ClN$_5$O$_7$S]$^-$ [M+H]$^+$: 484.0; found: 484.0.

5-Chloro-6-cyano-pyridine-3-yl 2,4,6-tri-O-acetyl-3-azido-3-deoxy-1-thio-α-D-galactopyranoside ESI-MS m/z calcd for [C$_{18}$H$_{18}$BrN$_5$O$_7$S]$^-$ [M+H]$^+$: 528.0; found: 528.0.

i22) 5-Bromo-2-cyano-pyridine-3-yl 2,4,6-tri-O-acetyl-3-deoxy-3-[4-(2-thiazolyl)-1H-1,2,3-triazol-1-yl]-1-thio-α-D-galactopyranoside

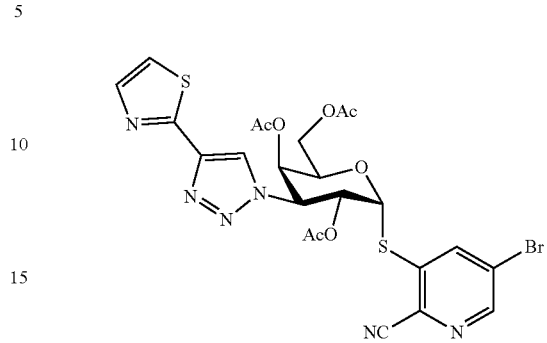

and i23) 5-Chloro-6-cyano-pyridine-3-yl 2,4,6-tri-O-acetyl-3-deoxy-3-[4-(2-thiazolyl)-1H-1,2,3-triazol-1-yl]-1-thio-α-D-galactopyranoside

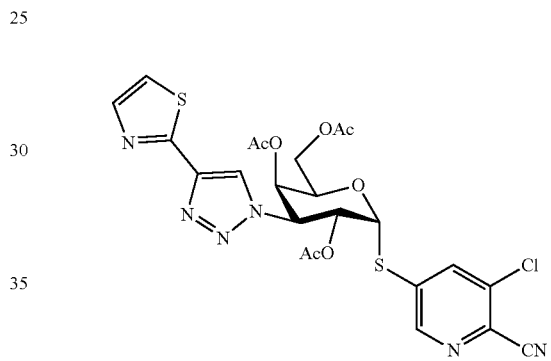

Mixture of 5-Bromo-2-cyano-pyridine-3-yl 2,4,6-tri-O-acetyl-3-azido-3-deoxy-1-thio-α-D-galactopyranoside and 5-Chloro-6-cyano-pyridine-3-yl 2,4,6-tri-O-acetyl-3-azido-3-deoxy-1-thio-α-D-galactopyranoside (200 mg) TEA (0.0528 mL) 0.379 mmol), Copper(I)Iodide (72.1 mg, 0.379 mmol), CsF (57.5 mg, 0.379 mmol) and trimethyl(2-thiazol-2-ylethynyl)silane (103 mg, 0.568 mmol) were dissolved in CH$_3$CN (5 mL). The mixture was stirred at room temperature for 20 h under N2. Water (10 mL) and CH$_2$Cl$_2$ (10 mL) were added. The aqueous phase was extracted with CH$_2$Cl$_2$ (5 mL×2), the combined organic phase were washed with water (20 mL) and brine (20 mL), dried over anhydrous sodium, filtered and concentrated in vacuo to afford crude product, which was purified by column chromatography (PE/EA=2/1) to give:

i22) 5-Bromo-2-cyano-pyridine-3-yl 2,4,6-tri-O-acetyl-3-deoxy-3-[4-(2-thiazolyl)-1H-1,2,3-triazol-1-yl]-1-thio-α-D-galactopyranoside Yield 60.0 mg (24.9%)

$^1$H NMR (400 MHz, CDCl$_3$) δ 8.63 (d, J=2.0 Hz, 1H), 8.15 (d, J=2.0 Hz, 1H), 8.08 (s, 1H), 7.80 (d, J=3.2 Hz, 1H), 7.33 (d, J=3.2 Hz, 1H), 6.23 (d, J=5.5 Hz, 1H), 6.02 (dd, J=11.7, 5.6 Hz, 1H), 5.60 (d, J=2.2 Hz, 1H), 5.19 (dd, J=11.7, 3.0 Hz, 1H), 4.79-4.75 (m, 1H), 4.15-3.98 (m, 3H), 2.03 (s, 3H), 1.96 (d, J=1.2 Hz, 6H).

ESI-MS m/z calcd for $[C_{24}H_{21}BrN_6O_7S_2]^+$ $[M+H]^+$: 637.0; found: 637.0.
and i23) 5-Chloro-6-cyano-pyridine-3-yl 2,4,6-tri-O-acetyl-3-deoxy-3-[4-(2-thiazolyl)-1H-1,2,3-triazol-1-yl]-1-thio-α-D-galactopyranoside 120 mg (53.5%)
$^1$H NMR (400 MHz, CDCl$_3$) δ 8.63 (d, J=1.9 Hz, 1H), 8.14 (s, 1H), 8.01 (d, J=2.0 Hz, 1H), 7.86 (d, J=3.2 Hz, 1H), 7.40 (d, J=3.2 Hz, 1H), 6.36 (d, J=5.5 Hz, 1H), 6.07 (dd, J=11.7, 5.6 Hz, 1H), 5.65 (d, J=2.3 Hz, 1H), 5.26 (dd, J=11.7, 3.0 Hz, 1H), 4.76 (dd, J=7.3, 4.9 Hz, 1H), 4.11 (ddd, J=22.1, 13.0, 6.2 Hz, 2H), 2.11 (s, 3H), 1.99 (d, J=7.3 Hz, 6H). ESI-MS m/z calcd for $[C_{23}H_{21}ClN_6O_7S_2]^+$ $[M+H]^+$: 593.0; found: 593.0.

i24) 2,4,6-tri-O-acetyl-3-deoxy-3-[4-(2-thiazolyl)-1H-1,2,3-triazol-1-yl]-1-thio-α-D-galactopyranoside 3,5-dichlorophenyl 2,4,6-tri-O-acetyl-3-azido-3-deoxy-1-thio-α-D-galactopyranoside

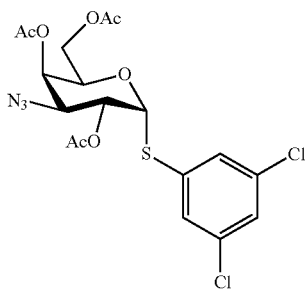

2,4,6-tri-O-acetyl-3-azido-1-chloro-3-deoxy-β-D-galactopyranoside (300 mg, 0.858 mmol), 3,5-dichlorobenzenethiol (307 mg, 1.72 mmol) and Cs$_2$CO$_3$ (559 mg, 1.72 mmol) were dissolved in N,N-dimethylformamide (10.0 mL). The mixture was stirred at room temperature overnight. EtOAc (100 mL) was added. The mixture was washed with brine, dried over Na$_2$SO$_4$, filtered and concentrated in vacuo to afford crude product, which was purified by chromatography on silica gel column using a gradient of EtOAc/PE (40%) to afford 280 mg (66%) of the title compound as a white solid.

ESI-MS m/z calcd for $[C_{18}H_{23}Cl_2N_4O_7S]^-$ $[M+NH_4]^+$: 509.0; found: 509.0.

3,5-dichlorophenyl 2,4,6-tri-O-acetyl-3-deoxy-3-[4-(2-thiazolyl)-1H-1,2,3-triazol-1-yl]-1-thio-α-D-galactopyranoside

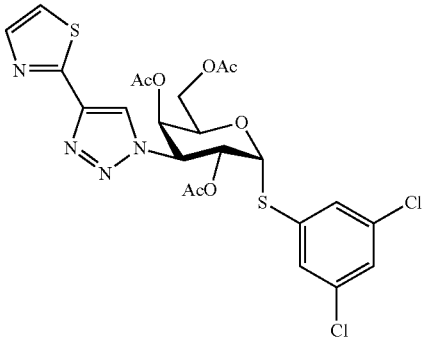

3,5-dichlorophenyl 2,4,6-tri-O-acetyl-3-azido-3-deoxy-1-thio-α-D-galactopyranoside (250 mg, 0.508 mmol) and trimethyl(2-thiazol-2-ylethynyl)silane (184 mg, 1.02 mmol) were dissolved in acetonitrile (12.00 mL). Copper(I)Iodide (29.0 mg, 0.152 mmol), TEA (0.212 mL, 1.52 mmol) and CsF (77.1 mg, 0.508 mmol) were added. The mixture was stirred at room temperature over night. EtOAc (100 mL) was added. The solution was washed by water (100 mL), brine (150 mL), dried over Na$_2$SO$_4$, filtered and concentrated in vacuo to afford crude product, which was purified by chromatography on silica gel column using a gradient of EtOAc/PE (40%) to afford 150 mg (49%) of the title compound as a white solid.

ESI-MS m/z calcd for $[C_{23}H_{23}ClN_4O_7S_2]^+$ $[M+H]^+$: 601.0; found: 601.0.

i25) 3-Bromo-4-chlorophenyl 2,4,6-tri-O-acetyl-3-deoxy-3-[4-(2-thiazolyl)-1H-1,2,3-triazol-1-yl]-1-thio-α-D-galactopyranoside O-[(3-bromo-4-chlorophenyl)] N,N-dimethylcarbamothioate

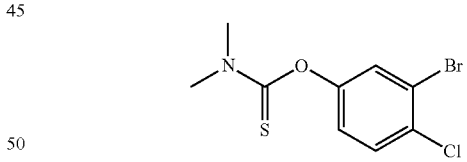

To a solution of 3-bromo-4-chlorophenol (2 g, 9.64 mmol) in N,N-dimethylformamide (30 mL) was added NaH (244 mg, 10.6 mmol) at 0° C., then the mixture was held at same temperature with stirring on for 30 min. dimethylthiocarbamoyl chloride (1.311 g, 10.6 mmol) was added to the mixture, then it was stirred at room temperature for 20 h. The reaction was quenched with water (50 mL). The mixture was extracted with CH$_2$Cl$_2$ (50 mL×3) and the aqueous phase was discarded. The combined organic layers were washed with brine (40 mL×3), dried over Na$_2$SO$_4$, filtered and concentrated in vacuo to afford crude product, which was purified by flash chromatography using a Biotage (EA: PE=0~20%, ISCO® 40 g, 40 mL/min, normal phase silica, uv254). 2.5 g (88.0%) of the title compound as brown was obtained.

$^1$H NMR (400 MHz, CDCl$_3$) δ 7.45 (d, J=8.7 Hz, 1H), 7.36 (d, J=2.7 Hz, 1H), 7.00 (dd, J=8.7, 2.7 Hz, 1H), 3.44 (s, 3H), 3.33 (s, 3H).

S-[(3-bromo-4-chlorophenyl)] N,N-dimethylcarbamothioate

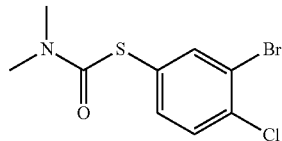

O-[(3-bromo-4-chlorophenyl)] N,N-dimethylcarbamothioate (2.5 g, 8.49 mmol) was dissolved in phenoxybenzene (20 mL), then the mixture was refluxed for 2 hours. TLC analysis indicated the total consumption of the starting material. The reaction mixture was cooled and purified by silica gel column chromatography using a gradient of EA/PE from 0~35%. 2.4 g (96.0%) of the title compound as a yellow solid was obtained.

ESI-MS m/z calcd for [C$_9$H$_9$BrClNOS]$^+$ [M+H]$^+$: 292.9; found: 294.0.

3-bromo-4-chlorobenzenethiol

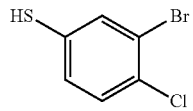

NaOH (679 mg, 17.0 mmol) was added in to a solution of S-[(3-bromo-4-chlorophenyl)] N,N-dimethylcarbamothioate (1.00 g, 3.39 mmol) in EtOH/H$_2$O (25.0 mL, 3/1). The reaction was refluxed for 16 hours. The mixture was concentrated to about 10 mL, taken up to 30 mL EtOAc added with 2 mol/L hydrochloric acid to adjust the pH to about 6. The mixture was extracted with EtOAc (10 mL×3) and the aqueous phase was discarded. The combined organic layers were washed with brine (30 mL), dried over Na$_2$SO$_4$, filtered and concentrated in vacuo to afford 500 mg (65.9%) crude product, which was used for next step directly without further purification.

ESI-MS m/z calcd for [C$_6$H$_4$BrClS]$^-$ [M+H]$^+$: 221.9; found: 223.0.

3-Bromo-4-chlorophenyl 2,4,6-tri-O-acetyl-3-azido-3-deoxy-1-thio-α-D-galactopyranoside

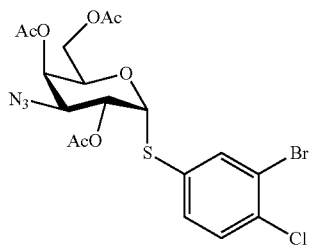

Cs$_2$CO$_3$ (279 mg, 0.858 mmol) was added to a solution of 3-bromo-4-chlorobenzenethiol (192 mg, 0.858 mmol) in DMF (10 mL) at 0° C. The solution was stirred at room temperature for 30 min. Then 2,4,6-tri-O-acetyl-3-azido-1-chloro-3-deoxy-β-D-galactopyranoside (200 mg, 0.572 mmol) was added to the mixture. The reaction was stirred at 50° C. for 2 h. The mixture was cooled to room temperature and water (50 mL) was added. Then it was extracted with EtOAc (15 mL×3). The combined organic layers were washed with brine, dried over Na$_2$SO$_4$ and concentrated in vacuo to afford crude product, which was purified by flash chromatography using a Biotage® (EA/PE=5%~40%, ISCO® 40 g, 30 mL/min, normal phase silica gel, uv 254). 200 mg (65.2%) of the title compound as a grey solid was obtained.

ESI-MS m/z calcd for [C$_{18}$H$_{19}$BrClN$_3$O$_7$S]$^+$ [M+H]$^+$: 535.0; found: 536.0.

$^1$H NMR (400 MHz, CDCl$_3$) δ 7.65 (d, J=2.0 Hz, 1H), 7.31 (d, J=8.4 Hz, 1H), 7.26 (dd, J=8.4, 2.1 Hz, 1H), 5.90 (d, J=5.5 Hz, 1H), 5.42 (s, 1H), 5.40 (d, J=2.7 Hz, 1H), 5.20 (dd, J=10.9, 5.5 Hz, 1H), 4.59-4.41 (m, 1H), 4.05 (dd, J=11.6, 5.0 Hz, 1H), 3.94 (dd, J=11.6, 7.7 Hz, 1H), 3.87 (dd, J=11.0, 3.3 Hz, 1H), 3.42 (d, J=4.8 Hz, 1H), 2.12 (s, 3H), 2.10 (s, 3H), 1.93 (s, 3H).

3-Bromo-4-chlorophenyl 2,4,6-tri-O-acetyl-3-deoxy-3-[4-(2-thiazolyl)-1H-1,2,3-triazol-1-yl]-1-thio-α-D-galactopyranoside

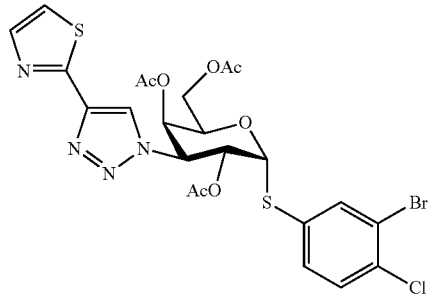

3-Bromo-4-chlorophenyl 2,4,6-tri-O-acetyl-3-azido-3-deoxy-1-thio-α-D-galactopyranoside (200 mg, 0.373 mmol), TEA (0.260 mL), Copper(I)Iodide (21.3 mg, 0.112 mmol), CsF (84.9 mg, 0.559 mmol) and trimethyl(2-thiazol-2-ylethynyl)silane (101 mg, 0.559 mmol) were dissolvent in CH$_3$CN (10 mL). The reaction was stirred at room temperature overnight under N$_2$. The mixture was extracted with CH$_2$Cl$_2$ (5 mL×2), the combined organic phase was washed with water (20 mL) and brine (20 mL), dried over Na$_2$SO$_4$, filtered and concentrated in vacuo to afford crude product, which was purified by silica gel column chromatography (PE/EA=2/1) to give the title compound 150 mg (62.3%).

ESI-MS m/z calcd for [C$_{23}$H$_{22}$BrClN$_4$O$_7$S$_2$]$^+$ [M+H]$^+$: 644.0; found: 645.0.

$^1$H NMR (400 MHz, CDCl$_3$) δ 8.12 (s, 1H), 7.86 (d, J=3.2 Hz, 1H), 7.77 (d, J=2.0 Hz, 1H), 7.46-7.33 (m, 3H), 6.16 (d, J=5.5 Hz, 1H), 5.99 (dd, J=11.7, 5.6 Hz, 1H), 5.62 (d, J=2.5 Hz, 1H), 5.34-5.17 (m, 1H), 4.88-4.74 (m, 1H), 4.26-3.96 (m, 4H), 2.09 (s, 3H), 2.01 (s, 3H), 1.98 (s, 3H).

i26) 5-Bromo-6-trifluoromethyl-pyridine-3-yl 2,4,6-tri-O-acetyl-3-deoxy-3-[4-(2-thiazolyl)-1H-1,2,3-triazol-1-yl]-1-thio-α-D-galactopyranoside 3-Bromo-5-fluoro-2-iodo-pyridine

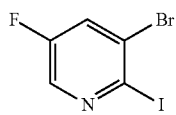

A mixture of 2,3-dibromo-5-fluoro-pyridine (5.00 g, 19.6 mmol), NaI (8821 mg, 58.9 mmol) and chloro(trimethyl)silane (2131 mg, 19.6 mmol) in MeCN (50 mL) was stirred at room temperature overnight. The reaction mixture was then poured into a 2.0 M aqueous solution of sodium hydroxide (10 mL) and extracted with diethyl ether (20 mL×3). The combined organic layers were washed with brine and concentrated in vacuo to afford crude product, which was purified by flash chromatography using a Biotage® (EA/PE=1%~10%, ISCO® 40 g, 25 mL/min, normal phase silica gel, uv 254) to afford 3.8 g (64.2%) of the title compound as a gray solid.
ESI-MS m/z calcd for [$C_5H_2BrFIN$] [M]301; found: 301.

3-bromo-5-fluoro-2-(trifluoromethyl)pyridine

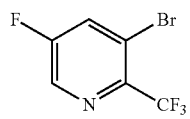

KF (212 mg, 3.64 mmol) and iodocopper (631 mg, 3.31 mmol) were thoroughly mixed before being heated under vacuum (1 mm Hg) with the flame of a Bunsen burner with gentle shaking until an homogeneous greenish color was obtained. NMP (10 mL) and (Trifluoromethyl)trimethylsilane (471 mg, 3.31 mmol) were added into mixture. The mixture was stirred at 50° C. for 45 min. 3-bromo-5-fluoro-2-iodo-pyridine (1000 mg, 3.31 mmol) was added. The mixture was stirred at 50° C. overnight. The reaction was monitored by GC-MS indicating product formed. Water (20 mL) was added to mixture and extracted with EtOAc (15 mL×3). The combined organic layers were washed with brine and concentrated in vacuo to afford crude product, which was purified by flash chromatography Biotage (EA/PE=1%~50%, ISCO® 40 g, 25 mL/min, normal phase silica gel, uv 254). 575 mg (71.1%) of the title compound as a white solid was obtained. ESI-MS m/z calcd for [$C_6H_2BrF_4N$] [M]: 242.9; found: 243.0.

5-bromo-6-(trifluoromethyl)pyridine-3-thiol

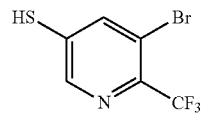

3-bromo-5-fluoro-2-(trifluoromethyl)pyridine 5 mg, 2.36 mmol) and disodium sulfide (623 mg, 2.59 mmol) were dissolved in DMF (10 mL). The reaction mixture was stirred at room temperature for 3 h. 10% aq NaOH was added into mixture to pH~9. The mixture was extracted with Et$_2$O (30 mL×3), the aqueous layer was acidified with 2 M NaHSO$_4$ to pH~3. The mixture was extracted with EA (3×15 mL). The combined organic layers were washed with brine and concentrated in vacuo to afford crude product, which was purified by flash chromatography using a Biotage® (EA/PE=1%~50%, ISCO® 20 g, 15 mL/min, normal phase silica gel, uv 254) to give 300 mg (49.3%) of the title compound as brown oil was obtained, which was used for next step without further purification.

5-Bromo-6-trifluoromethyl-pyridine-3-yl 2,4,6-tri-O-acetyl-3-azido-3-deoxy-1-thio-α-D-galactopyranoside

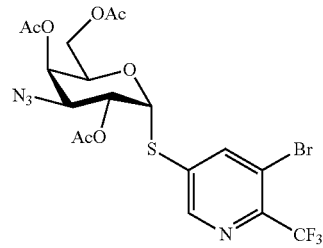

Cs$_2$CO$_3$ (186 mg, 0.572 mmol) was added to a solution of 5-bromo-6-(trifluoromethyl)pyridine-3-thiol (295 mg, 1.14 mmol) in DMF (10 mL) at 0° C. The solution was stirred at rt for 30 min. Then 2,4,6-tri-O-acetyl-3-azido-1-chloro-3-deoxy-β-D-galactopyranoside (200 mg, 0.572 mmol) was added to mixture. The reaction was stirred at 50° C. for 2 h. The mixture was cooled to room temperature and water (30 mL) was added followed by extraction with EtOAc (15 mL×3). The combined organic layers were washed with brine, dried over Na$_2$SO$_4$ and concentrated in vacuo to afford crude product, which was purified by flash chromatography using a Biotage® (EA/PE=5%~40%, ISCO® 40 g, 30 mL/min, normal phase silica gel, uv 254) to give the title compound 91.0 mg (27.9%) as a white solid.
ESI-MS m/z calcd for [$C_{18}H_{18}BrF_3N_4O_7S$]$^+$ [M+H]$^+$: 570.0; found: 571.1.

5-Bromo-6-trifluoromethyl-pyridine-3-yl 2,4,6-tri-O-acetyl-3-deoxy-3-[4-(2-thiazolyl)-1H-1,2,3-triazol-1-yl]-1-thio-α-D-galactopyranoside

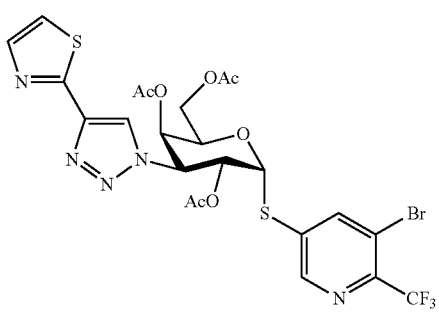

To a solution of 5-Bromo-6-trifluoromethyl-pyridine-3-yl 2,4,6-tri-O-acetyl-3-azido-3-deoxy-1-thio-α-D-galactopyranoside (91.0 mg, 0.159 mmol) in CH₃CN (5 mL) were added TEA (0.111 mL, 0.796 mmol), Copper(I)Iodide (9.10 mg, 0.0478 mmol), CsF (36.3 mg, 0.239 mmol), trimethyl (2-thiazol-2-ylethynyl)silane (43.3 mg, 0.239 mmol). The reaction was stirred at room temperature with for 20 h under a nitrogen atmosphere. Water (10 mL) and CH₂Cl₂ (10 mL) were added. The aqueous phase was extracted with CH₂Cl₂ (5 mL×2), the combined organic phase was washed with water (20 mL) and brine (20 mL), dried over anhydrous sodium sulphate. Removal of solvent gave a residue which was purified by column chromatography (PE/EA=2/1) to obtain 66.0 mg (60.9%) of the title compound.

¹H NMR (400 MHz, CDCl₃) δ 8.59 (d, J=1.8 Hz, 1H), 8.13 (d, J=1.5 Hz, 1H), 8.07 (s, 1H), 7.79 (d, J=3.2 Hz, 1H), 7.33 (d, J=3.2 Hz, 1H), 6.26 (d, J=5.5 Hz, 1H), 6.00 (dd, J=11.7, 5.5 Hz, 1H), 5.58 (d, J=2.5 Hz, 1H), 5.22 (dd, J=11.7, 3.0 Hz, 1H), 4.72 (dd, J=7.4, 4.8 Hz, 1H), 4.10-3.99 (m, 3H), 3.42 (s, 1H), 1.98 (s, 2H), 1.92 (d, J=1.0 Hz, 6H).

ESI-MS m/z calcd for $[C_{23}H_{21}BrF_3N_5O_7S_2]^+$ [M+H]⁺: 679.0; found: 680.0.

i27) 3-Bromo-4-fluoro-phenyl 2,4,6-tri-O-acetyl-3-deoxy-3-[4-(2-thiazolyl)-1H-1,2,3-triazol-1-yl]-1-thio-α-D-galactopyranoside O-[(3-bromo-4-fluorophenyl)] N,N-dimethylcarbamothioate

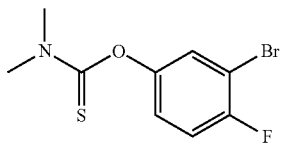

To a solution of 3-bromo-4-fluoro-phenol (2.00 g, 10.5 mmol) in N,N-dimethylformamide (20 mL) was added NaH (0.481 g, 60% in mineral, 12.5 mmol) at 0° C., then the mixture was stirred at 0° C. for 30 min. dimethylthiocarbamoyl chloride (1.55 g, 12.6 mmol) was added to the mixture, then it was stirred at room temperature for 20 h. TLC analysis indicated formation of product. The reaction mixture was quenched with water (150 mL) and extracted with EtOAc (50 mL×3). The combined organic layers were washed with brine (80 mL), dried over Mg₂SO₄, filtered and concentrated in vacuo to afford crude product, which was purified by flash chromatography (EA:PE=0~40%, ISCO® 40 g, 40 mL/min, normal phase silica, uv254). 2.2 g (75.5%) of the title compound as a gray solid was obtained.

ESI-MS m/z calcd for $[C_9H_9BrFNOS]^+$ [M+H]⁺: 277.0; found: 278.0.

S-[(3-bromo-4-fluorophenyl)] N,N-dimethylcarbamothioate

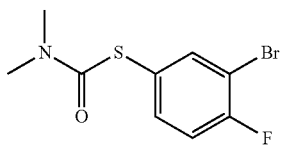

O-[(3-bromo-4-fluorophenyl)] N,N-dimethylcarbamothioate (2.4 g, 8.63 mmol) was dissolved in phenoxybenzene (20 mL), then the mixture was stirred at 260° C. for 2 hours. TLC analysis indicated the total consumption of the starting material. The reaction mixture was cooled and purified by silica gel column chromatography using a gradient of EA/PE from 0~40%. This gave the title compound 2.0 g (83.3%) as a yellow solid. ESI-MS m/z calcd for $[C_8H_9ClN_2OS]^+$ [M+H]⁺: 277.0; found: 278.0.

3-bromo-4-fluorobenzenethiol

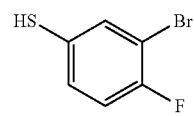

To a solution of S-[(3-bromo-4-fluorophenyl)] N,N-dimethylcarbamothioate (834 mg, 3.00 mmol) in EtOH (15.0 mL) was added water (5 mL) and KOH (337 mg, 6.00 mmol). The reaction was stirred at 70° C. for 16 h. The mixture was concentrated and the residue was used for next step directly without further purification.

ESI-MS m/z calcd for $[C_6H_4BrFS]^-$ [M−H]⁻: 205.9; found: 205.0.

3-Bromo-4-fluoro-phenyl 2,4,6-tri-O-acetyl-3-azido-3-deoxy-1-thio-α-D-galactopyranoside

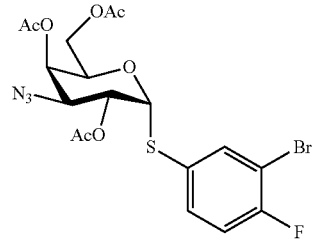

To a solution of 3-bromo-4-fluorobenzenethiol (518 mg, 2.50 mmol) in DMF (10 mL) was added Cs₂CO₃ (326 mg, 1.00 mmol), the mixture was stirred at room temperature for 30 min. 2,4,6-tri-O-acetyl-3-azido-1-chloro-3-deoxy-β-D-galactopyranoside (350 mg, 1.00 mmol) was added to solution. The reaction mixture was stirred at room temperature for 20 h. Water (40 mL) and EtOAc (100 mL) were added and the phases were separated. The organic phase was washed with water and brine, dried over Na₂SO₄, filtered and concentrated in vacuo to afford crude product, which was purified by silica gel column chromatography (EtOAc/Petrol ether, 70%) to give the title compound as a white solid, 140 mg (26.9%).

¹H NMR (400 MHz, CDCl₃) δ 7.61 (dd, J=6.4, 2.2 Hz, 1H), 7.31 (ddd, J=8.5, 4.5, 2.2 Hz, 1H), 7.01 (t, J=8.4 Hz, 1H), 5.83 (d, J=5.5 Hz, 1H), 5.41 (d, J=2.7 Hz, 1H), 5.19 (dd, J=11.0, 5.5 Hz, 1H), 4.67-4.46 (m, 1H), 4.05 (dd, J=11.6, 5.0 Hz, 1H), 3.95 (dd, J=11.6, 7.6 Hz, 1H), 3.87 (dd, J=10.9, 3.3 Hz, 1H), 2.13 (s, 3H), 2.09 (s, 3H), 1.96 (s, 3H).

ESI-MS m/z calcd for $[C_{18}H_{19}BrFN_3O_7S]^-$ [M+NH₄]⁺: 519.0; found: 537.0.

3-Bromo-4-fluoro-phenyl 2,4,6-tri-O-acetyl-3-deoxy-3-[4-(2-thiazolyl)-1H-1,2,3-triazol-1-yl]-1-thio-α-D-galactopyranoside

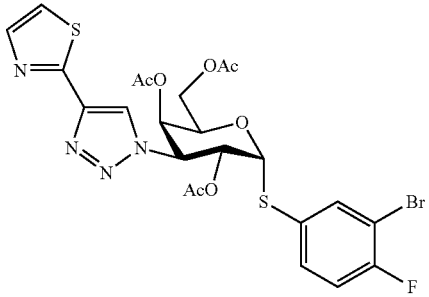

3-Bromo-4-fluoro-phenyl 2,4,6-tri-O-acetyl-3-azido-3-deoxy-1-thio-α-D-galactopyranoside (140 mg, 0.269 mmol), TEA (0.113 mL) 0.807 mmol), Copper(I)Iodide (15.4 mg, 0.0807 mmol), CsF (40.9 mg, 0.269 mmol) and trimethyl(2-thiazol-2-ylethynyl)silane (97.6 mg, 0.538 mmol) were dissolved in CH$_3$CN (10 mL). The reaction was stirred at room temperature overnight under N$_2$. The mixture was extracted with CH$_2$CL$_2$ (5 mL×2), the combined organic phase were washed with brine, dried over Na$_2$SO$_4$, filtered and concentrated in vacuo to afford crude product, which was purified by silica gel column chromatography (PE/EA=2/1) to give 80.0 mg (64.6%) of the title compound. ESI-MS m/z calcd for [C$_{23}$H$_{22}$BrFN$_4$O$_7$S$_2$]$^+$ [M+H]$^-$: 628.0; found: 629.0.

i28) 2,5-Dichlorophenyl 2,4,6-tri-O-acetyl-3-deoxy-3-[4-(2-thiazolyl)-1H-1,2,3-triazol-1-yl]-1-thio-α-D-galactopyranoside 2,5-Dichlorophenyl 2,4,6-tri-O-acetyl-3-azido-3-deoxy-1-thio-α-D-galactopyranoside

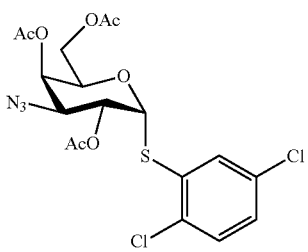

2,4,6-tri-O-Acetyl-3-azido-1-chloro-3-deoxy-β-D-galactopyranoside (350 mg, 1.00 mmol) and 2,5-dichlorobenzenethiol (358 mg, 2.00 mmol) were dissolved in N,N-Dimethylformamide (10.0 mL). Cs$_2$CO$_3$ (652 mg, 2.00 mmol) was added. The mixture was stirred at room temperature overnight. EtOAc (100 mL) was added. The reaction mixture was washed by water, brine, dried over Na$_2$SO$_4$, filtered and concentrated to afford crude product, which was purified by chromatography on silica gel column using a gradient of EtOAc/PE (40%) to afford the title compound as a white solid, 200 mg (40.6%).
ESI-MS m/z calcd for [C$_{18}$H$_{23}$Cl$_2$N$_4$O$_7$S]$^-$ [M+NH$_4$]$^+$: 509.0; found: 509.0.

2,5-Dichlorophenyl 2,4,6-tri-O-acetyl-3-deoxy-3-[4-(2-thiazolyl)-1H-1,2,3-triazol-1-yl]-1-thio-α-D-galactopyranoside

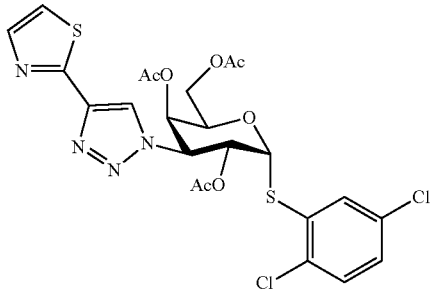

2,5-Dichlorophenyl 2,4,6-tri-O-acetyl-3-azido-3-deoxy-1-thio-α-D-galactopyranoside (200 mg, 0.406 mmol) and trimethyl(2-thiazol-2-ylethynyl)silane (147 mg, 0.812 mmol) were dissolved in acetonitrile (6.00 mL). Copper(I) Iodide (23.2 mg, 0.122 mmol), TEA (0.170 mL, 1.22 mmol) and CsF (61.7 mg, 0.406 mmol) were added. The reaction mixture was stirred at room temperature over night. EtOAc (100 mL) was added and the reaction mixture was washed by water (100 mL), brine (150 mL), dried over Na$_2$SO$_4$, filtered and concentrated to afford crude product, which was purified by chromatography on silica gel column using a gradient of EtOAc/PE (40%) to afford the title compound as a white solid, 170 mg (69.6%).

ESI-MS m/z calcd for [C$_{23}$H$_{23}$Cl$_2$N$_4$O$_7$S$_2$]$^+$ [M+H]$^+$: 601.0; found: 601.0.

i29) 3,4-Dichlorophenyl 2,4,6-tri-O-acetyl-3-deoxy-3-[4-bromo-(thiazol-2-yl)-1H-1,2,3-triazol-1-yl]-1-thio-α-D-galactopyranoside 2-(4-bromothiazol-2-yl)ethynyl-trimethyl-silane

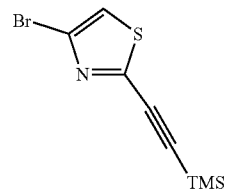

To a solution of 2,4-dibromothiazole (2.00 g, 8.23 mmol) in CH$_3$CN (30 mL) was added Copper(I)Iodide (78.4 mg, 0.412 mmol), TEA (5.74 mL), PdCl$_2$(PPh$_3$)$_2$ (289 mg, 0.412 mmol), ethynyl(trimethyl)silane (1.21 g, 12.3 mmol). The mixture was heated under N$_2$ at 50 □ for 20 h. Removal of solvent gave a residue which was purified by column chromatography (PE/EA=10/1) to obtain 300 mg (14%) of the title compound.

ESI-MS m/z calcd for [C$_8$H$_{10}$BrNSSi]$^+$ [M+H]$^-$: 259; found: 259.

3,4-Dichlorophenyl 2,4,6-tri-O-acetyl-3-deoxy-3-[4-bromo-(thiazol-2-yl)-1H-1,2,3-triazol-1-yl]-1-thio-α-D-galactopyranoside

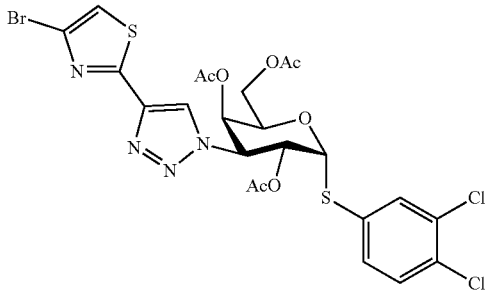

To a solution of 3.4-dichlorophenyl 2,4,6-tri-O-acetyl-3-azido-3-deoxy-1-thio-α-D-galactopyranoside (200 mg, 0.406 mmol) in CH$_3$CN (5 mL) were added TEA (0.283 mL), Copper(I)Iodide (23.2 mg, 0.122 mmol), CsF (92.6 mg, 0.609 mmol), 2-(4-bromothiazol-2-yl)ethynyl-trimethyl-silane (159 mg, 0.609 mmol). The reaction was stirred at room temperature for 20 h under a nitrogen gas atmosphere. Water (10 mL) and CH$_2$Cl$_2$ (10 mL) were added. The aqueous phase was extracted with CH$_2$Cl$_2$ (5 mL×2) and the combined organic phases were washed with water (20 mL) and brine (20 mL), dried over anhydrous sodium sulphate, filtered and concentrated in vacuo to afford crude product, which was purified by column chromatography (PE/EA=2/1) to give the title compound as a white solid, 120 mg (43.4%).

ESI-MS m/z calcd for $[C_{23}H_{21}BrCl_2N_4O_7S_2]^+$ $[M+H]^-$: 677.9; found: 679.0.

i30) 3,4-Dichlorophenyl 2,4,6-tri-O-acetyl-3-deoxy-3-[4-(5-fluoro-thiazol-2-yl)-1H-1,2,3-triazol-1-yl]-1-thio-α-D-galactopyranoside

Tert-Butyl thiazol-2-ylcarbamate

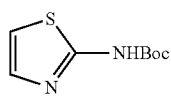

(Boc)$_2$O (52.305 g, 240 mmol) was added dropwise to a solution of thiazol-2-amine (20.0 g, 200 mmol) in tetrahydrofuran solution (150 mL) followed by stirring at room temperature for 16 h. The solvent was removed in vacuo to afford crude product, which was pulverized in EtOAc and filtered. 19.0 g (47.5%) of the title compound as a white solid was obtained.

$^1$H NMR (400 MHz, CDCl$_3$) δ 12.20 (s, 1H), 7.38 (d, J=3.6 Hz, 1H), 6.88 (d, J=3.6 Hz, 1H), 1.59 (s, 9H).

ESI-MS m/z calcd for $[C_8H_{12}N_2O_2S]^+$ $[M+Na]^+$: 223.1; found: 223.0.

tert-Butyl N-(5-fluorothiazol-2-yl)carbamate

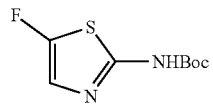

To a solution of tert-butyl thiazol-2-ylcarbamate (17.0 g, 484.9 mmol) in THF (100 mL) was added dropwise a solution of n-butyllithium in hexane (74.7 mL, 187 mmol, 2.5 mol/L) at −78° C. over 30 minutes, and the mixture was warmed to −10° C. over 1 h.

The mixture was cooled again to −78° C., and then N-fluorobenzene-sulfonylimide (2.362 g, 7.49 mmol) was added. An acetone-dry ice bath was removed, and the mixture was stirred for 30 minutes. Then, the reaction mixture was poured into cooled water (100 mL), and the reaction mixture was extracted with ethyl acetate (20 mL×3). The combined organic layers were washed with 2 N HCl, water and brine and dried over anhydrous MgSO$_4$ and concentrated. The residue was purified by silica gel column chromatography (EtOAc/Petroleum ether=15%) to give the title compound as a white solid, 10.5 g (56.7%). $^1$H NMR (400 MHz, CDCl$_3$) δ 12.20 (s, 1H), 6.88 (d, J=3.6 Hz, 1H), 1.59 (s, 9H). ESI-MS m/z calcd for $[C_8H_{11}FN_2O_2S]^+$ $[M+H-56]^+$: 163.0; found: 163.0.

5-Fluorothiazol-2-amine

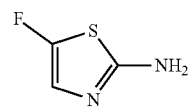

TFA (27.43 g, 241.00 mmol) was added to a solution of tert-butyl N-(5-fluorothiazol-2-yl)carbamate (10.50 g, 48.1 mmol) in CH$_2$Cl$_2$ (100 mL). The reaction mixture was stirred at room temperature for 3 h and the solvents were removed in vacuo. The residue was neutralised with aq NaHCO$_3$ followed by extraction with CH$_2$Cl$_2$ (20 mL×3). The combined organic layers were washed with brine, filtered and concentrated in vacuo to afford the title compound as a gray solid, 5.2 g (91.5%).

$^1$H NMR (400 MHz, CDCl$_3$) δ 6.65 (d, J=2.6 Hz, 1H), 4.69 (brs, 2H). ESI-MS m/z calcd for $[C_3H_3FN_2S]^+$ $[M+H]^+$: 119.0; found: 119.0.

2-Bromo-5-fluorothiazole

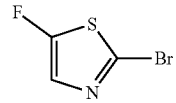

To a solution of 5-fluorothiazol-2-amine (3.425 g, 29.0 mmol) in MeCN (50 mL) was added iso-amylnitrite (5.095 g, 43.5 mmol) at 0° C. followed by copper bromide (5.407 g, 37.7 mmol). The reaction mixture was stirred at room temperature for 3 h. The mixture was filtered and concentrated in vacuo to afford crude product, which was purified by flash chromatography (Petrol ether/pentane, 0%~10%) to give the title compound as a yellow oil, 1.760 g (33.4%). ESI-MS m/z calcd for $[C_3HBrFNS]^+$ $[M+H]^+$: 181.9; found: 181.9.

5-fluoro-2-((trimethylsilyl)ethynyl)thiazole

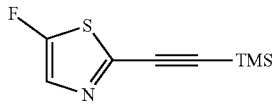 [SMILES: C[Si](C)(C)C#Cc1ncc(F)s1]

2-Bromo-5-fluorothiazole (1.76 g, 9.67 mmol), copper(I) Iodide (92.1 mg, 0.483 mmol), $Et_3N$ (4.892 g, 48.3 mmol), $PdCl_2(PPh_3)_2$ (340 mg, 0.483 mmol) and ethynyl(trimethyl)silane (1.425 g, 14.5 mmol) were dissolved in THF (50 mL). The mixture was stirred at 50° C. for 20 h under a nitrogen atmosphere. The mixture was extracted with EtOAc (10 mL×3) and the combined organic layers were washed with brine (20 mL), dried over $Na_2SO_4$, filtered and concentrated in vacuo to afford crude product, which was purified by silica gel column chromatography using a gradient of Petrol ether/pentane (0%~10%) to give the title compound as a brown oil, 350 mg (18.2%). ESI-MS m/z calcd for $[C_8H_{10}FNSSi]^+$ $[M+H]^+$: 200.0; found: 200.0.

3,4-Dichlorophenyl 2,4,6-tri-O-acetyl-3-deoxy-3-[4-(5-fluoro-thiazol-2-yl)-1H-1,2,3-triazol-1-yl]-1-thio-α-D-galactopyranoside

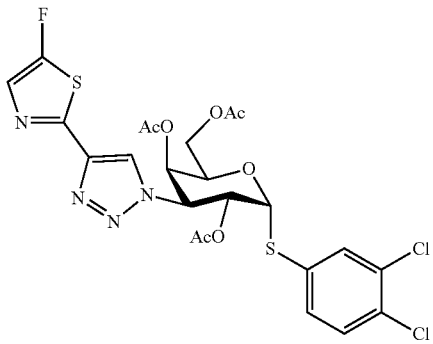

To a solution of 2,4,6-tri-O-acetyl-3-azido-3-deoxy-1-thio-α-D-galactopyranoside (259 mg, 0.527 mmol) in MeCN (15 mL) was added $Et_3N$ (302 mg, 2.99 mmol), copper(I)Iodide (33.4 mg, 0.176 mmol), CsF (133 mg, 0.878 mmol), 5-fluoro-2-((trimethylsilyl)ethynyl)thiazole (350 mg, 0.502 mmol). The reaction was stirred at room temperature for 20 h under a nitrogen atmosphere. The mixture was extracted with $CH_2Cl_2$ (5 mL×2) and the combined organic phases were washed with water (20 mL), brine (20 mL), dried over $Na_2SO_4$, filtered and concentrated in vacuo to afford crude product, which was purified by silica gel column chromatography (EtOAc/Petrol ether=1/2) to give the title compound as a grey solid, 100 mg (9.19%).

ESI-MS m/z calcd for $[C_{22}H_{21}Cl_2FN_4O_7S_2]^+$ $[M+H]^+$: 619.0; found: 619.0.

i31) 3,4-Dichlorophenyl 2,4,6-tri-O-acetyl-3-deoxy-3-[4-(4-chloro-thiazol-2-yl)-1H-1,2,3-triazol-1-yl]-1-thio-α-D-galactopyranoside 4-chloro-2-((trimethylsilyl)ethynyl)thiazole

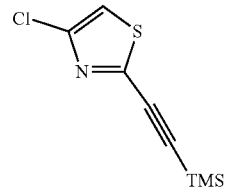 [SMILES: C[Si](C)(C)C#Cc1nc(Cl)cs1]

To a solution of 2-bromo-4-chlorothiazole (500 mg, 2.52 mmol) in THF (10 mL) was added Copper(I)Iodide (205 mg, 0.108 mmol), TEA (0.300 mL, 2.15 mmol), $PdCl_2(PPh_3)_2$ (75.6 mg, 0.108 mmol), ethynyl(trimethyl)silane (212 mg, 2.15 mmol). The mixture was stirred at room temperature for 20 h under a nitrogen atmosphere. The solvents were removed in vacuo to afford crude product, which was purified by silica gel column chromatography (EtOAc/Petrol ether=1/10) to give the title compound as a gray oil, 150 mg (27.6%).

GC-MS, ESI-MS m/z calcd for $[C_8H_{10}ClNSSi]$ $[M]$: 216.0; found: 216.0.

3,4-Dichlorophenyl 2,4,6-tri-O-acetyl-3-deoxy-3-[4-(4-chloro-thiazol-2-yl)-1H-1,2,3-triazol-1-yl]-1-thio-α-D-galactopyranoside

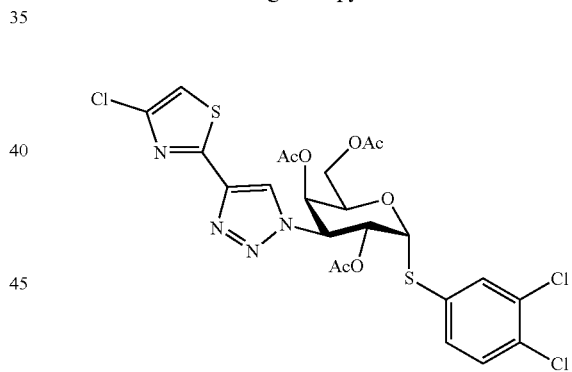

To a solution of 3,4-dichlorophenyl 2,4,6-tri-O-acetyl-2,4,6-tri-O-acetyl-3-azido-3-deoxy-1-thio-α-D-galactopyranoside (150 mg, 0.305 mmol) in MeCN (5 mL) were added $Et_3N$ (0.212 mL, 1.52 mmol), Copper(I)Iodide (17.4 mg, 0.0914 mmol), CsF (69.4 mg, 0.457 mmol), 4-chloro-2-((trimethylsilyl)ethynyl)thiazole (98.6 mg, 0.457 mmol). The mixture was stirred at room temperature for 20 h under a nitrogen atmosphere. Water (10 mL) and $CH_2CL_2$ (10 mL) were added. The aqueous phase was extracted with $CH_2Cl_2$ (5 mL×2), the combined organic phases were washed with water (20 mL) and brine (20 mL), dried over anhydrous $Na_2SO_4$, filtered and concentrated in vacuo to afford crude product, which was purified by silica gel column chromatography (EtOAc/Petrol ether=1/2) to give the title compound as a gray solid, 70.0 mg (36.1%).

ESI-MS m/z calcd for $[C_{23}H_{21}Cl_3N_4O_7S_2]^+$ $[M+H]^+$: 635.0; found: 635.0.

i32) 3,4-Dichlorophenyl 2,4,6-tri-O-acetyl-3-deoxy-3-[4-(4-trifluoromethyl-thiazol-2-yl)-1H-1,2,3-triazol-1-yl]-1-thio-α-D-galactopyranoside 4-(trifluoromethyl)-2-((trimethylsilyl)ethynyl)thiazole

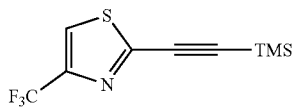

To a solution of 2-bromo-4-(trifluoromethyl)thiazole (500 mg, 2.15 mmol) in THF (10 mL) was added Copper(I)Iodide (205 mg, 0.108 mmol), Et$_3$N (0.300 mL, 2.15 mmol), PdCl$_2$(PPh$_3$)$_2$ (75.6 mg, 0.108 mmol), ethynyl(trimethyl)silane (212 mg, 2.15 mmol). The mixture was stirred at room temperature for 20 h under a nitrogen atmosphere. The solvents were removed in vacuo to afford crude product, which was purified by silica gel column chromatography (EtOAc/Petrol ether=1/10) to give the title compound a s a grey oil, 250 mg (46.5%). GC-MS, ESI-MS m/z calcd for [C$_9$H$_{10}$FFNSSi] [M]: 249.0; found: 249.0.

3,4-Dichlorophenyl 2,4,6-tri-O-acetyl-3-deoxy-3-[4-(4-trifluoromethyl-thiazol-2-yl)-1H-1,2,3-triazol-1-yl]-1-thio-α-D-galactopyranoside

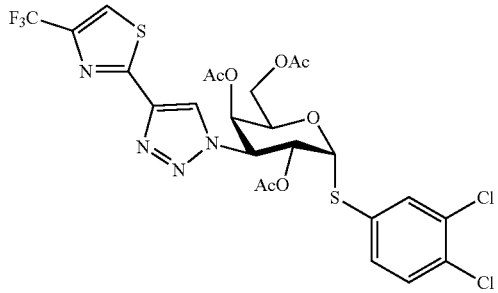

To a solution of 2,4,6-tri-O-acetyl-3-azido-3-deoxy-1-thio-α-D-galactopyranoside (150 mg, 0.305 mmol) in MeCN (5 mL) were added Et$_3$N (0.212 mL) 1.52 mmol), Copper(I)Iodide (17.4 mg, 0.0914 mmol), CsF (69.4 mg, 0.457 mmol), trimethyl-[2-[4-(trifluoromethyl)thiazol-2-yl] ethynyl]silane (119 mg, 0.477 mmol). The reaction was stirred at room temperature for 20 h under a nitrogen atmosphere. Water (10 mL) and CH$_2$Cl$_2$ (10 mL) were added. The aqueous phase was extracted with CH$_2$Cl$_2$ (5 mL×2), the combined organic phases were washed with water (20 mL) and brine (20 mL), dried over anhydrous Na$_2$SO$_4$, filtered and concentrated in vacuo to afford crude product, which was purified by silica gel column chromatography (EtOAc/Petrol ether=1/2) to obtain the title compound, 110 mg (53.9%). ESI-MS m/z calcd for [C$_{24}$H$_{21}$Cl$_2$F$_3$N$_4$O$_7$S$_2$]$^+$[M+H]$^+$: 669.0; found: 669.0.

REFERENCES

Aits S, Kricker J, Liu B, Ellegaard A M, Hämälistó S, Tvingsholm S, Corcelle-Termeau E, Hogh S, Farkas T, Holm Jonassen A, Gromova I, Mortensen M, Jäättelä M. (2015) Sensitive detection of lysosomal membrane permeabilization by lysosomal galectin puncta assay Autophagy. 2015; 11(8):1408-24.

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. Infect. Immun. Vol. 69: 832-837.

Arthur C M, Baruffi M D, Cummings R D, Stowell S R. (2015) Evolving mechanistic insights into galectin functions. Methods Mol Biol. 1207:1-35.

Helen Blanchard, Khuchtumur Bum-Erdene, Mohammad Hussaini Bohari & Xing Yu (2016) Galectin-1 inhibitors and their potential therapeutic applications: a patent review, Expert Opinion on Therapeutic Patents, 26:5, 537-554, DOI: 10.1517/13543776.2016.1163338

Blidner A G, Méndez-Huergo S P, Cagnoni A J, Rabinovich G A. (2015) Re-wiring regulatory cell networks in immunity by galectin-glycan interactions. FEBS Lett. 2015 Sep. 6. pii: S0014-5793(15)00807-8.

Chen, W.-S., Leffler H., Nilsson, U. J., Panjwani, N. (2012). Targeting Galectin-1 and Galectin-3 Attenuates VEGF-A-induced Angiogenesis; Mol. Biol. Cell (suppl), Abstract No. 2695.

Cooper, D. N.; Massa, S. M.; Barondes, S. H. (1991) Endogenous muscle lectin inhibits myoblast adhesion to laminin. The Journal of Cell Biology 115, 1437-1448.

Cumpstey, I., Carlsson, S., Leffler, H. and Nilsson, U. J. (2005) Synthesis of a phenyl thio-ß-D-galactopyranoside library from 1,5-difluoro-2,4-dinitrobenzene: discovery of efficient and selective monosaccharide inhibitors of galectin-7. Org. Biomol. Chem. 3: 1922-1932.

Cumpstcy, I., Sundin, A., Leffler, H. and Nilsson, U. J. (2005) C$_2$-Symmetrical thiodigalactoside bis-benzamido derivatives as high-affinity inhibitors of galectin-3: Efficient lectin inhibition through double arginine-arene interactions. Angew. Chem. Int. Ed. 44: 5110-5112.

Cumpstcy, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. Chem. Eur. J. 14: 4233-4245.

Delaine, T., Cumpstey, I., Ingrassia, L., Le Mercier, M., Okechukwu, P., Leffler, H., Kiss, R., and Nilsson, U. J. (2008). Galectin-Inhibitory Thiodigalactoside Ester Derivatives Have Anti-Migratory Effects in Cultured Lung and Prostate Cancer Cells. J Med Chem 51; 8109-8114.

Demotte, N., Wieers, G., van der Smissen, P., Moser, M., Schmidt, C., Thielemans, K., et al., (2010). Cancer Res. 70; 7476-7488.

Dings, R. P. M.; Miller, M. C.; Nesmelova, I.; Astorgues-Xerri, L.; Kumar, N.; Serova, M.; Chen, X.; Raymond, E.; Hoye, T. R.; Mayo, K. H. Journal of medicinal . . . 2012, 55, 5121-5129.

Ebrahim A H, Alalawi Z, Mirandola L, Rakhshanda R, Dahlbeck S, Nguyen D, Jenkins M1, Grizzi F, Cobos E, Figueroa J A, Chiriva-Internati M (2014 Galectins in cancer: carcinogenesis, diagnosis and therapy. Ann Transl Med. 2014 September; 2(9):88.

Elola M T, Blidner A G, Ferragut F, Bracalente C, Rabinovich G A. (2015) Assembly, organization and regulation of cell-surface receptors by lectin-glycan complexes. Biochem J. 2015 Jul. 1; 469(1):1-16.

Farkas, I.; Szabó, I. F.; Bognár, R.; Anderle, D. Carbohydr. Res. 1976, 48, 136-138.

Giguère, D.; Bonin, M.-A.; Cloutier, P.; Patnam, R.; St-Pierre, C.; Sato, S.; Roy, R. Bioorganic & Medicinal Chemistry 2008, 16, 7811-7823.

Giguère, D.; André, S.; Bonin, M.-A.; Bellefleur, M.-A.; Provencal, A.; Cloutier, P.; Pucci, B.; Roy, R.; Gabius, H.-J. Bioorganic & Medicinal Chemistry 2011, 19, 3280-3287.

Giguere, D., Patnam, R., Bellefleur, M.-A., St.-Pierre, C., Sato, S., and Roy, R. (2006). Carbohydrate triazoles and isoxazoles as inhibitors of galectins-1 and -3. Chem Commun: 2379-2381.

Glinsky, G. V., Price, J. E., Glinsky, V. V., Mossine, V. V., Kiriakova, G., and Metcalf, J. B. (1996). Cancer Res 56: 5319-5324.

Glinsky, V. V., Kiriakova, G., Glinskii, O. V., Mossine, V. V., Mawhinney, T. P., Turk, J. R., Glinskii, A. B., Huxley, V. H., Price, J. E., and Glinsky, G. V. (2009). Synthetic Galectin-3 Inhibitor Increases Metastatic Cancer Cell Sensitivity to Taxol-Induced Apoptosis In Vitro and In Vivo. *Neoplasia* 11; 901-909.

van Hattum, H.; Branderhorst, H. M.; Moret, E. E.; Nilsson, U. J.; Leffler, H.; Pieters, R. J. J. Med. Chem. 2013, 56, 1350-1354. Huflejt, M. E. and Leffler, H. (2004) Galectin-4 in normal tissues and cancer. *Glycoconj. J.* 20: 247-255.

Hockl P F, Wolosiuk A, Pérez-Sáez JM1, Bordoni AV2, Croci DO3, Toum-Terrones Y2, Soler-Illia GJ4, Rabinovich GA5. Glyco-nano-oncology: Novel therapeutic opportunities by combining small and sweet. Treatment of cancer Pharmacol Res. 2016 Feb. 4. pii: S1043-6618(16) 00042-6. doi: 10.1016/j.phrs.2016.02.005. [Epub ahead of print]

Ingrassia et al. (2006) A Lactosylated Steroid Contributes in Vivo Therapeutic Benefits in Experimental Models of Mouse Lymphoma and Human Glioblastoma. *J. Med. CHem.* 49: 1800-1807.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast *Cancer. Clin. Cancer Res.* 9: 2374-2383.

Kathiriya, J. J. et al. Galectin-1 inhibition attenuates profibrotic signaling in hypoxia-induced pulmonary fibrosis. Cell Death Discovery 3, 17010-13 (2017).

Kouo, T., Huang, L., Pucsek, A. B., Cao, M., Solt, S., Armstrong, T., Jaffee, E. (2015) *Cancer Immonol. Res.* 3: 412-23

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A Synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Lepur A, Salomonsson E, Nilsson U J, Leffler H. (2012) Ligand induced galectin-3 protein self-association. J Biol Chem. 2012 Jun. 22; 287(26):21751-6.

Lin, C.-I., Whang, E. E., Donner, D. B., Jiang, X., Price, B. D., Carothers, A. M., Delaine, T., Leffler, H., Nilsson, U. J., Nose, V., et al. (2009). Galectin-3 Targeted Therapy with a Small Molecule Inhibitor Activates Apoptosis and Enhances Both Chemosensitivity and Radiosensitivity in Papillary Thyroid Cancer. *Mol Cancer Res* 7: 1655-1662.

MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. *J. Immun.* 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. *Am. J. Resp. Crit. Care Med.*, in press.

Massa, S. M., Cooper, D. N. W., Leffler, H., Barondes, S. H. (1993) L-29, an endogenous lectin, binds to glycoconjugate ligands with positive cooperativity. *Biochemistry* 32: 260-267.

Melero, I., Berman, D. M., Aznar, M. A., Korman, A. J., Gracia, J. L. P., Haanen, J. (2015) *Nature Reviews Cancer.* 15: 457-472

Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. *Science* 306: 120-124.

Perillo, N. L.; Pace, K. E.; Seilhamer, J. J.; Baum, L. G. Nature 1995, 378, 736-739.

Pienta, K. J., Naik, H., Akhtar, A., Yamazaki, K., Reploge, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Poirier, F. Roles of galectins in vivo. Biochem. Soc. Symp. 2002:95-103.

Ramos-Soriano, J.; Niss, U.; Angulo, J.; Angulo, M.; Moreno-Vargas, A. J.; Carmona, A. T.; Ohlson, S.; Robina, I. Chem. Eur. J. 2013, 19, 17989-18003.

Ruvolo, P. P. *Biochim. Biophys Acta.* Molecular cell research (2015) E-pub ahead of print, title: Galectin-3 as a guardian of the tumor microenvironment, published on-line 8 Apr. 2015: (http://www.sciencedirectcom/science/article/pii/S0167488915002700), Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejler, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Sörme, P., Qian, Y., Nyholm, P.-G., Leffler, H., Nilsson, U. J. (2002) Low micromolar inhibitors of galectin-3 based on 3'-derivatization of N-acetyllactosamine. *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., Magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Tejler, J.; Tullberg, E.; Frejd, T.; Leffler, H.; Nilsson, U. J. Carbohydrate Research 2006, 341, 1353-1362.

Tejler, J.; Salameh, B.; Leffler, H.; Nilsson, U. J. Org. Biomol. Chem. 2009, 7, 3982. Thijssen, V. L., Poirer, F., Baum, L. G., and Griffloen, A. W. (2007). Galectins in the tumor endothelium: opportunities for combined cancer therapy. Blood 110: 2819-2827.

Toscano, M. A., Bianco, G. A., Ilarregui, J. M., Croci, D. O., Corrcale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8: 825-834.

We claim:

1. A D-galactopyranose compound of formula (1)

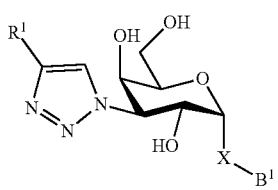

(1)

wherein the pyranose ring is a-D-galactopyranose, $R^1$ is a five or six membered heteroaromatic ring selected from the group consisting of formulas 2 to 9, wherein the asterix * indicates the carbon atom of the heteroaromatic ring that is covalently attached to the triazole group of formula (1):

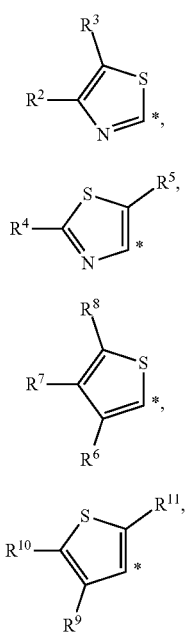

2

3

4

5

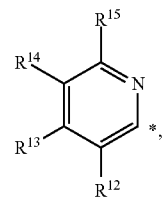

6

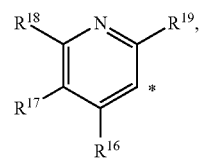

7

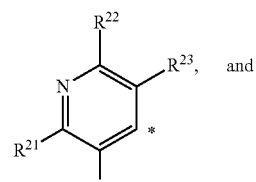

8 and

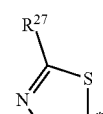

9 wherein $R^2$ to $R^{23}$ and $R^{27}$ are independently selected from H; halogen; OH; CN; SH; S—$C_{1-3}$ alkyl; $C_{1-3}$ alkyl, optionally substituted with a F; cyclopropyl, optionally substituted with a F; iso-propyl, optionally substituted with a F; O-cyclopropyl optionally substituted with a F; O-isopropyl optionally substituted with a F; $OC_{1-3}$ alkyl optionally substituted with a F; $NR^{24}R^{25}$, wherein $R^{24}$ is selected from H, and $C_{1-3}$ alkyl, and $R^{25}$ is selected from H, $C_{1-3}$ alkyl, and $COR^{26}$, wherein $R^{26}$ is selected from H, and $C_{1-3}$ alkyl;

X is selected from S, SO, and $SO_2$;

$B^1$ is selected from a) a $C_{1-6}$ alkyl or branched $C_{3-6}$ alkyl substituted with a five or six membered heteroaromatic ring, optionally substituted with a substituent selected from CN, a halogen, methyl optionally substituted with a F, $OCH_3$ optionally substituted with a F, $OCH_2CH_3$ optionally substituted with a F, OH, and $R^{27}$—CONH— wherein $R^{27}$ is selected from $C_{1-3}$ alkyl and cyclopropyl; or a $C_{1-6}$ alkyl substituted with a phenyl, optionally substituted with a substituent selected from CN, a halogen, methyl optionally substituted with a F, $OCH_3$ optionally substituted with a F, $OCH_2CH_3$ optionally substituted with a F, OH, and $R^{28}$—CONH— wherein $R^{28}$ is selected from $C_{1-3}$ alkyl and cyclopropyl; b) an aryl, optionally substituted with a group selected from a halogen; CN; —COOH; —$CONR^{29}R^{30}$, wherein $R^{29}$ and $R^{30}$ are independently selected from H, $C_{1-3}$ alkyl, cyclopropyl, and iso-propyl; $C_{1-3}$ alkyl, optionally substituted with a F; cyclopropyl, optionally substituted with a F; isopropyl, optionally substituted with a F; $OC_{1-3}$ alkyl, optionally substituted with a F; O-cyclopropyl, optionally substituted with a F; O-isopropyl, optionally substituted with a F; $NR^{31}R^{32}$, wherein $R^{31}$ and $R^{32}$ are independently selected from H, $C_{1-3}$ alkyl and isopropyl; OH; and $R^{33}$—CONH—, wherein $R^{33}$ is selected from $C_{1-3}$ alkyl and cyclopropyl; c) a $C_{5-7}$ cycloalkyl, optionally substituted with a substituent selected from a halogen, CN, methyl optionally substituted with a F, $OCH_3$ optionally substituted with a F, OCH$_2$CH$_3$ optionally substituted with a F, OH, and R$^{34}$—CONH— wherein R$^{34}$ is selected from C$_{1-3}$ alkyl and cyclopropyl; and d) a heterocycle, optionally substituted with a group selected from a halogen; CN; —COOH; —CONR$^{35}$R$^{36}$, wherein R$^{35}$ and R$^{36}$ are independently selected from H, C$_{1-3}$ alkyl, cyclopropyl, and iso-propyl; C$_{1-3}$ alkyl, optionally substituted with a F; cyclopropyl, optionally substituted with a F; isopropyl, optionally substituted with a F; OC$_{1-3}$ alkyl, optionally substituted with a F; O-cyclopropyl, optionally substituted with a F; O-isopropyl, optionally substituted with a F; NR$^{37}$R$^{38}$, wherein R$^{37}$ and R$^{38}$ are independently selected from H, C$_{1-3}$ alkyl and isopropyl; OH; and R$^{39}$—CONH— wherein R$^{39}$ is selected from C$_{1-3}$ alkyl and cyclopropyl; e) a C$_{1-6}$ alkyl or branched C$_{3-6}$ alkyl; or a pharmaceutically acceptable salt or solvate thereof.

2. The compound of claim 1, wherein R$^1$ is selected from formula 2 wherein R$^2$ and R$^3$ are independently selected from H, halogen, and C$_{1-3}$ alkyl, optionally substituted with a F.

3. The compound of claim 1, wherein R$^1$ is selected from formula 3 wherein R$^4$ and R$^5$ are independently selected from H, halogen, and C$_{1-3}$ alkyl.

4. The compound of claim 1, wherein R$^1$ is selected from formula 4 wherein R$^6$-R$^8$ are independently selected from H, halogen, and C$_{1-3}$ alkyl.

5. The compound of claim 1, wherein R$^1$ is selected from formula 5 wherein R$^9$-R$^{11}$ are independently selected from H, halogen, and C$_{1-3}$ alkyl.

6. The compound of claim 1, wherein R$^1$ is selected from formula 6 wherein R$^{12}$-R$^{15}$ are independently selected from H, halogen, and C$_{1-3}$ alkyl.

7. The compound of claim 1, wherein R$^1$ is selected from formula 7 wherein R$^{16}$-R$^{19}$ are independently selected from H, halogen, and C$_{1-3}$ alkyl.

8. The compound of claim 1, wherein R$^1$ is selected from formula 8 wherein R$^{20}$-R$^{23}$ are independently selected from H, halogen, and C$_{1-3}$ alkyl.

9. The compound of claim 1, wherein R$^1$ is selected from formula 9 wherein R$^{27}$ is selected from H, halogen, and C$_{1-3}$ alkyl.

10. The compound of claim 1, wherein X is S.

11. The compound of claim 1, wherein B$^1$ is selected from an aryl, optionally substituted with a group selected from halogen; CN; and methyl optionally substituted with a F.

12. The compound of claim 1, wherein B$^1$ is selected from a phenyl or phenyl substituted with one, two or three substituents selected from Cl, F, Br, CN, and CF$_3$.

13. The compound of claim 1, wherein B$^1$ is selected from a heterocycle, optionally substituted with a group selected from a halogen; CN; and a methyl optionally substituted with a F.

14. The compound of claim 1, wherein B$^1$ is selected from a pyridinyl, optionally substituted with a group selected from a halogen; CN; and a methyl optionally substituted with a F.

15. The compound of claim 1, wherein B$^1$ is selected from a pyridinyl, optionally substituted with one, or two substituents selected from Cl, Br, CN and CF$_3$.

16. The compound of claim 1 selected from:
3,4-Dichlorophenyl 3-deoxy-3-[4-(3-thiophenyl)-1H-1,2,3-triazol-1-yl]-1-thio-α-D-galactopyranoside,
2-Chloro-5-fluoro-benzonitril-4-yl 3-deoxy-3-[4-(3-thiophenyl)-1H-1,2,3-triazol-1-yl]-1-thio-α-D-galactopyranoside,
5-Bromopyridin-3-yl 3-deoxy-3-[4-(3-thiophenyl)-1H-1,2,3-triazol-1-yl]-1-thio-α-D-galactopyranoside,
5-Bromo-6-trifluoromethyl-pyridin-3-yl 3-deoxy-3-[4-(3-thiophenyl)-1H-1,2,3-triazol-1-yl]-1-thio-α-D-galactopyranoside,
3,5-Dichloro-4-fluoro-phenyl 3-deoxy-3-[4-(3-thiazolyl)-1H-1,2,3-triazol-1-yl]-1-thio-α-D-galactopyranoside,
3,4-Dichlorophenyl 3-deoxy-3-[4-(5-fluoro-2-pyridyl)-1H-1,2,3-triazol-1-yl]-1-thio-α-D-galactopyranoside,
5-Bromopyridin-3-yl 3-deoxy-3-[4-(2-thiophenyl)-1H-1,2,3-triazol-1-yl]-1-thio-α-D-galactopyranoside,
3,5-Dichloro-4-fluoro-phenyl 3-deoxy-3-[4-(2-thiophenyl)-1H-1,2,3-triazol-1-yl]-1-thio-α-D-galactopyranoside,
3,4-Dichlorophenyl 3-deoxy-3-[4-(5-fluoro-2-thiophenyl)-1H-1,2,3-triazol-1-yl]-1-thio-α-D-galactopyranoside,
5-Bromopyridin-3-yl 3-deoxy-3-[4-(4-thiazolyl)-1H-1,2,3-triazol-1-yl]-1-thio-α-D-galactopyranoside,
5-Bromo-6-trifluoromethyl-pyridin-3-yl 3-deoxy-3-[4-(4-thiazolyl)-1H-1,2,3-triazol-1-yl]-1-thio-α-D-galactopyranoside,
3,4-Dichlorophenyl 3-deoxy-3-[4-(4-thiazolyl)-1H-1,2,3-triazol-1-yl]-1-thio-α-D-galactopyranoside,
2-Chloro-benzonitril-4-yl 3-deoxy-3-[4-(4-thiazolyl)-1H-1,2,3-triazol-1-yl]-1-thio-α-D-galactopyranoside,
3,5-Dichloro-4-fluoro-phenyl 3-deoxy-3-[4-(4-thiazolyl)-1H-1,2,3-triazol-1-yl]-1-thio-α-D-galactopyranoside,
5-Bromopyridin-3-yl 3-deoxy-3-[4-(2-methyl-4-thiazolyl)-1H-1,2,3-triazol-1-yl]-1-thio-α-D-galactopyranoside,
2,6-Dichloro-bensonitrile-4-yl 3-deoxy-3-[4-(2-thiazolyl)-1H-1,2,3-triazol-1-yl]-1-thio-α-D-galactopyranoside,
3,4,5-Trichlorophenyl 3-deoxy-3-[4-(2-thiazolyl)-1H-1,2,3-triazol-1-yl]-1-thio-α-D-galactopyranoside,
3,4-Dichlorophenyl 3-deoxy-3-[4-(2-thiazolyl)-1H-1,2,3-triazol-1-yl]-1-thio-α-D-galactopyranoside,
3,4,5-Trichlorophenyl 3-deoxy-3-[4-(1,3,4-thiadiazol-2-yl)-1H-1,2,3-triazol-1-yl]-1-thio-α-D-galactopyranoside,
5-Bromopyridin-3-yl 3-deoxy-3-[4-(2-thiazolyl)-1H-1,2,3-triazol-1-yl]-1-thio-α-D-galactopyranoside,
5-Chloropyridin-3-yl 3-deoxy-3-[4-(2-thiazolyl)-1H-1,2,3-triazol-1-yl]-1-thio-α-D-galactopyranoside,
5-Bromo-2-cyano-pyridine-3-yl 3-deoxy-3-[4-(2-thiazolyl)-1H-1,2,3-triazol-1-yl]-1-thio-α-D-galactopyranoside,
5-Chloro-6-cyano-pyridine-3-yl 3-deoxy-3-[4-(2-thiazolyl)-1H-1,2,3-triazol-1-yl]-1-thio-α-D-galactopyranoside,
3,5-Dichlorophenyl 3-deoxy-3-[4-(2-thiazolyl)-1H-1,2,3-triazol-1-yl]-1-thio-α-D-galactopyranoside
3-Bromo-4-chlorophenyl 3-deoxy-3-[4-(2-thiazolyl)-1H-1,2,3-triazol-1-yl]-1-thio-α-D-galactopyranoside,
5-Bromo-6-trifluoromethyl-pyridine-3-yl 3-deoxy-3-[4-(2-thiazolyl)-1H-1,2,3-triazol-1-yl]-1-thio-α-D-galactopyranoside,
3-Bromo-4-fluoro-phenyl 3-deoxy-3-[4-(2-thiazolyl)-1H-1,2,3-triazol-1-yl]-1-thio-α-D-galactopyranoside,
2,5-Dichlorophenyl 3-deoxy-3-[4-(2-thiazolyl)-1H-1,2,3-triazol-1-yl]-1-thio-α-D-galactopyranoside,
3,4-Dichlorophenyl 3-deoxy-3-[4-(4-bromo-thiazol-2-yl)-1H-1,2,3-triazol-1-yl]-1-thio-α-D-galactopyranoside,
3,4-Dichlorophenyl 3-deoxy-3-[4-(5-fluoro-thiazol-2-yl)-1H-1,2,3-triazol-1-yl]-1-thio-α-D-galactopyranoside, 3,4-Dichlorophenyl 3-deoxy-3-[4-(4-chloro-thiazol-2-yl)-1H-1,2,3-triazol-1-yl]-1-thio-α-D-galactopyranoside, and 3,4-Dichlorophenyl 3-deoxy-3-[4-(4-trifluoromethyl-thiazol-2-yl)-1H-1,2,3-triazol-1-yl]-1-thio-α-D-galactopyranoside.

17. A pharmaceutical composition comprising the compound of claim 1 and a pharmaceutically acceptable additive.

18. The compound of claim 1 for use in a method for treating a disorder relating to the binding of a galectin-1 to a ligand in a mammal having said disorder.

19. The compound for use according to claim 18, wherein said disorder is selected from the group consisting of inflammation; fibrosis; scarring; keloid formation; aberrant scar formation; scleroderma; sclerosis; surgical adhesions; septic shock; cancer; neovascularization related to cancer; autoimmune diseases; transplant rejection; metabolic disorders; heart disease; heart failure; pathological angiogenesis; eye diseases; atherosclerosis; obesity; interstitial lung diseases; and liver disorders.

20. A method for treatment of a disorder relating to the binding of a galectin-1 to a ligand in a mammal wherein said disorder is selected from the group consisting of inflammation; fibrosis; scarring; keloid formation; aberrant scar formation; scleroderma; sclerosis; surgical adhesions; septic shock; cancer; neovascularization related to cancer; autoimmune diseases; transplant rejection; metabolic disorders; heart disease; heart failure; pathological angiogenesis; eye diseases; atherosclerosis; obesity; interstitial lung diseases; and liver disorders; wherein a therapeutically effective amount of at least one compound according to claim 1 is administered to a mammal having said disorder.

21. The compound for use according to claim 19, wherein said cancer is a metastasising cancer.

22. The compound for use according to claim 19, wherein said interstitial lung disease is asthma.

23. The method according to claim 20, wherein said cancer is a metastasising cancer.

24. The method according to claim 20, wherein said interstitial lung disease is asthma.

* * * * *